United States Patent
Sakai et al.

(10) Patent No.: US 10,899,717 B2
(45) Date of Patent: Jan. 26, 2021

(54) 4-METHYLDIHYDROPYRIMIDINONE COMPOUNDS AND PHARMACEUTICAL USE THEREOF

(71) Applicant: Japan Tobacco Inc., Tokyo (JP)

(72) Inventors: Takayuki Sakai, Osaka (JP); Taku Ikenogami, Osaka (JP)

(73) Assignee: JAPAN TOBACCO INC., Tokyo (JP)

( * ) Notice: Subject to any disclaimer, the term of this patent is extended or adjusted under 35 U.S.C. 154(b) by 0 days.

(21) Appl. No.: 16/287,870

(22) Filed: Feb. 27, 2019

(65) Prior Publication Data
US 2019/0300488 A1 Oct. 3, 2019

(30) Foreign Application Priority Data
Feb. 28, 2018 (JP) .................... 2018-035597

(51) Int. Cl.
C07D 239/22 (2006.01)
C07D 233/70 (2006.01)
A61P 37/02 (2006.01)

(52) U.S. Cl.
CPC ............ *C07D 233/70* (2013.01); *A61P 37/02* (2018.01)

(58) Field of Classification Search
CPC .................... A61K 31/513; C07D 239/22
USPC .......................................... 514/274; 544/318
See application file for complete search history.

(56) References Cited

U.S. PATENT DOCUMENTS

| | | | |
|---|---|---|---|
| 4,485,107 A | 11/1984 | Kennis | |
| 7,671,061 B2 | 3/2010 | Moran | |
| 8,178,542 B2 | 5/2012 | Moran | |
| 8,389,529 B2 | 3/2013 | Moran | |
| 8,541,423 B2 | 9/2013 | Moran | |
| 8,604,069 B2 | 12/2013 | Maeba et al. | |
| 9,458,104 B2 | 10/2016 | Gege | |
| 9,815,838 B2 | 11/2017 | Moran | |
| 10,035,790 B2 | 7/2018 | Xu et al. | |
| 10,196,363 B2 | 2/2019 | Yokota et al. | |
| 10,351,567 B2 | 7/2019 | Moran | |
| 2007/0219222 A1 | 9/2007 | Moran | |
| 2010/0010024 A1 | 1/2010 | Von | |
| 2010/0267750 A1 | 10/2010 | Moran | |
| 2011/0009430 A1 | 1/2011 | Moran | |
| 2011/0201634 A1 | 8/2011 | Parmar | |
| 2012/0322837 A1 | 12/2012 | Maeba et al. | |
| 2013/0123283 A1 | 5/2013 | Moran | |
| 2014/0221401 A1 | 8/2014 | Moran | |
| 2014/0296306 A1 | 10/2014 | Maeba et al. | |
| 2015/0175556 A1 | 6/2015 | Ambroise et al. | |
| 2015/0266856 A1 | 9/2015 | Xu et al. | |
| 2015/0344423 A1 | 12/2015 | Gege | |
| 2016/0137639 A1 | 5/2016 | Kotoku et al. | |
| 2016/0194290 A1 | 7/2016 | Yokota et al. | |
| 2016/0346256 A1 | 12/2016 | Maeba et al. | |
| 2018/0093986 A1 | 4/2018 | Moran | |

(Continued)

FOREIGN PATENT DOCUMENTS

| | | |
|---|---|---|
| AU | 2083483 A | 5/1984 |
| CA | 2656307 A1 | 1/2008 |
| CL | 201701466 A1 | 1/2018 |

(Continued)

OTHER PUBLICATIONS

Baeten, D. et al. (Nov. 23, 2013; e-pub. Sep. 13, 2013). "Anti-Interleukin-17A Monoclonal Antibody Secukinumab in Treatment of Ankylosing Spondylitis: A Randomised, Double-Blind, Placebo-Controlled Trial," *Lancet* 382(9906):1705-1713.

(Continued)

*Primary Examiner* — Jeffrey H Murray
(74) *Attorney, Agent, or Firm* — Morrison & Foerster LLP

(57) ABSTRACT

The present invention relates to 4-methyldihydropyrimidinone compounds, or pharmaceutically acceptable salts thereof, having RORγ antagonist activity, pharmaceutical compositions comprising the same, and pharmaceutical use thereof. A compound of Formula (1) or (2) or a pharmaceutically acceptable salt thereof, a pharmaceutical composition comprising the same, and pharmaceutical use thereof are provided.

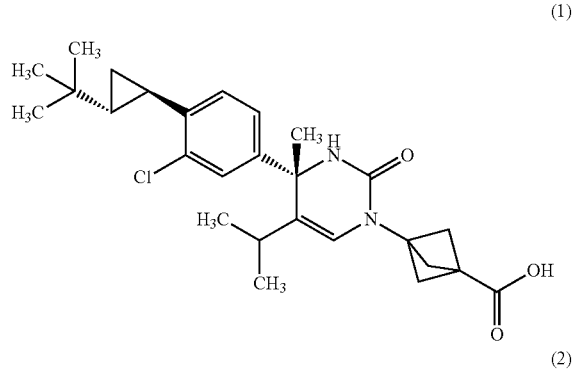

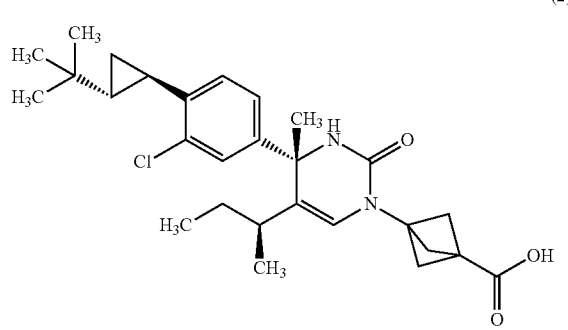

20 Claims, 6 Drawing Sheets

(56) References Cited

U.S. PATENT DOCUMENTS

2019/0359575 A1    11/2019    Yokota

FOREIGN PATENT DOCUMENTS

| | | |
|---|---|---|
| CL | 201701478 A1 | 1/2018 |
| CL | 201701511 A1 | 2/2018 |
| CN | 103113308 A | 5/2013 |
| EP | 0110435 B1 | 1/1989 |
| IE | 832540 L | 5/1984 |
| JP | 2009521485 A | 6/2009 |
| JP | 2015524449 A | 8/2015 |
| PT | 77493 A | 11/1983 |
| SU | 1313349 A3 | 5/1987 |
| WO | WO2007073505 A2 | 6/2007 |
| WO | WO2007073505 A3 | 6/2007 |
| WO | WO2008003412 A1 | 1/2008 |
| WO | WO2009150668 A1 | 12/2009 |
| WO | WO-2012/147916 A1 | 11/2012 |
| WO | WO2014023367 A1 | 2/2014 |
| WO | WO-2014/062938 A1 | 4/2014 |
| WO | WO-2014/065413 A1 | 5/2014 |
| WO | WO-2014/203044 A1 | 12/2014 |
| WO | WO-2016/091346 A1 | 6/2016 |
| WO | WO-2016/091997 A1 | 6/2016 |
| WO | WO-2016/093342 A1 | 6/2016 |
| WO | WO-2016/094824 A1 | 6/2016 |

OTHER PUBLICATIONS

Contreras-Ruiz, L. et al. (2016; e-pub. Oct. 14, 2015). "Sjöogren's Syndrome Associated Dry Eye in a Mouse Model is Ameliorated by Topical Application of Integrin A4 Antagonist GW559090," *Experimental Eye Research* 143:1-8.

Crispin, J.C. et al. (2010). "Interleukin-17-Producing T Cells in Lupus," *Current Opinion in Rheumatology* 22(5):499-503.

De Wit, J. et al. (Mar. 2016; e-pub. Nov. 21, 2015). "RORγt Inhibitors Suppress $T_H$ 17 Responses in Inflammatory Arthritis and Inflammatory Bowel Disease," *J. Allergy Clin. Immunol.* 137(3):960-963.

Dubernet, M. et al. (Apr. 10, 2013). "Identification of New Nonsteroidal RORα Ligands; Related Structure-Activity Relationships and Docking Studies," *ACS Medicinal Chemistry Letters* 4(6):504-508.

Dutzan, N. et al. (Oct. 17, 2018). "A Dysbiotic Microbiome Triggers TH17 Cells to Mediate Oral Mucosal Immunopathology in Mice and Humans," *Sci. Transl. Med.* 10(463):eaat0797, 13 pages.

Emamaullee, J.A. et al. (Jun. 2009). "Inhibition of Th17 Cells Regulates Autoimmune Diabetes in NOD Mice," *Diabetes* 58:1302-1311.

Fauber, B.P. et al. (Feb. 6, 2014). "Modulators of the Nuclear Receptor Retinoic Acid Receptor-Related Orphan Receptor-γ (RORγ or RORc)," *J. Med. Chem.* 57:5871-5892.

Fauber, B.P. et al. (Jul. 2015). "Discovery of 1-14-[3-Fluoro-4-((3s,6r)-3-Methyl-1,1-Dioxo-6-Phenyl-[1,2]Thiazinan-2-Ylmethyl)-Phenyl]-Piperazin-1-Yl)-Ethanone (GNE-3500):A Potent, Selective, and Orally Bioavailable Retinoic Acid Receptor-Related Orphan Receptor C (Rorc or Rory) Inverse Agonist," *J. Med. Chem.* 58(13):5308-5322.

Feagan, B.G. et al. (Apr. 29, 2017; e-pub. Apr. 12, 2017). "Induction Therapy With the Selective Interleukin-23 Inhibitor Risankizumab in Patients With Moderate-to-Severe Crohn's Disease: A Randomised, Double-Blind, Placebo-Controlled Phase 2 Study," *The Lancet* 389(10080):1699-1709.

Fulton, L.M. et al. (2012; e-pub. Jul. 9, 2012). "Attenuation of Acute Graft-versus-Host Disease in the Absence of the Transcription Factor RORγt," *Journal of Immunology* 189(4):1765-1772.

Havrdova, E. et al. (Jul. 2016; e-pub. May 3, 2016). "Activity of Secukinumab, an Anti-IL-17A Antibody, on Brain Lesions in RRMS: Results From a Randomized, Proof-of-Concept Study," *J. Neurol.* 263(7):1287-1295.

Hueber, W. et al. (Oct. 6, 2010). "Effects of AIN457, a Fully Human Antibody to Interleukin-HA, on Psoriasis, Rheumatoid Arthritis, and Uveitis," *Science Translational Medicine* 2(52):52ra72, 11 pages.

Isono, F. et al.(Aug. 2014). "Inhibiting RORγt/Th17 Axis for Autoimmune Disorders," *Drug Discovery Today* 19(8):1205-1211.

Ivanov, I.I. et al. (Sep. 22, 2006). "The Orphan Nuclear Receptor RORγt Directs the Differentiation Program of Proinflammatory IL-17$^+$ T Helper Cells," *Cell* 126(6):1121-1133.

Jetten, A.M. (2009; e-pub. Apr. 3, 2009). "Retinoid-Related Orphan Receptors (RORs): Critical Roles in Development, Immunity, Circadian Rhythm, and Cellular Metabolism," *Nucl. Recept. Signal.* 7:e003, 32 pages.

Ji, J. et al. (2014; e-pub. Sep. 3, 2014). "Novel Benzenediamine Derivative FC99 Ameliorates Zymosan-Induced Arthritis by Inhibiting RORγt Expression and Th17 Cell Differentiation," *Acta Biochim. Biophys. Sin.* 46(10):829-836.

Kelchtermans, H. et al. (Aug. 17, 2009). "Effector Mechanisms of Interleukin-17 in Collagen-Induced Arthritis in the Absence of Interferon-γ and Counteraction by Interferon-γ," *Arthritis Research & Therapy* 11(4):R122, 13 pages.

Kim, S.-H. et al. (2014; e-pub. Dec. 27, 2013). "Oleanolic Acid Suppresses Ovalbumin-Induced Airway Inflammation and Th2-Mediated Allergic Asthma by Modulating the Transcription Factors T-Bet, GATA-3, Rorγt and Foxp3 in Asthmatic Mice," *International Immunopharmacology* 18:311-324.

Koenders, M.I. et al. (Dec. 2006). "Potential New Targets in Arthritis Therapy: Interleukin (IL)-17 And 15 its Relation to Tumour Necrosis Factor and IL-1 in Experimental Arthritis," *Ann. Rheum. Dis.* 65 (Suppl. III):iii29-iii33.

Kumar, R. et al. (2007; e-pub. May 31, 2007). "Design and Synthesis of 6-methyl-2-oxo-1,2,3,4-Tetrahydro-Pyrimidine-5-Carboxylic Acid Derivatives as PPARγ Activators," *Bioorganic & Medicinal Chemistry Letters* 17:4613-4618.

Lauro, G. et al. (2014; e-pub. Apr. 24, 2014). "Exploration of the Dihydropyrimidine Scaffold for Development of New Potential Anti-Inflammatory Agents Blocking Prostaglandin $E_2$ Synthase-1 Enzyme (MPGES-1)," *European Journal of Medicinal Chemistry* 80:407-415.

Lee, S.-Y. et al. (Jul. 21, 2015). "Ocotillol, a Majonoside R2 Metabolite, Ameliorates 2,4,6-Trinitrobenzenesulfonic Acid-Induced Colitis in Mice by Restoring the Balance of Th17/Treg Cells," *J. Agric. Food Chem.* 63:7024-7031.

Leppkes, M. et al. (2009). "RORγ-Expressing Th17 Cells Induce Murine Chronic Intestinal Inflammation via Redundant Effects of IL-17A and IL-HF," *Gastroenterology* 136(1):257-267.

Liao, Y.H. et al. (Jan. 24, 2012). "Interleukin-17A Contributes to Myocardial Ischemia/Reperfusion Injury by Regulating Cardiomyocyte Apoptosis and Neutrophil Infiltration," *J. Am. Coll. Cardiol.* 59(4):420-429.

Lin, H. et al. (Nov. 30, 2015). "Targeting Th17 Cells with Small Molecules and Small Interference RNA," *Mediators of Inflammation* 2015(Article ID 290657):1-12.

Marques, M. (May 2004). "Dissolution Media Simulating Fasted and Fed States," *Dissolution Technologies* 11(2):16.

Meissburger, B. et al. (2011). "Adipogenesis and Insulin Sensitivity in Obesity are Regulated by Retinoid-Related Orphan Receptor Gamma," *EMBO Mol. Med.* 3:637-651.

Mi, S. et al. (2011; e-pub. Aug. 11, 2011). "Blocking IL-17 A Promotes the Resolution of Pulmonary Inflammation and Fibrosis Via TGF-β1-Dependent and -Independent Mechanisms," *Journal of Immunology* 187:3003-3014.

Miller, S.D. et al. (Feb. 2010). "Experimental Autoimmune Encephalomyelitis in the Mouse," in *Current Protocols in Immunology*, Unit 15.1., pp. 15.1.1-15.1.20.

Nakae, S. et al. (2003). "Suppression of Immune Induction of Collagen-Induced Arthritis in IL-17-Deficient Mice," *J. Immunol.* 171:6173-6177.

Rodrigues, A.D. et al. (1997). "Oxidative Metabolism of Clarithromycin in the Presence of Human Liver Microsomes—Major Role for the Cytochrome P4503A (CYP3A) Subfamily," *Drug Metabolism and Disposition* 25(5):623-630.

(56) References Cited

OTHER PUBLICATIONS

Saleh, M.A. et al. (2016). "Inhibition of Interleukin 17-A But Not Interleukin-17F Signaling Lowers Blood Pressure and Reduces End-organ Inflammation in Angiotensin II-induced Hypertension," *JACC Basic Transl. Sci.* 1(7):606-616.
Sanford, M. et al. (2015, e-pub. Feb. 4, 2015). "Secukinumab: First Global Approval," *Drugs* 75(3):329-338.
Schmidt-Weber, C.B. et al. (Aug. 2007). "$T_H$ 17 Cells in the Big Picture of Immunology," *J. Allergy Clin. Immunol.* 120(2):247-254.
Shi, W. et al. (2013). "Anti-IL-17 Antibody Improves Hepatic Steatosis by Suppressing 25 Interleukin-17-Related Fatty Acid Synthesis and Metabolism," *Clin. Dev. Immunol.* 2013(Article ID 253046):1-9.
Son, H.-L. et al. (Nov. 2014). "Effect of Retinoic Acid in a Mouse Model of Allergic Rhinitis," *Allergy Asthma Immunol. Res.* 7(6):590-598.
Speeckaert, R. et al. (Nov. 2016; e-pub. Apr. 26, 2016). "The Many Faces of Interleukin-17 in Inflammatory Skin Diseases," *Br. J. Dermatol.* 175(5):892-901.
Steinmetz, O.M. et al. (2011). "The Th17-Defining Transcription Factor RORγt Promotes Glomerulonephritis," *Journal of the American Society of Nephrology* 22(3):472-483.
Sugaya, Y. et al. (2002). "Development of Solubility Screening Methods in Drug Discovery," *Yakugaku Zasshi* 122(3):237-246, (with English translation of Abstract).
Takeda, Y. et al. (May 15, 2014). "Retinoic Acid-Related Orphan Receptor γ (RORγ): A Novel Participant in the Diurnal Regulation of Hepatic Gluconeogenesis and Insulin Sensitivity," *PLOS Genetics*, 10(5):e1 004331, 16 pages.
Terracciano, S. et al. (Jan. 7, 2015). "Structural Insights for the Optimization of Dihydropyrimidin-2(1H)-one Based mPGES-1 Inhibitors," *ACS Medicinal Chemistry Letters* 6:187-191.
Tilley, S.L. et al. (Mar. 1, 2007). "Retinoid-Related Orphan Receptor γ Controls Immunoglobulin Production and Th1/Th2 Cytokine Balance in the Adaptive Immune Response to Allergen," *J. Immunol.* 178(5):3208-3218.
U.S. National Institutes of Health. ClinicalTrials.gov Identifier: NCT02594098 (Nov. 2, 2015). "Secukinumab for Treatment of Atopic Dermatitis—(Official Title)—A Pilot Study to Evaluate the Efficacy and Safety of Secukinumab in the Treatment of Moderate to Severe Atopic Dermatitis," located at <https://clinicaltrials.gov/ct2/show/NCT02594098?term=NCT02594098&rank=1>, last visited on May 2, 2019.
U.S. National Institutes of Health. ClinicalTrials.gov Identifier: NCT02899026. (Sep. 13, 2016). "Efficacy and Safety Study of Sirukumab in Subjects With Polymyalgia Rheumatica. (Official Title)—A Multi-Center, Randomized, Double-Blind, Placebo-Controlled, Parallel Group Study to Evaluate the Efficacy and Safety of Sirukumab in Subjects With Polymyalgia Rheumatica," located at <https://clinicaltrials.gov/ct2/show/NCT02899026?term=NCT02899026&rank=1>, last visited on May 2, 2019.
U.S. National Institutes of Health. ClinicalTrials.gov Identifier: NCT01389973. (Jul. 8, 2011). "A Study of Efficacy and Safety of Ustekinumab in Patients With Primary Biliary Cirrhosis (PBC) Who Had an Inadequate Response to Ursodeoxycholic Acid. (Official Title)—A Phase 2, Multi-center, Randomized, Double-blind, Placebo-controlled, Parallel-group Study Evaluating the Efficacy and Safety of Ustekinumab in Subjects With Primary Biliary Cirrhosis Who Had an Inadequate Response to Ursodeoxycholic Acid (UDCA)," located at <https://clinicaltrials.gov/ct2/show/NCT01389973?term=NCT01389973&rank=1>, last visited on May 2, 2019.
U.S. National Institutes of Health. ClinicalTrials.gov Identifier: NCT02599129. (Nov. 6, 2015). "A Study of Secukinumab for the Treatment of Alopecia Areata. (Official Title)—An Exploratory Study to Evaluate the Safety and Efficacy of Secukinumab in the Treatment of Exensive Alopecia Areata," located at <http://clincaltrials.gov/ct2/show/NCT02599129?term=NCT02599129&rank=1>, last visited on May 2, 2019.
U.S. National Institutes of Health. ClinicalTrials.gov Identifier: NCT03137160. (May 2, 2017). "An Open-Label, Proof-of-Concept Study of Ixekizumab in the Treatment of Pyoderma Gangrenosum," located at <https://clinicaltrials.gov/ct2/show/NCT03137160?term=NCT03137160&rank=1>, last visited on May 2, 2019.
U.S. National Institutes of Health. ClinicalTrials.gov Identifier: NCT02443298. (May 13, 2015). "Efficacy and Safety of BI 655066/ABBV-066 (Risankizumab) in Patients With Severe Persistent Asthma. (Official Title)—Phase IIa, Randomized, Double-blind, Placebo Controlled, Parallel Group Study to Assess the Safety and Efficacy of Subcutaneously Administered BI 655066/ABBV-066 (Risankizumab) as add-on Therapy Over 24 Weeks in Patients With Severe Persistent Asthma," located at <https://clinicaltrials.gov/ct2/show/NCT02443298?term=NCT02443298&rank=1>, last visited on May 2, 2019.
U.S. National Institutes of Health. ClinicalTrials.gov Identifier: NCT02733094. (Apr. 11, 2016). "Single-arm Study to Assess a Potential Effect of Anti-IL-17 (Secukinumab) in the Treatment of Pyoderma Gangrenosum," located at <https://clinicaltrials.gov/ct2/show/NCT02733094?term=NCT02733094&rank=1>, last visited on May 2, 2019.
U.S. National Institutes of Health. ClinicalTrials.gov Identifier: NCT02044848. (Jan. 24, 2014). "Study of Secukinumab in Patients With Newly-diagnosed Type 1 Diabetes Mellitus. (Official Title)—A Randomized, Double-blind, Multiple Dose, Placebo-controlled Study to Evaluate the Safety, Tolerability, Immunogenicity, Pharmacokinetics, and Efficacy of Secukinumab in Adult and Pediatric Patients With New-onset Type 1 Diabetes Mellitus(T1D)," located at <https://clinicaltrials.gov/ct2/show/NCT02044848?term=NCT02044848&rank=1>, last visited on May 2, 2019.
U.S. National Institutes of Health. ClinicalTrials.gov Identifier: NCT01250171. (Nov. 30, 2010). "The Effects of a Single Intravenous Administration of Secukinumab (AIN457) or Canakinumab (ACZ885) in Dry Eye Patients. (Official Title)—A Randomized, Placebo-controlled, Double-blind, Proof-of-concept Study of Intravenous Secukinumab (AIN457) or Canakinumab (ACZ885) in Dry Eye Syndrome," located at <https://clinicaltrials.gov/ct2/show/NCT01250171?term=NCT01250171&rank=1>, last visited on May 2, 2019.
Wang, K. et al., (Apr. 2015). "Cyclosporine A Suppresses the Activation of the Th17 Cells in Patients with Primary Sjögren's Syndrome," *Iran J. Allergy Asthma Immunol*, 14(2):198-207.
Wissel, G. et al. (2015; e-pub. Apr. 17, 2015). "Exploring the Structure-Activity Relationships of ABCC2 Modulators Using a Screening Approach," *Bioorganic & Medicinal Chemistry* 23:3513-3525.
Xiao, S. et al. (Apr. 17, 2014). "Small Molecule RORγt Antagonists Inhibit T Helper 17 Cell Transcriptional Network by Divergent Mechanisms," *Immunity* 40(4):477-489.
Xu, R. et al. (Sep. 2013; e-pub. Jun. 19, 2013). "Neutralization of Interleukin-17 Attenuates High Fat Diet-Induced Non-Alcoholic Fatty Liver Disease in Mice," *Acta Biochim. Biophys. Sin.* 45(9):726-733.
Yang, J. et al. (Oct. 2014). "Targeting Th17 Cells in Autoimmune Diseases," *Trends in Pharmacological Sciences* 35(10):493-500.
Zhang, Q. et al. (Jun. 2017; e-pub. Feb. 27, 2017). "Targeting Th17-IL-17 Pathway in Prevention of Micro-Invasive Prostate Cancer in a Mouse Model," *Prostate* 77(8):888-899, 18 pages.
International Search Report dated Mar. 15, 2016 for PCT Application No. PCT/JP2015/084791 filed on Dec. 11, 2015, 7 pages (with English Translation).
European Extended Search Report dated Aug. 17, 2018 for EP Application No. 15866802.0 filed Dec. 11, 2015, six pages.
U.S. Appl. No. 16/228,448, filed Dec. 20, 2018 by Masahiro Yokota et al.
Shang, N.-Z. et al. (2013). "Synthesis of 3,4-Dihydropyrimidin-2(1H)-One Derivate in the Presence of Carbon-Supported Solid Acid Catalyst," *Huaxue Yanjiu Yu Yingyong* 25(12):1697-1701. English Abstract Only.
International Search Report dated Apr. 23, 2019 for PCT Application No. PCT/JP2019/007433 filed Feb. 28, 2018, 8 pages (with English Translation).
U.S. National Institutes of Health. ClinicalTrials.gov Identifier: NCT01250171. (Nov. 30, 2010). "The Effects of a Single Intrave-

(56) References Cited

OTHER PUBLICATIONS nous Administration of Secukinumab (AIN457) or Canakinumab (ACZ885) in Dry Eye Patients," 8 pages.
U.S. Appl. No. 16/902,935, filed Jun. 16, 2020 by Masahiro Yokota et al.

[Fig. 1]
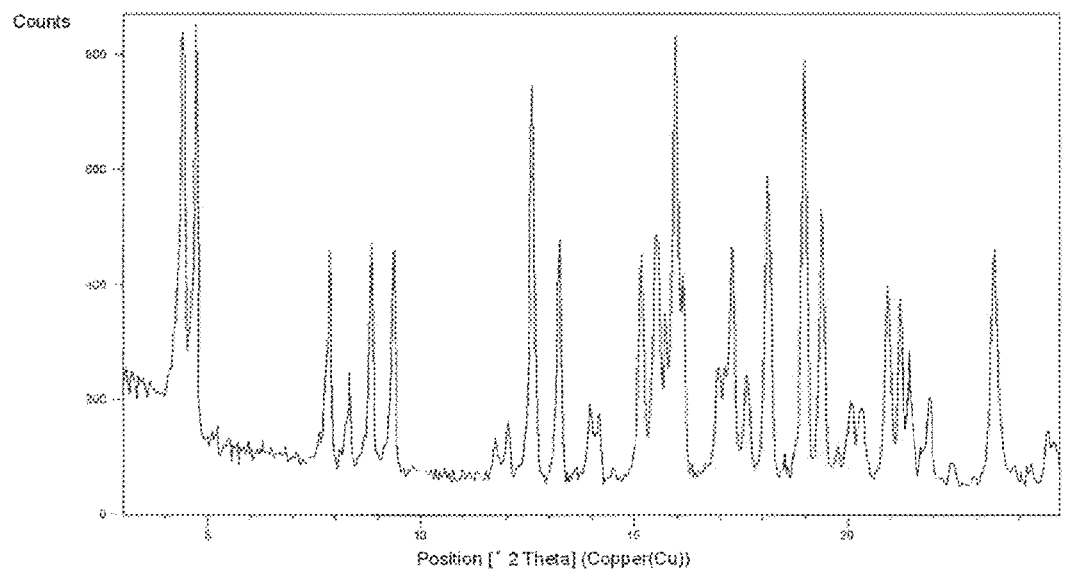
[Fig. 2]
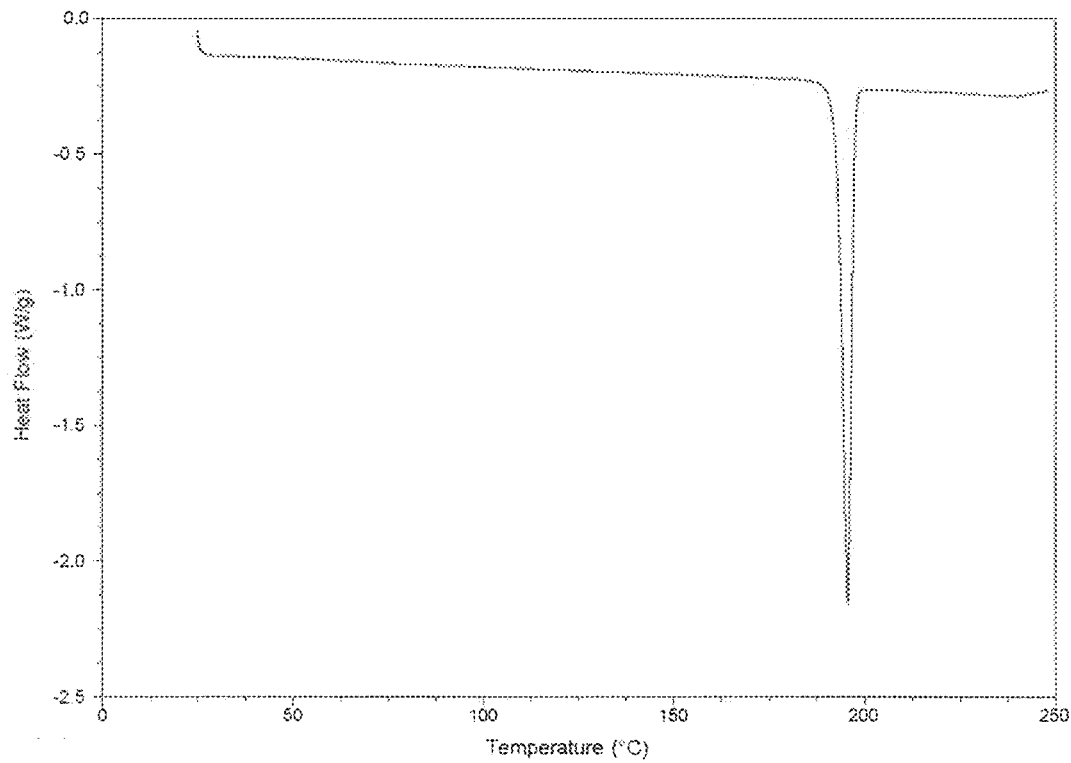

[Fig. 3]
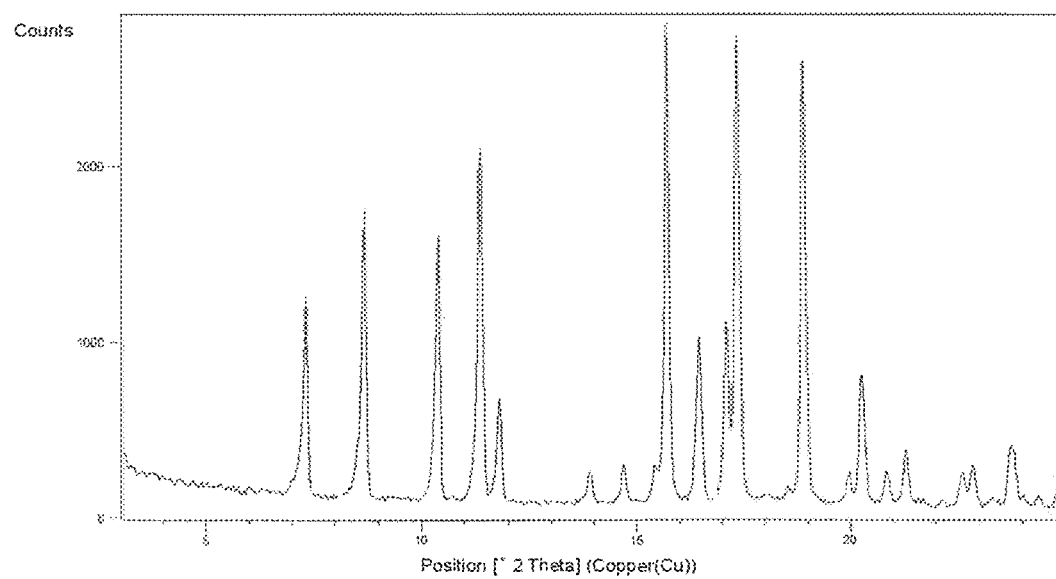
[Fig. 4]
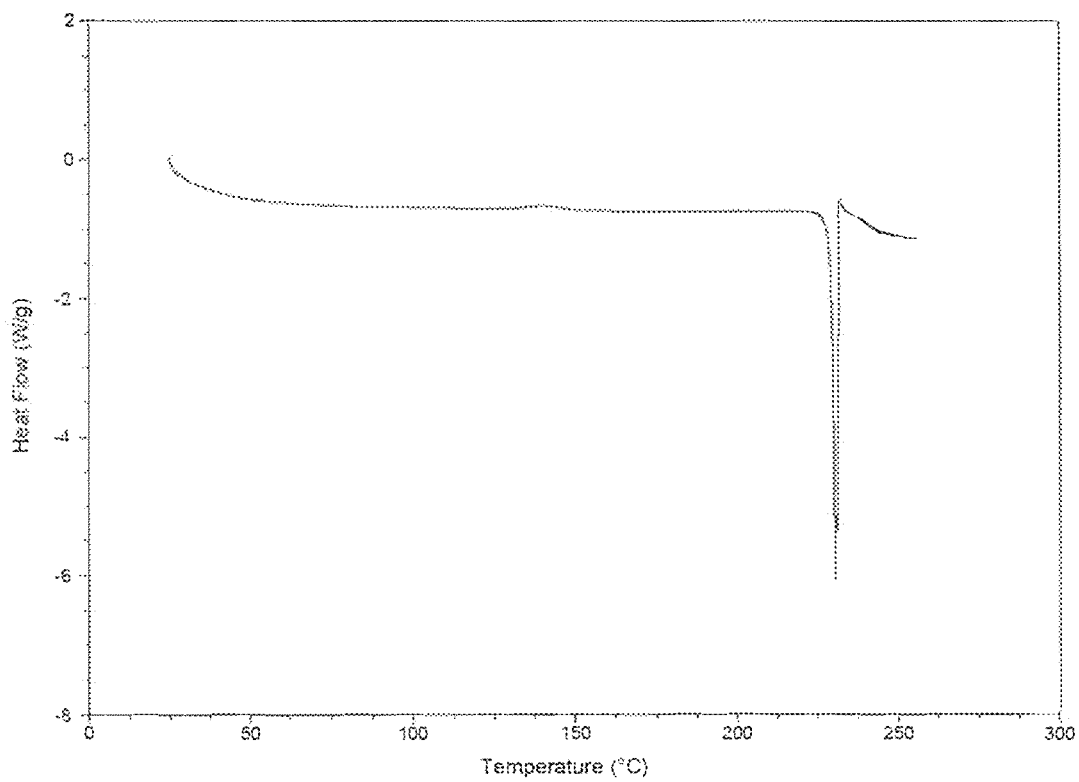

[Fig. 5]
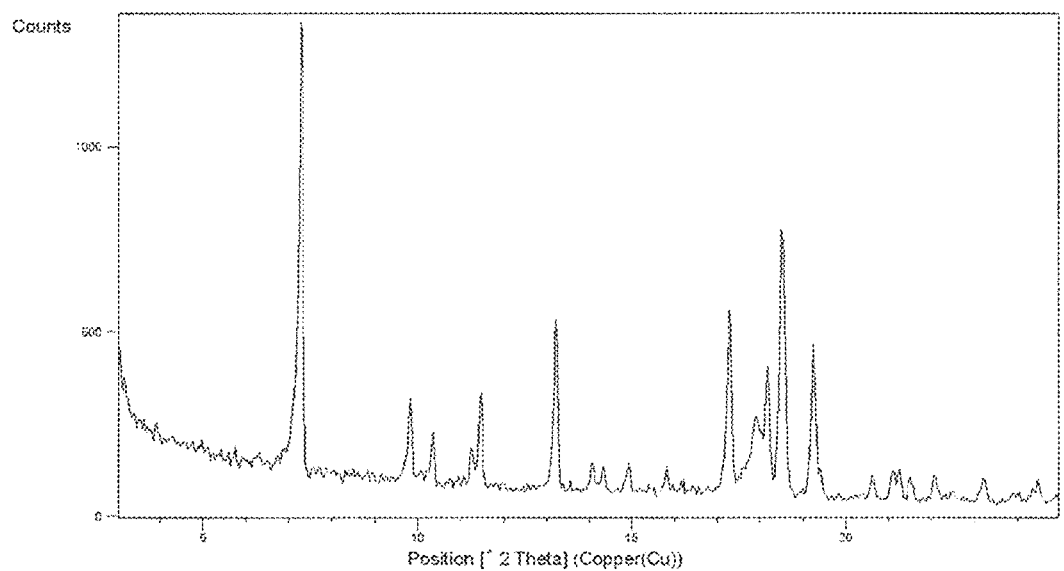
[Fig. 6]
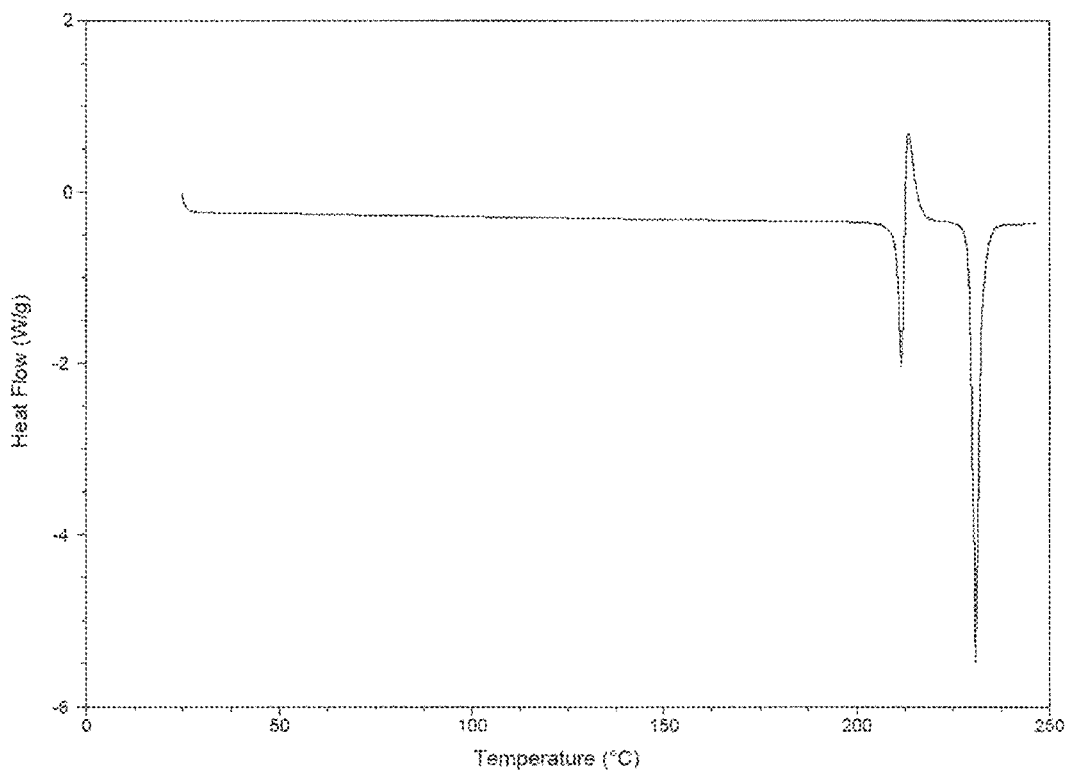

[Fig. 7]
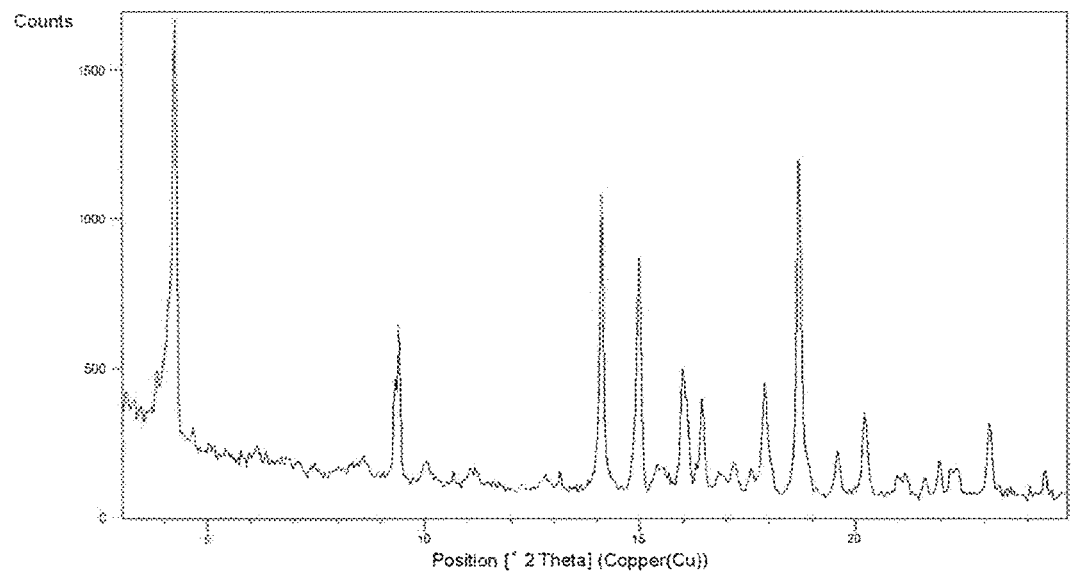
[Fig. 8]
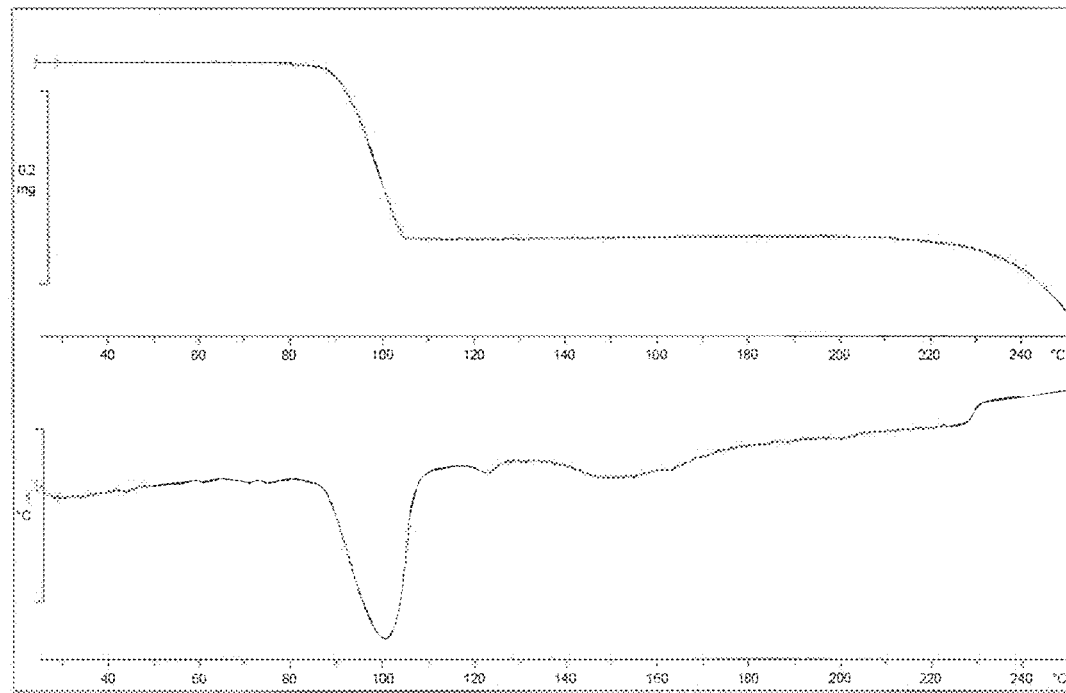

[Fig. 9]
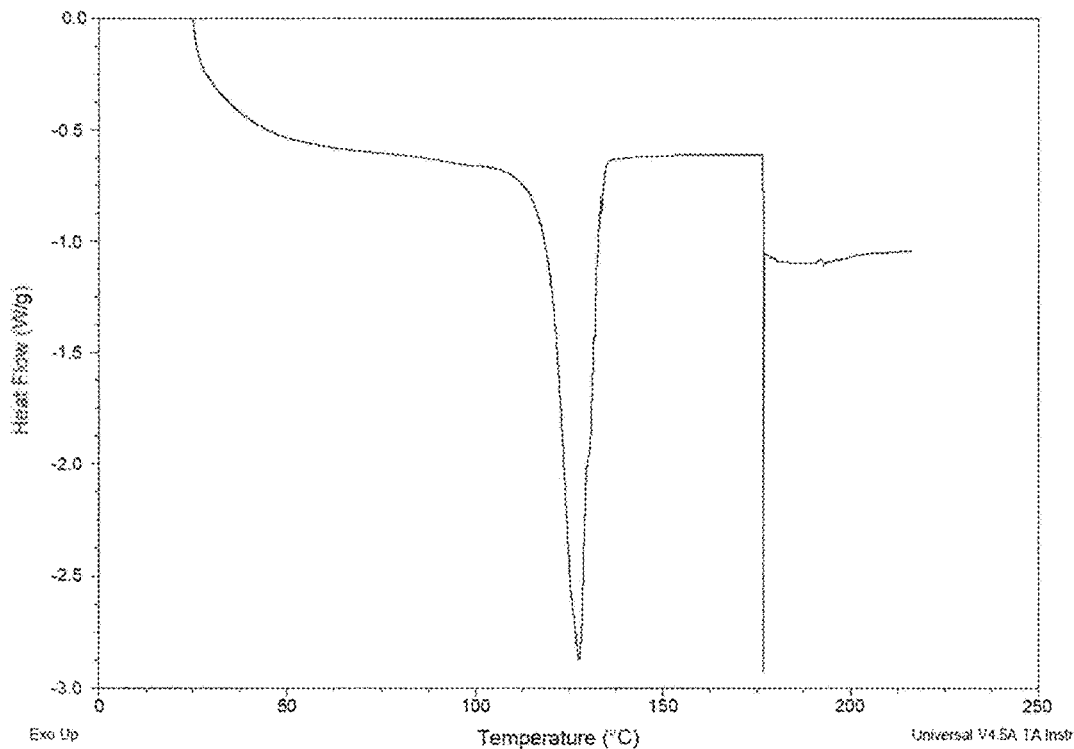
[Fig. 10]
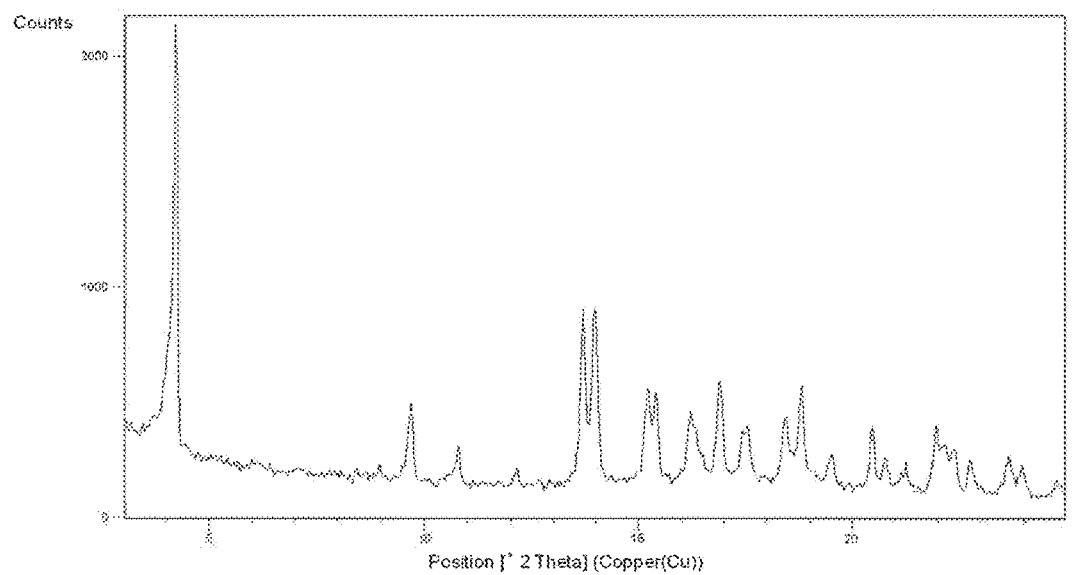

[Fig. 11]
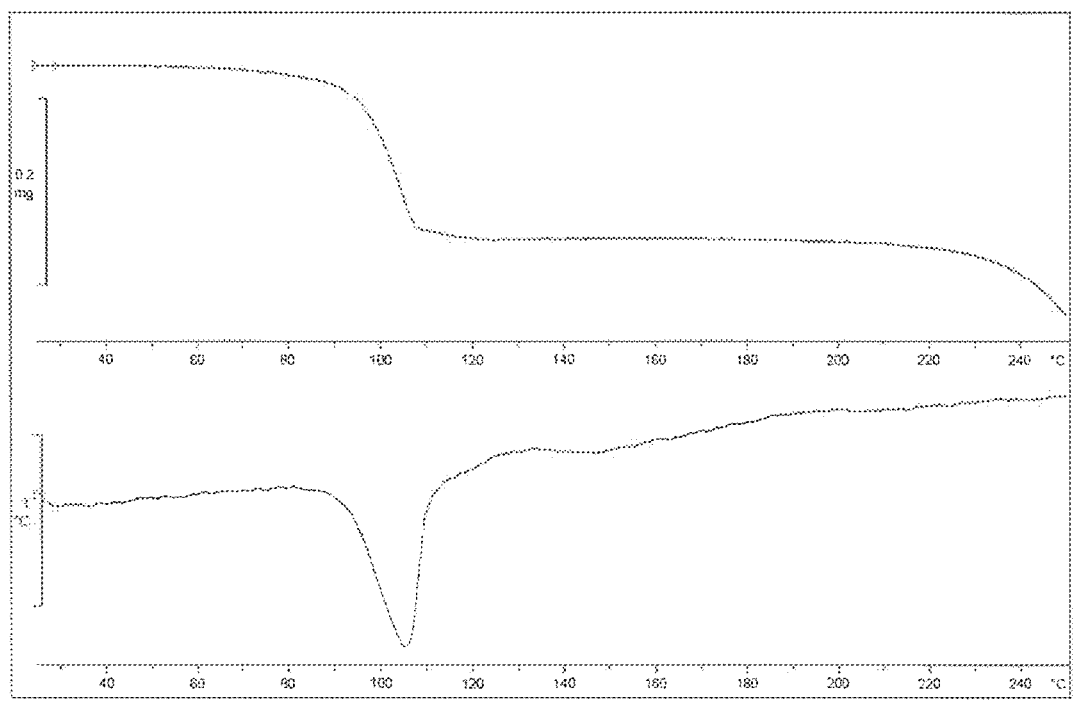
[Fig. 12]
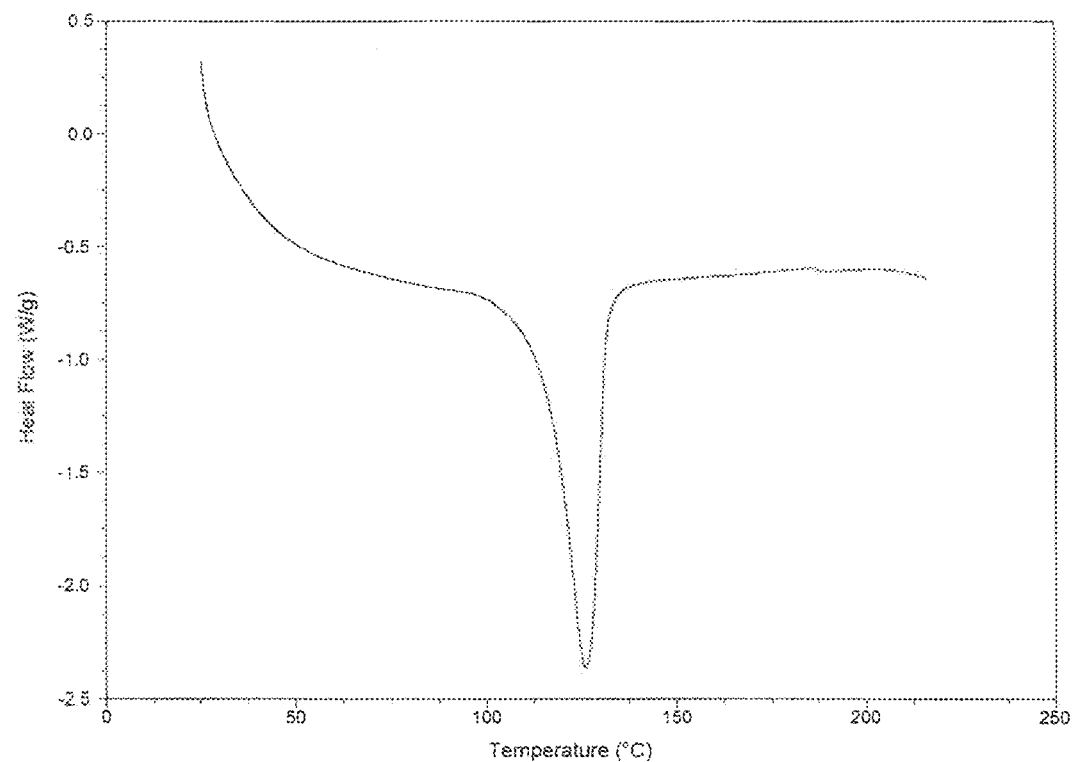

4-METHYLDIHYDROPYRIMIDINONE COMPOUNDS AND PHARMACEUTICAL USE THEREOF

CROSS REFERENCE TO RELATED APPLICATIONS

This application claims priority to and benefit of Japanese Patent Application No. 2018-035597, filed Feb. 28, 2018, the disclosure of which is incorporated herein by reference in its entirety.

TECHNICAL FIELD

The present invention relates to 4-methyldihydropyrimidinone compounds, or pharmaceutically acceptable salts thereof, having RORγ antagonist activity, pharmaceutical compositions comprising the same, and pharmaceutical use thereof.

BACKGROUND ART

RORγ (i.e., Retinoid-related Orphan Receptor gamma) is a nuclear receptor which is important for the differentiation and activation of Th17 cells. RORγt is also known as a splicing variant of RORγ (Non patent literature 1). RORγ and RORγt differ only in their N-terminal domains and share the same ligand-binding domain and DNA-binding domain. It is reported that RORγ is expressed in other tissues besides Th17 cells (Non Patent Literature 1).

Inhibition of RORγ can inhibit the differentiation and activation of Th17 cells. IL-17 produced in Th17 cells is involved in the induction of a variety of chemokines, cytokines, metalloproteases, and other inflammatory mediators and the migration of neutrophil, and therefore, inhibition of IL-17 may lead to inhibit such induction and migration (Non Patent Literatures 2 and 3). It is known that Th17 cells are involved in autoimmune diseases (such as rheumatoid arthritis, psoriasis, inflammatory bowel disease (such as Crohn's disease and ulcerative colitis), multiple sclerosis, systemic lupus erythematosus (SLE), Behcet's disease, sarcoidosis, Harada disease, ankylosing spondylitis, uveitis, polymyalgia rheumatica, type I diabetes, graft-versus-host disease, alopecia areata, and vitiligo), allergic diseases, dry eye, fibrosis (such as lung fibrosis and primary biliary cirrhosis), and cancers (such as malignant melanoma and prostate cancer).

RORγ in adipose tissues is related to the regulation of adipogenesis and inhibition of RORγ can ameliorate insulin resistance (Non Patent Literature 4). It is known that adipose tissues are involved in metabolic diseases (such as hepatic steatosis).

It is also known that IL-17 and Th17 cells are involved in ischemia, cardiomyopathy, hypertension, and periodontitis.

For example, as for rheumatoid arthritis, it is reported that administration of anti-IL-17 antibody can ameliorate swelling and joint destruction associated with collagen-induced arthritis (Non Patent Literature 5). It is also reported that swelling and joint destruction associated with collagen-induced arthritis can be ameliorated in experiments using IL-17-deficient mice (Non Patent Literature 6).

As for psoriasis, it is reported that administration of anti-IL-17 antibody is effective in treating psoriasis in clinical trials (Non Patent Literature 7). Anti IL-17 antibodies have been placed on the market for use in psoriasis (Non Patent Literature 8).

As for inflammatory bowel diseases such as Crohn's disease and ulcerative colitis, adaptive transfer of T cells derived from RORγ-KO mice does not increase IL-17 in the mucosa in a colitis model induced by the adaptive transfer of T cells, thereby the onset of colitis can be inhibited (Non Patent Literature 9). It is also reported that an anti-IL-23 antibody, an antibody against IL-23 which activates Th17 cells, is effective in treating Crohn's disease in clinical trials (Non Patent Literature 20).

As for multiple sclerosis, the disease state of a mouse experimental autoimmune encephalomyelitis model which is an animal model of multiple sclerosis can be inhibited in RORγ-KO mice (Non Patent Literature 10). It is also reported that an anti-IL-17A antibody can ameliorate MRI observation in relapsing remitting multiple sclerosis in clinical trials (Non Patent Literature 21).

As for systemic lupus erythematosus, it is reported that administration of anti-IL-17 antibody can inhibit onset of GBM nephritis model in RORγt-KO mice which is an animal model of glomerulonephritis (Non Patent Literature 11). Administration of anti-IL-17 antibody potentially inhibits nephritis associated with SLE as well (Non Patent Literature 12).

As for ankylosing spondylitis, it is reported that administration of anti-IL-17 antibody is effective in treating ankylosing spondylitis (Non Patent Literature 13).

As for uveitis, it is reported that administration of anti-IL-17 antibody is effective in treating uveitis associated with Behcet's disease, sarcoidosis, and Harada disease (Non Patent Literature 7).

As for polymyalgia rheumatica, efficacy of anti-IL-17 antibody is currently assessed in clinical trials for polymyalgia rheumatica.

As for type I diabetes, administration of anti-IL-17 antibody can inhibit progression of disease states in a NOD mouse model which is a type I diabetes model (Non Patent Literature 14). Efficacy of anti-IL-17A antibody is currently assessed in clinical trials (Non Patent Literature 22).

As for graft-versus-host disease, it is reported that transfection of RORγ-KO-mouse-derived cells can ameliorate survival rates and rejections in a host in a mouse transplant model (Non Patent Literature 19).

As for alopecia areata, efficacy of anti-IL-17A antibody is currently assessed in clinical trials (Non Patent Literature 25).

As for vitiligo, increases of IL-17 and Th17 cells are recognized in patient sera and pathological tissues, respectively (Non Patent Literature 39).

As for allergic diseases such as asthma, attenuated eosinophilic pulmonary inflammation, the reduced number of CD4+ lymphocytes, and the decrease of Th2 cytokines/chemokines levels are exhibited in RORγ-KO mice in an OVA-sensitized model, which then allergic reactions can be inhibited (Non Patent Literature 15). Efficacy of anti-IL-17A antibody is currently assessed in clinical trials for atopic dermatitis (Non Patent Literature 23). Efficacy of anti-IL-23 antibody is currently assessed in clinical trials for asthma (Non Patent Literature 24).

As for dry eye, it is reported that Th17 cells increase in an animal model of dry eye, and efficacy of anti-TL-17 antibody is currently assessed in clinical trials for dry eye patients (Non Patent Literature 16).

As for fibrosis, administration of anti-IL-17 antibody can inhibit inflammation and fibrosis in lung and extend survival of animals in a bleomycin-induced lung fibrosis model which is an animal model of lung fibrosis (Non Patent Literature 17).

As for primary biliary cirrhosis, it is reported that Th17 cells increase in the lesion area of patients with primary biliary cirrhosis, and efficacy of anti-IL-23 antibody is currently assessed in clinical trials (Non Patent Literature 18).

As for malignant melanoma, efficacy of anti-IL-17 antibody is currently assessed in clinical trials (Non Patent Literatures 26 and 27).

As for prostate cancer, it is recognized that anti-IL-17 antibody treatment decreased the formation of micro-invasive prostate cancer in Pten-null mice (Non Patent Literature 33).

As for insulin resistance, the insulin resistance induced by feeding high-fat diets can be inhibited in RORγ KO mice (Non Patent Literature 4).

As for hepatic steatosis, it is recognized that anti-IL-17 antibody ameliorated steatosis on pathological tissues in an alcoholic liver-disease model (Non Patent Literature 34).

As for non-alcoholic fatty liver disease, it is recognized that anti-IL-17 antibody treatment improved liver function, attenuated hepatic lipid accumulation, suppressed Kupffer cells activation, and decreased proinflammatory cytokines levels in a high fat diet-induced non-alcoholic fatty liver disease model (Non Patent Literature 35).

As for ischemia and cardiomyopathy, it is reported that IL-17A contributes to myocardial ischemia/reperfusion injury by regulating cardiomyocyte apoptosis and neutrophil infiltration. It is recognized that anti-IL-17A antibody treatment or IL-17A knockout reduced infarct size, improved cardiac function, and thus, ameliorated ischemia/reperfusion injury (Non Patent Literature 36).

As for hypertension, it is reported that treatment with antibody against IL-17A or IL-17RA suppressed increased blood pressure by administration of angiotensin II (Non Patent Literature 37).

As for periodontitis, increase of Th17 cells or IL-17 was recognized in an experimental periodontitis model. It is reported that treatment with RORγ antagonist, GSK805, or anti-IL-17A antibody diminished bone loss in the model (Non Patent Literature 38).

On the basis of these findings, RORγ antagonists are deemed to be beneficial for preventing or treating autoimmune diseases, allergic diseases, dry eye, fibrosis, cancers (such as malignant melanoma and prostate cancer), metabolic disease, ischemia, cardiomyopathy, hypertension, and periodontal disease.

[Non Patent Literature 1] JETTEN, "Retinoid-related orphan receptors (RORs): critical roles in development, immunity, circadian rhythm, and cellular metabolism", Nucl. Recept. Signal., 7: e003 (2009).

[Non Patent Literature 2] KOENDERS, et al., "Potential new targets in arthritis therapy: interleukin (IL)-17 and its relation to tumour necrosis factor and IL-1 in experimental arthritis", Ann. Rheum. Dis., 65: iii29-33 (2006).

[Non Patent Literature 3] SCHMIDT-WEBER, et al., "Th17 cells in the big picture of immunology", J. Allergy Clin. Immunol., 120: 247-54 (2007).

[Non Patent Literature 4] MEISSBURGER, et al., "Adipogenesis and insulin sensitivity in obesity are regulated by retinoid-related orphan receptor gamma", EMBO Mol. Med., 3: 637-51 (2011).

[Non Patent Literature 5] KELCHTERMANS et al., "Effector mechanisms of interleukin-17 in collagen-induced arthritis in the absence of interferon-γ and counteraction by interferon-γ", Arthritis Res. Ther., 11(4): R122 (2009).

[Non Patent Literature 6] NAKAE, et al., "Suppression of Immune Induction of Collagen-Induced Arthritis in IL-17-Deficient Mice", J. Immunol., 171: 6173-6177 (2003).

[Non Patent Literature 7] HUEBER et al., "Effects of AIN457, a Fully Human Antibody to Interleukin-17A, on Psoriasis, Rheumatoid Arthritis, and Uveitis", Sci. Transl. Med., 2(52): 52ra72 (2010).

[Non Patent Literature 8] SANFORD et al., "Secukinumab: first global approval", Drugs, 75(3): 329-338 (2015).

[Non Patent Literature 9] LEPPKES, et al, "RORγ-Expressing Th17 Cells Induce MurineChronic Intestinal Inflammation via Redundant Effects of IL-17A and IL-17F", Gastroenterology, 136(1): 257-267 (2009).

[Non Patent Literature 10] IVANOV et al., "The Orphan Nuclear Receptor RORγt Directs the Differentiation Program of Proinflammatory IL-17+T Helper Cells", Cell, 126(6): 1121-1133 (2006).

[Non Patent Literature 11] STEINMETZ et al., "The Th17-Defining Transcription Factor RORγt Promotes Glomerulonephritis", J. Am. Soc. Nephrol., 22(3): 472-483 (2011).

[Non Patent Literature 12] CRISPIN et al., "Interleukin-17-producing T cells in lupus", Curr. Opin. Rheumatol., 22(5): 499-503 (2010).

[Non Patent Literature 13] BAETEN et al., "Anti-interleukin-17A monoclonal antibody secukinumab in treatment of ankylosing spondylitis: a randomised, double-blind, placebo-controlled trial", Lancet, 382(9906): 1705-1713 (2013).

[Non Patent Literature 14] EMAMAULLEE et al., "Inhibition of Th17 Cells Regulates Autoimmune Diabetes in NOD Mice", Diabetes, 58: 1302-1311 (2009).

[Non Patent Literature 15] TILLEY, et al., "Retinoid-Related Orphan Receptor γ Controls Immunoglobulin Production and Th1/Th2 Cytokine Balance in the Adaptive Immune Response to Allergen", J. Immunol., 178: 3208-3218 (2007).

[Non Patent Literature 16] U.S. NATIONAL INSTITUTES OF HEALTH, "The Effects of a Single Intravenous Administration of Sccukinumab (AIN457) or Canakinumab (ACZ885) in Dry Eye Patients", ClinicalTrials.gov information for Clinical Trials Identifier NCT01250171 (Dec. 4, 2012).

[Non Patent Literature 17] M I et al., "Blocking IL-17A Promotes the Resolution of Pulmonary Inflammation and Fibrosis Via TGF-β1-Dependent and -Independent Mechanisms", J. Immunol., 187: 3003-3014 (2011).

[Non Patent Literature 18] U.S. NATIONAL INSTITUTES OF HEALTH, "A Study of Efficacy and Safety of Ustekinumab in Patients With Primary Biliary Cirrhosis (PBC) Who Had an Inadequate Response to Ursodeoxycholic Acid", ClinicalTrials.gov information for Clinical Trials Identifier NCT01389973 (Apr. 2, 2015).

[Non Patent Literature 19] FULTON et al., "Attenuation of Acute Graft-versus-Host Disease in the Absence of the Transcription Factor RORγt", J. Immunol., 189(4): 1765-1772 (2012).

[Non Patent Literature 20] Brian G Feagan et al., "Induction therapy with the selective interleukin-23 inhibitor risankizumab in patients with moderate-to-severe Crohn's disease: a randomised, double-blind, placebo-controlled phase 2 study", The Lancet, 389(10080): 1699-1709 (2017).

[Non Patent Literature 21] Eva Havrdova et al., "Activity of secukinumab, an anti-IL-17A antibody, on brain lesions in RRMS: results from a randomized, proof-of-concept study", J. Neurol., 263(7): 1287-1295 (2016).

[Non Patent Literature 22] U.S. NATIONAL INSTITUTES OF HEALTH, "Study of Secukinumab in Patients With Newly-diagnosed Type 1 Diabetes Mellitus", ClinicalTrials.gov information for Clinical Trials Identifier NCT02044848.

[Non Patent Literature 23] U.S. NATIONAL INSTITUTES OF HEALTH, "Secukinumab for Treatment of Atopic Dermatitis", ClinicalTrials.gov information for Clinical Trials Identifier NCT02594098.

[Non Patent Literature 24] U.S. NATIONAL INSTITUTES OF HEALTH, "Efficacy and Safety of BI 655066/ABBV-066 (Risankizumab) in Patients With Severe Persistent Asthma", ClinicalTrials.gov information for Clinical Trials Identifier NCT02443298.

[Non Patent Literature 25] U.S. NATIONAL INSTITUTES OF HEALTH, "A Study of Secukinumab for the Treatment of Alopecia Areata", ClinicalTrials.gov information for Clinical Trials Identifier NCT02599129.

[Non Patent Literature 26] U.S. NATIONAL INSTITUTES OF HEALTH, "An Open-Label, Proof-of-Concept Study of Ixekizumab in the Treatment of Pyoderma Gangrenosum", ClinicalTrials.gov information for Clinical Trials Identifier NCT03137160.

[Non Patent Literature 27] U.S. NATIONAL INSTITUTES OF HEALTH, "Single-arm Study to Assess a Potential Effect of Anti-IL-17 (Secukinumab) in the Treatment of Pyoderma Gangrenosum", ClinicalTrials.gov information for Clinical Trials Identifier NCT02733094.

[Non Patent Literature 28] A. David Rodrigues et al., "Oxidative Metabolism of Clarithronycin in the Presence of Human Liver Microsomes", Drug Metabolism and Disposition, 25(5): 623-630 (1997).

[Non Patent Literature 29] Yukiko Sugaya et al., "Development of Solubility Screening Methods in Drug Discovery", YAKUGAKU ZASSHI, 122(3): 237-246 (2002).

[Non Patent Literature 30] Margareth Marques, "Dissolution Media Simulating Fasted and Fed States", Dissolution Technologies, 11(2): 16 (2004).

[Non Patent Literature 31] Miller S D et al., "Experimental autoimmune encephalomyelitis in the mouse.", Current Protocols in Immunology, Chapter 15: Unit 15.1. (2010)

[Non Patent Literature 32] Fauber E P et al., "Discovery of 1-{4-[3-flucro-4-((3s,6r)-3-methyl-1,1-dioxo-6-phenyl-[1,2]thiazinan-2-ylmethyl)-phenyl]-piperazin-1-yl}-ethanone (GNE-3500): a potent, selective, and orally bioavailable retinoic acid receptor-related orphan receptor C (RORc or RORγ) inverse agonist.", J. Med. Chem., 58(13): 5308-22 (2015)

[Non Patent Literature 33] Q Zhang et al., "Targeting Th17-IL-17 Pathway in Prevention of Micro-Invasive Prostate Cancer in a Mouse Model", Prostate, 77(8): 888-899 (2017).

[Non Patent Literature 34] W Shi et al., "Anti-IL-17 Antibody Improves Hepatic Steatosis by Suppressing Interleukin-17-Related Fatty Acid Synthesis and Metabolism", Clin. Dev. Immunol., Volume 2013, Article ID 253046 (2013).

[Non Patent Literature 35] R Xu et al., "Neutralization of interleukin-17 attenuates high fat diet-induced non-alcoholic fatty liver disease in mice", Acta Biochim. Biophys. Sin. (Shanghai), 45(9): 726-733 (2013).

[Non Patent Literature 36] Y. H. Lial et al., "Interleukin-17A Contributes to Myocardial Ischemia/Reperfusion Injury by Regulating Cardiomyocyte Apoptosis and Neutrophil Infiltration", J. Am. Coll. Cardiol. 59(4): 420-429 (2012).

[Non Patent Literature 37] M. A. Saleh et al., "Inhibition of Interleukin 17-A but not Interleukin-17F Signaling Lowers Blood Pressure and Reduces End-organ Inflammation in Angiotensin II-induced Hypertension", JACC Basic Transl. Sci. 1(7): 606-616 (2016).

[Non Patent Literature 38] N. Dutzan et al., "A dysbiotic microbiome triggers TH17 cells to mediate oral mucosal immunopathology in mice and humans", Sci. Transl. Med. 10(463): eaat0797 (2018).

[Non Patent Literature 39] R Speeckaert et al., "The many faces of interleukin-17 in inflammatory skin diseases", Br. J. Dermatol. 175(5): 892-901 (2016).

SUMMARY OF INVENTION

The present invention provides 4-methyldihydropyrimidinone compounds, or pharmaceutically acceptable salts thereof, having RORγ antagonist activity, pharmaceutical compositions comprising the same, and their medical use. One aspect of the present invention includes the following illustrative embodiments.

[Item 1]

A compound of Formula (1) or (2):

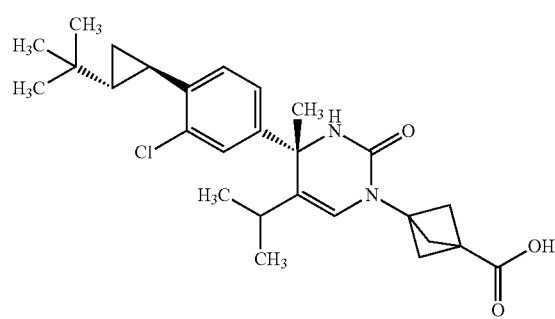

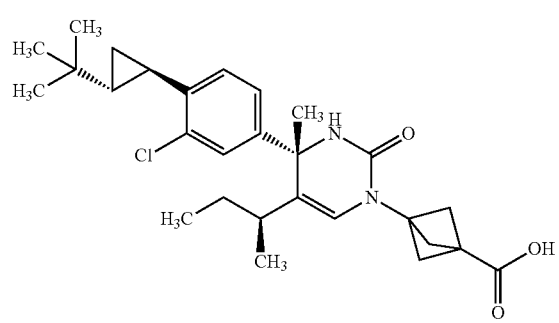

or a pharmaceutically acceptable salt thereof.

[Item 2]

The compound according to Item 1, wherein the compound is a compound of Formula (1):

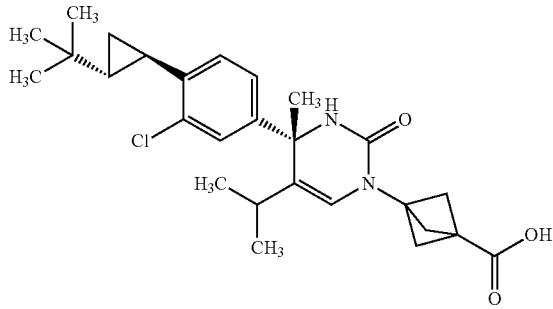

(1)

or a pharmaceutically acceptable salt thereof.

[Item 3]

The compound according to Item 1, wherein the compound is a compound of Formula (2):

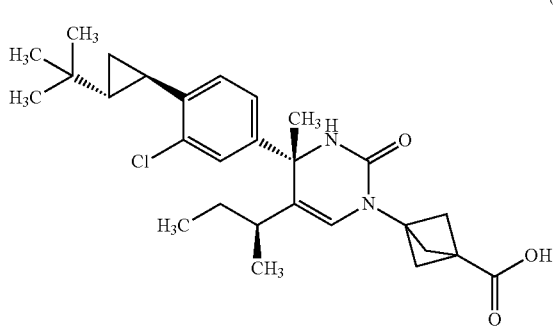

(2)

or a pharmaceutically acceptable salt thereof.

[Item 4]

A pharmaceutical composition comprising a compound according to any one of Items 1 to 3 or a pharmaceutically acceptable salt thereof and a pharmaceutically acceptable carrier.

[Item 5]

An RORγ antagonist comprising a compound according to any one of Items 1 to 3 or a pharmaceutically acceptable salt thereof.

[Item 6]

A therapeutic or preventive agent for a disease selected from the group consisting of autoimmune diseases, allergic diseases, dry eye, fibrosis, cancers, metabolic disease, ischemia, cardiomyopathy, hypertension, and periodontal disease, comprising a compound according to any one of Items 1 to 3 or a pharmaceutically acceptable salt b thereof.

[Item 7]

A method of antagonizing RORγ, comprising administering a therapeutically effective amount of a compound according to any one of Items 1 to 3 or a pharmaceutically acceptable salt thereof to a mammal.

[Item 8]

A method of treating or preventing a disease selected from the group consisting of autoimmune diseases, allergic diseases, dry eye, fibrosis, cancers, metabolic disease, ischemia, cardiomyopathy, hypertension, and periodontal disease, comprising administering a therapeutically effective amount of a compound according to any one of Items 1 to 3 or a pharmaceutically acceptable salt thereof to a mammal.

[Item 9]

Use of a compound according to any one of Items 1 to 3 or a pharmaceutically acceptable salt thereof in the manufacture of an RORγ antagonist.

[Item 10]

Use of a compound according to any one of Items 1 to 3 or a pharmaceutically acceptable salt thereof in the manufacture of a therapeutic or preventive agent for a disease selected from the group consisting of autoimmune diseases, allergic diseases, dry eye, fibrosis, cancers, metabolic disease, ischemia, cardiomyopathy, hypertension, and periodontal disease.

[Item 11]

A compound according to any one of Items 1 to 3 or a pharmaceutically acceptable salt thereof for use in an RORγ antagonist.

[Item 12]

A compound according to any one of Items 1 to 3 or a pharmaceutically acceptable salt thereof for use in treating or preventing a disease selected from the group consisting of autoimmune diseases, allergic diseases, dry eye, fibrosis, cancers, metabolic disease, ischemia, cardiomyopathy, hypertension, and periodontal disease.

[Item 13]

A commercial package comprising a pharmaceutical composition according to Item 4 and a package insert concerning the pharmaceutical composition describing that the pharmaceutical composition can be used for treating or preventing a disease selected from the group consisting of autoimmune diseases, allergic diseases, dry eye, fibrosis, cancers, metabolic disease, ischemia, cardiomyopathy, hypertension, and periodontal disease.

[Item 14]

A kit comprising a pharmaceutical composition according to Item 4 and a package insert concerning the pharmaceutical composition describing that the pharmaceutical composition can be used for treating or preventing a disease selected from the group consisting of autoimmune diseases, allergic diseases, dry eye, fibrosis, cancers, metabolic disease, ischemia, cardiomyopathy, hypertension, and periodontal disease.

[Item 15]

A crystalline form of a compound of Formula (1):

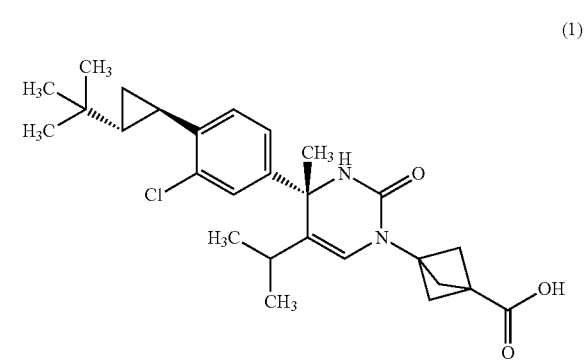 [SMILES: CC(C)C1=CN(C23CC(C(=O)O)(C2)C3)C(=O)N[C@@]1(C)c1ccc([C@@H]2C[C@H]2C(C)(C)C)c(Cl)c1]

(1)

showing a powder X-ray diffraction pattern having any three or more peaks selected from the group consisting of 7.4±0.2°, 9.9±0.2°, 10.5±0.2°, 11.4±0.2°, 11.6±0.2°, 13.4±0.2°, 14.2±0.2°, 17.4±0.2°, 18.3±0.2°, 18.7±0.2°, and 19.4±0.2° of the diffraction angle (2θ) measured with CuKα radiation.

[Item 16]

A monohydrate of a compound of Formula (1):

(1)

[Item 17]

A crystalline form of a monohydrate of a compound of Formula (1):

(1)

showing a powder X-ray diffraction pattern having any three or more peaks selected from the group consisting of 4.2±0.2°, 9.7±0.2°, 13.7±0.2°, 14.0±0.2°, 15.2±0.2°, 15.4±0.2°, 16.9±0.2°, 18.8±0.2°, 20.5±0.2°, 21.9±0.2°, and 22.4±0.2° of the diffraction angle (2θ) measured with CuKα radiation.

BRIEF DESCRIPTION OF DRAWINGS

FIG. 1 shows a powder X-ray diffraction pattern of Crystalline Form A. The vertical axis shows diffraction intensity (cps: counts per second), and the horizontal axis shows diffraction angle 2θ (°).

FIG. 2 shows a differential scanning calorimetry (DSC) curve of Crystalline Form A. The vertical axis shows Heat Flow (Watt per gram), and the horizontal axis shows temperature (° C.).

FIG. 3 shows a powder X-ray diffraction pattern of Crystalline Form B. The vertical axis shows diffraction intensity (cps: counts per second), and the horizontal axis shows diffraction angle 2θ (°).

FIG. 4 shows a DSC curve of Crystalline Form B. The vertical axis shows Heat Flow (Watt per gram), and the horizontal axis shows temperature (° C.).

FIG. 5 shows a powder X-ray diffraction pattern of Crystalline Form C. The vertical axis shows diffraction intensity (cps: counts per second), and the horizontal axis shows diffraction angle 2θ (°).

FIG. 6 shows a DSC curve of Crystalline Form C. The vertical axis shows Heat Flow (Watt per gram), and the horizontal axis shows temperature (° C.).

FIG. 7 shows a powder X-ray diffraction pattern of Crystalline Form D. The vertical axis shows diffraction intensity (cps: counts per second), and the horizontal axis shows diffraction angle 2θ (°).

FIG. 8 shows a TG-DTA curve of Crystalline Form D. The upper part of vertical axis shows weight (gram), the lower part of vertical axis shows temperature (° C.), and the horizontal axis shows temperature (° C.).

FIG. 9 shows a DSC curve of Crystalline Form D. The vertical axis shows Heat Flow (Watt per gram), and the horizontal axis shows temperature (° C.).

FIG. 10 shows a powder X-ray diffraction pattern of Crystalline Form E. The vertical axis shows diffraction intensity (cps: counts per second), and the horizontal axis shows diffraction angle 2θ (°).

FIG. 11 shows a TG-DTA curve of Crystalline Form E. The upper part of vertical axis shows weight (gram), the lower part of vertical axis shows temperature (° C.), and the horizontal axis shows temperature (° C.).

FIG. 12 shows a DSC curve of Crystalline Form E. The vertical axis shows Heat Flow (Watt per gram), and the horizontal axis shows temperature (° C.).

DESCRIPTION OF EMBODIMENTS

Definitions of terms used herein are shown as follows.

"A compound of Formula (1)" and "a compound of Formula (2)" are also optionally referred to as "Compound (1)" and "Compound (2)", respectively. "Compound (1) or Compound (2)(,) or a pharmaceutically acceptable salt thereof" means Compound (1) or Compound (2) or a pharmaceutically acceptable salt of Compound (1) or Compound (2), and is intended to include any of pharmaceutically acceptable salts of Compound (1) and pharmaceutically acceptable salts of Compound (2).

The term "pharmaceutically acceptable salt" may be any salts without excess toxicity known in the art. Specifically, it includes, for example, salts with inorganic acids, salts with organic acids, salts with inorganic bases, and salts with organic bases. Various forms of pharmaceutically acceptable salts are well known in the art and are listed, for example, in the following references:

(a) Berge et al., J. Pharm. Sci., 66, p 1-19 (1977);
(b) Stahl et al., "Handbook of Pharmaceutical Salts: Properties, Selection, and Use" (Wiley-VCH, Weinheim, Germany, 2002);
(c) Paulekuhn et al., J. Med. Chem., 50, p 6665-6672 (2007).

According to known methods, Compound (1) or Compound (2) may be reacted with an inorganic acid, organic acid, inorganic base, or organic base to give each pharmaceutically acceptable salt thereof.

Such salts with inorganic acids include, for example, salts with hydrofluoric acid, hydrochloric acid, hydrobromic acid, hydroiodic acid, nitric acid, phosphoric acid, and sulfuric acid. Preferable salts include salts with hydrochloric acid, nitric acid, sulfuric acid, phosphoric acid, and hydrobromic acid.

Such salts with organic acids include, for example, salts with acetic acid, adipic acid, alginic acid, 4-aminosalicylic acid, anhydromethylenecitric acid, benzoic acid, benzenesulfonic acid, camphor acid, camphor-10-sulfonic acid, carbonic acid, citric acid, edetic acid, ethane-1,2-disulfonic acid, dodecylsulfonic acid, ethanesulfonic acid, fumaric acid, glucoheptonic acid, gluconic acid, glucuronic acid, glucoheptonic acid, glycollylarsanilic acid, hydroxynaphthoic acid, 2-hydroxy-1-ethanesulfonic acid, lactic acid, lactobionic acid, malic acid, maleic acid, mandelic acid, methanesulfonic acid, methylsulfuric acid, methylnitric acid, methylenebis(salicylic acid), galactaric acid, naphthalene-2-sulfonic acid, 2-naphthoic acid, 1,5-naphthalenedisulfonic acid, oleic acid, oxalic acid, pamoic acid, pantothenic acid, pectic acid, picric acid, propionic acid, polygalacturonic acid, salicylic acid, stearic acid, succinic acid, tannic acid, tartaric acid, teoclic acid, thiocyanic acid, trifluoroacetic acid, p-toluenesulfonic acid, undecanoic acid, asparaginic acid, and glutamic acid. Preferable salts include salts with oxalic acid, maleic acid, citric acid, fumaric acid, lactic acid, malic acid, succinic acid, tartaric acid, acetic acid, trifluoroacetic acid, benzoic acid, glucuronic acid, oleic acid, pamoic acid, methanesulfonic acid, benzenesulfonic acid, p-toluenesulfonic acid, and 2-hydroxy-1-ethanesulfonic acid.

Such salts with inorganic bases include, for example, salts with lithium, sodium, potassium, magnesium, calcium, barium, aluminum, zinc, bismuth, and ammonium. Preferable salts include salts with sodium, potassium, calcium, magnesium, and zinc.

Such salts with organic bases include, for example, salts with arecoline, betaine, choline, clemizole, ethylenediamine, N-methylglucamine, N-benzylphenethylamine, tris(hydroxymethyl)methylamine, arginine, and lysine. Preferable salts include salts with tris(hydroxymethyl)methylamine, N-methylglucamine, and lysine.

Compound (1) or Compound (2) or a pharmaceutically acceptable salt thereof may exist in a solvate form.

The term "solvate" means Compound (1) or Compound (2) or a pharmaceutically acceptable salt thereof coordinate with a solvent molecule and includes a hydrate. Such a solvate is preferably a pharmaceutically acceptable solvate and includes hydrates, ethanolates, and solvates with dimethylsufoxide of Compound (1) or Compound (2) or a pharmaceutically acceptable salt thereof.

Specifically, such a solvate includes a hemihydrate, monohydrate, dihydrate, or monoethanolate of Compound (1) or Compound (2), or a monohydrate of a hydrochloride salt or a 2/3 ethanolate of a dihydrochloride salt of Compound (1) or Compound (2). A preferable solvate includes a monohydrate of Compound (1). Such a solvate may be obtained according to known methods.

Compound (1) or Compound (2) or a pharmaceutically acceptable salt thereof may be labelled with an isotope atom such as $^2$H, $^3$H, $^{14}$C, and $^{35}$S.

For example, any hydrogen atoms of Compound (1) or Compound (2) include protium $^1$H (H), deuterium $^2$H (D), and tritium $^3$H (T).

Compound (1) or Compound (2), or a pharmaceutically acceptable salt thereof is preferably Compound (1) or Compound (2), or a pharmaceutically acceptable salt thereof, substantially purified. More preferable one is Compound (1) or Compound (2), or a pharmaceutically acceptable salt thereof, having 80% or more of purity.

A preferable crystalline form of Compound (1) or Compound (2), or a pharmaceutically acceptable salt thereof, includes a crystalline form of Compound (1) showing a powder X-ray diffraction pattern having at least 3 peaks, for example, at least 3, 4, or 5 peaks, at any of 7.4±0.2°, 9.9±0.2°, 10.5±0.2°, 11.4±0.2°, 11.6±0.2°, 13.4±0.2°, 14.2±0.2°, 17.4±0.2°, 18.3±0.2°, 18.7±0.2°, or 19.4±0.2° of the diffraction angle (2θ) measured with CuKα radiation. A more preferable crystalline form of Compound (1) may show a powder X-ray diffraction pattern having peaks at 7.4±0.2°, 9.9±0.2°, and 13.4±0.2° of 2θ. A further preferable crystalline form of Compound (1) may show a powder X-ray diffraction pattern having peaks at 7.4±0.2°, 9.9±0.2°, 13.4±0.2°, 18.7±0.2°, and 19.4±0.2° of 2θ.

Another preferable crystalline form of Compound (1) or Compound (2), or a pharmaceutically acceptable salt thereof, includes a crystalline form of a monohydrate of Compound (1) showing a powder X-ray diffraction pattern having at least 3 peaks, for example, at least 3, 4, or 5 peaks, at any of 4.2±0.2°, 9.7±0.2°, 13.7±0.2°, 14.0±0.20, 15.2±0.2°, 15.4±0.2°, 16.9±0.2°, 18.8±0.2°, 20.5±0.2°, 21.9±0.2°, or 22.4±0.2° of the diffraction angle (2θ) measured with CuKα radiation. A more preferable crystalline form of a monohydrate of Compound (1) may show a powder X-ray diffraction pattern having peaks at 4.2±0.2°, 9.7±0.2°, and 16.9±0.2° of 2θ. A further preferable crystalline form of a monohydrate of Compound (1) may show a powder X-ray diffraction pattern having peaks at 4.2±0.2°, 9.7±0.2°, 13.7±0.2°, 15.2±0.2°, and 16.9±0.2° of 2θ.

The error range of the diffraction angle (2θ) in a powder X-ray diffraction pattern is preferably ±0.20, more preferably ±0.1, and further preferably ±0.05°.

According to known methods in the art of pharmaceutical formulations, a pharmaceutical composition herein may be prepared by, for example, mixing Compound (1) or Compound (2) or a pharmaceutically acceptable salt thereof with at least one or more pharmaceutically acceptable carrier(s) in an appropriate amount. The content (also referred to as "a therapeutically effective amount" herein) of Compound (1) or Compound (2) or a pharmaceutically acceptable salt thereof in the pharmaceutical composition varies depending on dosage forms and doses and is, for example, 0.1 to 100% by weight of the composition.

A dosage form of Compound (1) or Compound (2) or a pharmaceutically acceptable salt thereof includes an oral preparation such as tablets, capsules, granules, powders, lozenges, syrups, emulsions, and suspensions and a parenteral preparation such as external preparations, suppositories, injections, eye drops, nasal preparations, and pulmonary preparations.

The term "pharmaceutically acceptable carrier" includes various conventional organic or inorganic carrier substances for formulation materials such as excipients, disintegrants, binders, fluidizers, and lubricants in solid formulations; solvents, solubilizing agents, suspending agents, tonicity agents, buffers, and soothing agents in liquid formulations; and bases, emulsifying agents, wetting agents, stabilizers, stabilizing agents, dispersants, plasticizers, pH regulators, absorption promoters, gelators, preservatives, fillers, solubilizers, solubilizing agents, and suspending agents in semisolid formulations. A preserving agent, an antioxidant agent, a colorant, or a sweetening agent may also be optionally used as an additive.

Such an "excipient" includes, for example, lactose, white soft sugar, D-mannitol, D-sorbitol, cornstarch, dextrin, microcrystalline cellulose, crystalline cellulose, carmellose, carmellose calcium, sodium carboxymethyl starch, low substituted hydroxypropyl cellulose, and gum arabic.

Such a "disintegrant" includes, for example, carmellose, carmellose calcium, carmellose sodium, sodium carboxymethyl starch, croscarmellose sodium, crospovidone, low substituted hydroxypropyl cellulose, hydroxypropyl methylcellulose, and crystalline cellulose.

Such a "binder" includes, for example, hydroxypropyl cellulose, hydroxypropyl methylcellulose, povidone, crystalline cellulose, white soft sugar, dextrin, starch, gelatin, carmellose sodium, and gum arabic.

Such a "fluidizer" includes, for example, light anhydrous silicic acid and magnesium stearate.

Such a "lubricant" includes, for example, magnesium stearate, calcium stearate, and talc.

Such a "solvent" includes, for example, purified water, ethanol, propyleneglycol, macrogol, sesame oil, corn oil, and olive oil.

Such a "solubilizing agent" includes, for example, propyleneglycol, D-mannitol, benzyl benzoate, ethanol, triethanolamine, sodium carbonate, and sodium citrate.

Such a "suspending agent" includes, for example, benzalkonium chloride, carmellose, hydroxypropyl cellulose, propyleneglycol, povidone, methylcellulose, and glyceryl monostearate.

Such a "tonicity agent" includes, for example, glucose, D-sorbitol, sodium chloride, and D-mannitol.

Such a "buffer" includes, for example, sodium hydrogen phosphate, sodium acetate, sodium carbonate, and sodium citrate.

Such a "soothing agent" includes, for example, benzyl alcohol.

Such a "base" includes, for example, water, animal or vegetable oils such as olive oil, corn oil, arachis oil, sesame oil, and castor oil, lower alcohols such as ethanol, propanol, propylene glycol, 1,3-butylene glycol, and phenol, higher fatty acids and esters thereof, waxes, higher alcohols, polyalcohols, hydrocarbons such as white petrolatum, liquid paraffin, and paraffin, hydrophilic petrolatum, purified lanolin, absorptive ointment, hydrous lanolin, hydrophilic ointment, starch, pullulan, gum arabic, tragacanth gum, gelatin, dextran, cellulose derivatives such as methylcellulose, carboxymethylcellulose, hydroxyethyl cellulose, and hydroxypropyl cellulose, synthetic polymers such as carboxyvinyl polymers, sodium polyacrylate, polyvinyl alcohol, and polyvinylpyrrolidone, propylene glycol, macrogol such as macrogol 200 to 600, and a combination of any two or more of them.

Such a "preserving agent" includes, for example, ethyl parahydroxybenzoate, chlorobutanol, benzyl alcohol, sodium dehydroacetate, and sorbic acid.

Such an "antioxidant agent" includes, for example, sodium sulfite and ascorbic acid.

Such a "colorant" includes, for example, food dye such as Food Red No. 2 and No. 3, and Food Yellow No. 4 and No. 5, and β-carotene.

Such a "sweetening agent" includes, for example saccharin sodium, dipotassium glycyrrhizate, and aspartame.

A pharmaceutical composition herein may be administered orally or parenterally such as locally, rectally, intravenously, intramuscularly, and subcutaneously to mammals other than human such as mice, rats, hamsters, guinea pigs, rabbits, cats, dogs, pigs, cattle, horses, sheep, and monkeys as well as human. A dose may vary depending on subjects to be administered, diseases, symptoms, dosage forms, routes of administration, etc. For example, in oral administration to an adult patient, the dose of Compound (1) or Compound (2), the active ingredient, ranges generally from about 0.01 mg to about 1 g per day, which may be administered once or several times in a divided amount.

A kit such as kits for administration, treatment, and/or prevention, a package such as packaged goods, and a set and/or case of medicine which comprises a pharmaceutical composition comprising Compound (1) or Compound (2) or a pharmaceutically acceptable salt thereof as the active ingredient or active agent and a written matter concerning the composition indicating that the composition may or should be used for treatment and/or prevention are also useful. Such a kit, package, and set of medicine may comprise one or more containers filled with the pharmaceutical composition or one or more active ingredients and other drugs or medicines (or ingredients) used for the composition. Examples of such a kit, package, and set of medicine include commercial kits, commercial packages, and commercial medicine set for appropriate use in the treatment and/or prevention of intended diseases. The written matter comprised in such a kit, package, and set of medicine includes a cautionary note or package insert in the form designated by the government organization that regulates manufactures, use, or sales of pharmaceutical or biological products which ensures an approval by the government organization on manufactures, use, or sales of products concerning administration to humans. The kit, package, and set of medicine may include packaged products as well as structures configured for appropriate administration steps and configured sc as to be able to achieve more preferable medical treatment and/or prevention including treatment and/or prevention of intended diseases.

Compound (1) or Compound (2) or a pharmaceutically acceptable salt thereof has RORγ antagonism and is useful for an RORγ antagonist.

The term "having RORγ antagonist activity", "having RORγ antagonism", or "antagonizing RORγ" means that the function of RORγ is antagonized, preferably specifically antagonized, to disappear or reduce its activity, and includes, for example, antagonizing, preferably specifically antagonizing, the function of RORγ according to the conditions described in Test Example 1 below.

The term "RORγ antagonist" means any substances that antagonize the function of RORγ, preferably any substances that specifically antagonize the function of RORγ.

The term "RORγ" is preferably "human RORγ".

Compound (1) or Compound (2) or a pharmaceutically acceptable salt thereof has RORγ antagonism, and is expected to be effective against diseases that involve the function of RORγ.

Specifically, Compound (1) or Compound (2) or a pharmaceutically acceptable salt thereof is expected to be useful for treating or preventing a disease selected from the group consisting of autoimmune diseases, allergic diseases, dry eye, fibrosis, cancers, metabolic disease, ischemia, cardiomyopathy, hypertension, and periodontal disease.

The term "autoimmune diseases" means a generic name of diseases where an immune system of a subject overreacts to and attacks even normal cells and tissues thereof to cause symptoms, and includes, specifically, rheumatoid arthritis, psoriasis, inflammatory bowel diseases such as Crohn's disease and ulcerative colitis, multiple sclerosis, systemic lupus erythematosus (SLE), Behcet's disease, sarcoidosis, Harada disease, ankylosing spondylitis, uveitis, polymyalgia rheumatica, type I diabetes, graft-versus-host disease, alopecia areata, and vitiligo.

The term "allergic diseases" means diseases derived from the condition where an immune reaction excessively occurs against a certain antigen, and includes, specifically, atopic dermatitis, allergic rhinitis such as pollen allergy, allergic conjunctivitis, allergic gastroenteritis, asthma such as bronchial asthma and infantile asthma, food allergy, medication allergy, and hives.

The term "fibrosis" means a condition with increased fibroconnective tissues, and includes, specifically, lung fibrosis and primary biliary cirrhosis.

The term "cancers" includes, specifically, malignant melanoma and prostate cancer.

The term "metabolic disease" means a disease caused by abnormality of metabolic turnover or a disease which includes metabolic abnormality as an element that constitutes pathogenesis, and includes, for example, diabetes such as type I diabetes and type II diabetes, hepatic steatosis, and non-alcoholic fatty liver disease.

The term "treating" used herein also includes ameliorating symptoms, preventing from becoming severe, maintaining remission, preventing exacerbation, and preventing relapse.

The term "preventing" used herein means suppressing pathogenesis of symptoms.

Compound (1) or Compound (2), or a pharmaceutically acceptable salt thereof, has the following demonstrated properties:
(i) high metabolic stability referring to Test Example 2;
(ii) beneficial pharmacokinetic profile, including favorable plasma half-life referring to Test Example 5;
(iii) low potency to induce drug metabolic enzymes such as CYP3A4 referring to Test Example 3;
(iv) favorably high solubility referring to Test Example 4; and
(v) sustained and/or potent pharmacological effect referring to Test Examples 6 and 7.

These properties render Compound (1) or Compound (2), or a pharmaceutically acceptable salt thereof, particularly advantageous. For example, Compound (1) or Compound (2), or a pharmaceutically acceptable salt thereof:
(i) exhibits sustained pharmacological effects that may allow for lower dosing frequency or longer dosing intervals, which may favorably impact patient compliance and thereby improve overall therapeutic outcome;
(ii) exhibits a low induction of drug metabolic enzymes such as CYP3A4, which may result in decreased metabolism of concomitant drugs metabolized by such enzymes, and thus the present compound may be more suitable for patients simultaneously taking multiple therapeutic drugs; and
(iii) may have a favorable oral bioavailability based upon high solubility and, thus, may express dose-dependent increase in plasma concentration even in high dosing amount and/or exhibit small individual variability in absorption process.

As long as an embodiment disclosed herein is compatible with another embodiment disclosed in another portion of the description, any two or more combinations of these embodiments are also intended to be included in the invention.

A method of preparing Compound (1) or Compound (2) or a pharmaceutically acceptable salt thereof is illustrated in the examples as below. A method of preparing Compound (1) or Compound (2) or a pharmaceutically acceptable salt thereof, however, is not intended to be limited thereto.

Each compound obtained in each step may be isolated and/or purified by known methods such as distillation, recrystallization, and column chromatography, if necessary, but each reaction may optionally proceed to a sequential step without isolation and/or purification.

The room temperature herein means a temperature under no control, and includes 1° C. to 40° C. as one embodiment.

EXAMPLES $^1$H-NMR spectra were measured with tetramethylsilane as an internal standard in $CDCl_3$ or DMSO-$d_6$ and all δ values are shown in ppm. Symbols in spectral data mean as follows.

s: singlet
d: doublet
t: triplet
q: quartet
dd: double doublet
ddd: double double doublet
brs: broad singlet
m: multiplet
J: coupling constant Example 1

Synthesis of 3-{(S)-4-[4-((1R,2R)-2-tert-butyl-cyclopropyl)-3-chloro-phenyl]-5-isopropyl-4-methyl-2-oxo-3,4-dihydro-2H-pyrimidin-1-yl}bicyclo[1.1.1]pentane-1-carboxylic acid Step 1

(S)-2-Methyl-propane-2-sulfinic acid [1-(4-bromo-3-chloro-phenyl)-eth-(E)-yliden]-amide

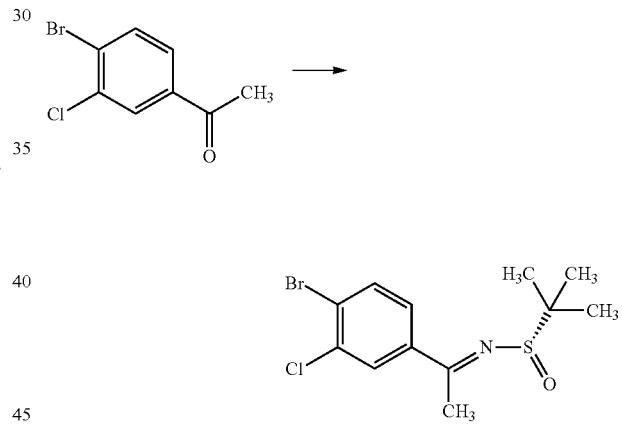

1-(4-Bromo-3-chloro-phenyl)-ethanone (60.0 g) and (S)-(−)-2-methyl-propane-2-sulinic acid amide (37.3 g) were mixed in cyclopentylmethyl ether (257 mL). To the reaction solution was added tetraethyl orthotitanate (70.3 g), and the reaction solution was stirred at 100° C. for 5 hours. To the reaction solution was added 40 w/v % aqueous ammonium lactate solution (308 mL) at room temperature, and the mixture was extracted with ethyl acetate. The resulting organic layer was washed with water and brine, and then dried over magnesium sulfate. Magnesium sulfate was removed through a filter, and then the filtrate was concentrated under reduced pressure. The resulting residue was purified by silica gel column chromatography (ethyl acetate: n-hexane=1:4→2:3). The resulting residue was solidified with n-hexane/diethyl ether and the precipitated solid was filtered to give the title compound (70.6 g).

$^1$H-NMR (400 MHz, $CDCl_3$) 1.30 (s, 9H), 2.72 (s, 3H), 7.58 (dd, J=8.55, 2.08 Hz, 1H), 7.66 (d, J=8.55 Hz, 1H), 7.91 (d, J=2.08 Hz, 1H)

Step 2

(R)-3-(4-Bromo-3-chloro-phenyl)-2-isopropyl-3-((S)-2-methyl-propane-2-sulfinylamino)butyric acid methyl ester Step 3

(S)-2-Methyl-propane-2-sulfinic acid {(R)-1-(4-bromo-3-chloro-phenyl)-2-hydroxymethyl-1,3-dimethyl-butyl}amide

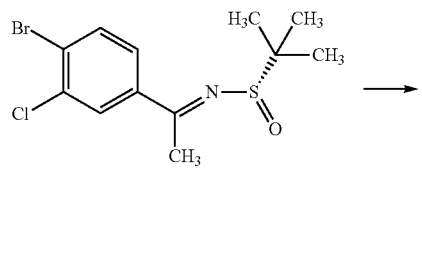
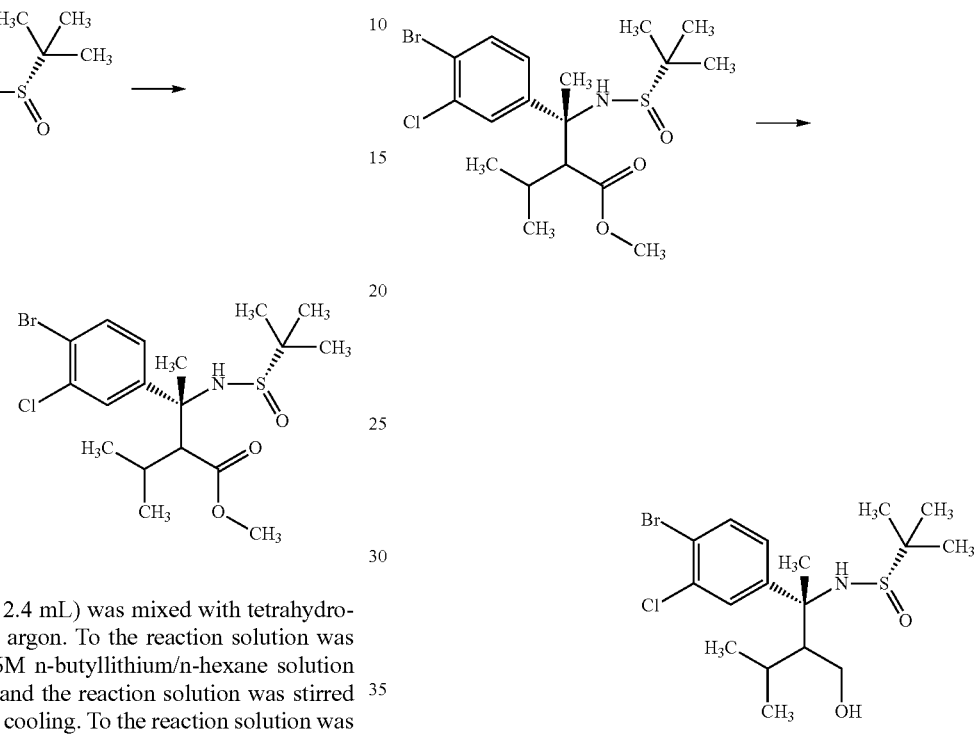

Diisopropylamine (12.4 mL) was mixed with tetrahydrofuran (89.1 mL) under argon. To the reaction solution was added dropwise a 2.66M n-butyllithium/n-hexane solution (33.5 mL) at −78° C., and the reaction solution was stirred for 5 minutes under ice cooling. To the reaction solution was added dropwise a mixed solution of 3-methyl-butyric acid methyl ester (11.7 mL) in tetrahydrofuran (44.5 mL), and the reaction solution was stirred at −78° C. for 1 hour. To the reaction solution was added dropwise a mixed solution of (S)-2-methyl-propane-2-sulfinic acid [1-(4-bromo-3-chloro-phenyl)-eth-(E)-yliden]-amide (15.0 g) in tetrahydrofuran (44.5 mL), and the reaction solution was stirred for 2 hours. To the reaction solution was added a mixed solution of acetic acid (5.1 mL) in tetrahydrofuran (25.4 mL), and the mixture was stirred under room temperature. To the reaction solution was added 1M aqueous monosodium citrate solution (100 ml), and the layers were separated. The resulting organic layer was washed with water (100 mL, twice). Combined aqueous layers were extracted with ethyl acetate (100 mL, twice). Combined organic layers were washed with 1M aqueous monosodium citrate solution (100 ml), water (100 mL, twice), and brine, and then dried over magnesium sulfate. Magnesium sulfate was removed through a filter, and then the filtrate was concentrated under reduced pressure. The resulting residue was purified by silica gel column chromatography (ethyl acetate:n-hexane=1:4→3:2) to give the title compound (18.0 g).

$^1$H-NMR (400 MHz, CDCl$_3$) 0.76 (d, J=6.94 Hz, 7.2H), 0.93 (d, J=6.94 Hz, 1.8H), 0.95 (d, J=6.94 Hz, 1.8H), 1.00 (d, J=6.94 Hz, 1.2H), 1.26 (s, 5.4H), 1.34 (s, 3.6H), 1.74-1.81 (m, 0.4H), 1.87 (s, 1.2H), 1.88 (s, 1.81), 2.04-2.13 (m, 0.6H), 2.46 (d, J=3.93 Hz, 0.4H), 2.80 (d, J=3.93 Hz, 0.6H), 3.60 (s, 1.8H), 3.70 (s, 1.2H), 5.13 (s, 0.6H), 5.42 (s, 0.4H), 7.17-7.21 (m, 1H), 7.54-7.59 (m, 2H)

(R)-3-(4-Bromo-3-chloro-phenyl)-2-isopropyl-3-((S)-2-methyl-propane-2-sulfinylamino)butyric acid methyl ester (18.0 g) was mixed in toluene (39.7 mL) under argon. To the reaction solution was added dropwise an 1M diisobutylaluminum hydride/toluene solution (59.1 mL) at −78° C., and the reaction solution was stirred at −78° C. for 2 hours. Then, the reaction solution was gradually warmed to 0° C., and then stirred for 30 minutes. To the reaction solution was added methanol (39 mL) at −78° C. To the reaction solution were added 30 w/v % aqueous L-tartaric acid solution (75 mL) and ethyl acetate (300 mL) under ice cooling, and the layers were separated. The resulting aqueous layer was extracted with ethyl acetate (100 mL). Combined organic layers were washed with 30 w/v % aqueous L-tartaric acid solution (80 mL, twice), water (80 mL, twice), and brine, and then dried over sodium sulfate. Sodium sulfate was removed through a filter, and then the filtrate was concentrated under reduced pressure. The resulting residue was azeotroped with toluene to give a crude product of the title compound (18.5 g).

$^1$H-NMR (400 MHz, CDCl$_3$) 0.70 (d, J=6.94 Hz, 1.8H), 0.76 (d, J=6.94 Hz, 1.8H), 0.79 (d, J=6.94 Hz, 1.2H), 0.83 (d, J=6.94 Hz, 1.2H), 1.15 (s, 5.4H), 1.30 (s, 3.6H), 1.56-1.59 (m, 0.4H), 1.71-1.82 (m, 1H), 1.95 (s, 1.8H), 1.98 (s, 1.2H), 2.04-2.08 (m, 0.6H), 3.86-4.13 (m, 2H), 5.13 (s, 0.6H), 5.99 (s, 0.4H), 7.16-7.21 (m, 1H), 7.54-7.58 (m, 2H)

Step 4

(R)-3-Amino-3-(4-bromo-3-chloro-phenyl)-2-isopropyl-butan-1-ol

Step 5

3-{3-[(R)-1-(4-Bromo-3-chloro-phenyl)-2-hydroxymethyl-1,3-dimethyl-butyl]ureido}bicyclo[1.1.1]pentane-1-carboxylic acid methyl ester

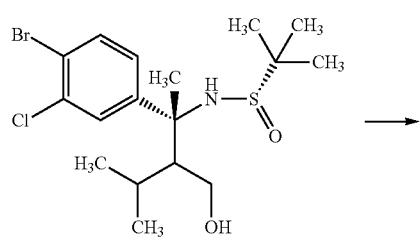

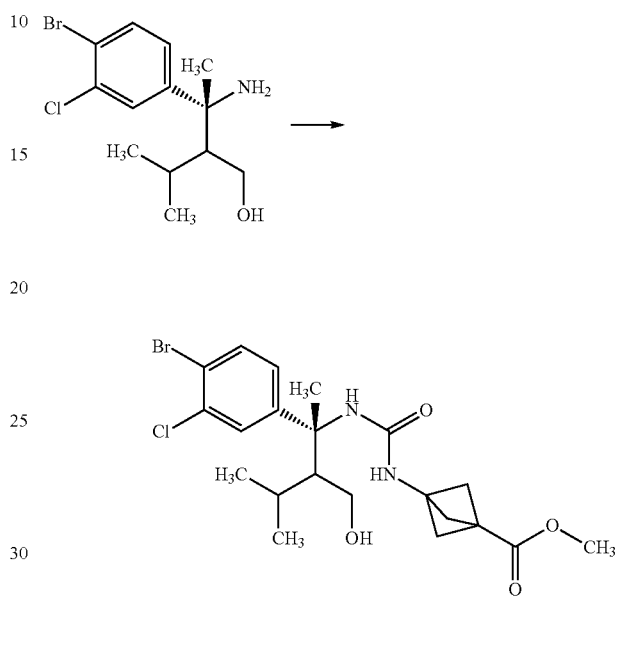

(S)-2-Methyl-propane-2-sulfinic acid {(R)-1-(4-bromo-3-chloro-phenyl)-2-hydroxymethyl-1,3-dimethyl-butyl}amide (18.5 g) was mixed in methanol (79.5 mL). To the reaction solution was added dropwise a 2M hydrogen chloride/methanol solution (39.8 mL) under ice cooling, and the reaction solution was stirred for 1.5 hours. The reaction solution was concentrated under reduced pressure, and to the residue was added 10 w/v % aqueous sodium carbonate solution (50.0 mL). The reaction solution was extracted with ethyl acetate (80 mL). The resulting aqueous layer was extracted with ethyl acetate (twice). Combined organic layers were washed with a 10 w/v % aqueous sodium carbonate solution (50 mL), water (50 mL), and brine, and then dried over sodium sulfate. Sodium sulfate was removed through a filter, and then the resulting organic layer that was concentrated under reduced pressure was dried over magnesium sulfate. Magnesium sulfate was removed through a filter, and then the filtrate was concentrated under reduced pressure. The resulting residue was azeotroped with toluene to give a crude product of the title compound (15.7 g).

$^1$H-NMR (400 MHz, CDCl$_3$) 0.69 (d, J=6.94 Hz, 1.2H), 0.83 (d, J=6.94 Hz, 1.8H), 0.85 (d, J=6.94 Hz, 1.2H), 0.87 (d, J=6.94 Hz, 1.8H), 1.36-1.47 (m, 0.6H), 1.59 (s, 1.2H), 1.60 (s, 1.8H), 1.64 (ddd, J=5.32, 3.24, 2.31 Hz, 0.4H), 1.66-1.77 (m, 0.4H), 1.85 (ddd, J=8.79, 3.47, 2.31 Hz, 0.6H), 3.69 (dd, J=11.33, 3.47 Hz, 0.6H), 3.81 (dd, J=11.79, 5.32 Hz, 0.4H), 3.91 (dd, J=11.33, 8.79 Hz, 0.6H), 3.96 (dd, J=11.79, 3.47 Hz, 0.4H), 7.18-7.20 (m, 1H), 7.50 (d, J=2.31 Hz, 0.6H), 7.53 (d, J=2.31 Hz, 0.4H), 7.58 (d, J=6.70 Hz, 0.6H), 7.60 (d, J=6.70 Hz, 0.4H)

3-(Methoxycarbonyl)bicyclo[1.1.1]pentane-1-carboxylic acid (4.00 g) and toluene (47.0 mL) were mixed under nitrogen, and thereto were added diphenylphosphoryl azide (5.58 mL) and triethylamine (3.60 mL) at room temperature. The reaction solution was stirred at 120° C. for 50 minutes. The reaction solution was slowly added dropwise to a solution of (R)-3-amino-3-(4-bromo-3-chloro-phenyl)-2-isopropyl-butan-1-ol (9.77 g) in tetrahydrofuran (47.0 mL) over 15 minutes under ice cooling. The reaction solution was stirred at room temperature for 1 hour. To the reaction solution was added 10 w/v % aqueous citric acid solution (100 mL), and the layers were separated. The resulting organic layer was washed with water (60 mL). Combined aqueous layers were extracted with ethyl acetate (twice). Combined organic layers were washed with 10 w/v % aqueous citric acid solution (60 mL), water (60 mL), 10 w/v % aqueous sodium carbonate solution (60 mL), water (60 mL), and brine, and then dried over sodium sulfate. Sodium sulfate was removed through a filter, and then the filtrate was concentrated under reduced pressure. The resulting residue was purified by silica gel column chromatography (ethyl acetate:n-hexane=7:13→100:0) to give the title compound (8.34 g).

$^1$H-NMR (400 MHz, CDCl$_3$) 0.28 (d, J=6.94 Hz, 1.2H), 0.79 (d, J=6.94 Hz, 1.8H), 0.85 (d, J=6.94 Hz, 1.8H), 0.92 (d, J=6.94 Hz, 1.2H), 1.52-1.59 (m, 0.6H), 1.79-1.88 (m, 0.4H), 1.84 (s, 1.8H), 1.90 (s, 1.2H), 2.12-2.18 (m, 0.4H), 2.21-2.32 (m, 0.6H), 2.29 (s, 3.6H), 2.29 (s, 2.4H), 3.67 (s, 3H), 3.82-3.75 (m, 1.4H), 3.89-3.94 (m, 0.6H), 4.61 (s, 0.6H), 4.70 (s, 0.4H), 6.92 (s, 0.4H), 7.04 (s, 0.6H), 7.13-7.16 (m, 1H), 7.44 (d, J=2.31 Hz, 0.4H), 7.45 (d, J=2.08 Hz, 0.6H), 7.53 (d, J=8.55 Hz, 1H)

Step 6

3-[(S)-4-(4-Bromo-3-chloro-phenyl)-5-isopropyl-4-methyl-2-oxo-3,4-dihydro-2H-pyrimidin-1-yl]-bicyclo[1.1.1]pentane-1-carboxylic acid methyl ester

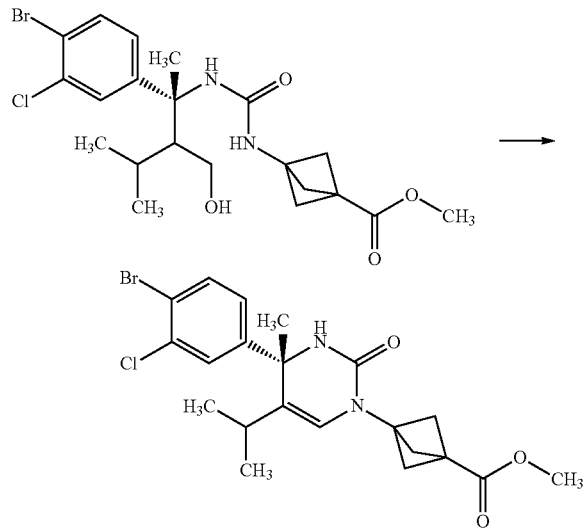

3-{3-[(R)-1-(4-Bromo-3-chloro-phenyl)-2-hydroxymethyl-1,3-dimethyl-butyl]ureido}bicyclo[1.1.1]pentane-1-carboxylic acid methyl ester (10.0 g) and chloroform (68.4 mL) were mixed under nitrogen, and thereto were added (diacetoxyiodo)benzene (6.06 g) and 2,2,6,6-tetramethylpiperidin-1-oxyl radical (0.267 g) at room temperature. The reaction solution was stirred at room temperature for 3.5 hours, and then thereto was added 10 w/w % aqueous sodium sulfite solution (50 mL) at room temperature. The layers were separated. The resulting aqueous layer was extracted with chloroform (twice). Combined organic layers were washed with water (50 mL) and brine, and then dried over sodium sulfate. Sodium sulfate was removed through a filter, and then the filtrate was concentrated under reduced pressure. The resulting residue was azeotroped with toluene. The resulting residue was mixed with toluene (213 mL), and then thereto was added pentafluoroaniline trifluoromethanesulfonate (0.307 g) at room temperature. The reaction solution was stirred under warming at 100° C. for 2 hours, and then thereto were added sodium sulfite (880 mg) and 10 w/v % aqueous sodium carbonate solution (50 mL) at room temperature. The layers were separated. The resulting aqueous layer was extracted with ethyl acetate (twice). Combined organic layers were washed with water (50 mL) and brine, and then dried over magnesium sulfate. Magnesium sulfate was removed through a filter, and then the filtrate was concentrated under reduced pressure. The resulting residue was purified by silica gel column chromatography (ethyl acetate:n-hexane=1:4→3:2). The resulting residue was solidified with n-hexane, and the precipitated solid was filtered to give the title compound (6.35 g).

$^1$H-NMR (400 MHz, CDCl$_3$) 0.72 (d, J=6.94 Hz, 3H), 1.06 (d, J=6.94 Hz, 3H), 1.70 (s, 3H), 1.81-1.92 (m, 1H), 2.47 (s, 6H), 3.71 (s, 3H), 4.69 (s, 1H), 5.85 (s, 1H), 7.20 (dd, J=8.32, 2.31 Hz, 1H), 7.51 (d, J=2.31 Hz, 1H), 7.58 (d, J=8.32 Hz, 1H)

Step 7

3-{(S)-4-[4-(2-tert-Butyl-cyclopropyl)-3-chloro-phenyl]-5-isopropyl-4-methyl-2-oxo-3,4-dihydro-2H-pyrimidin-1-yl}bicyclo[1.1.1]pentane-1-carboxylic acid methyl ester

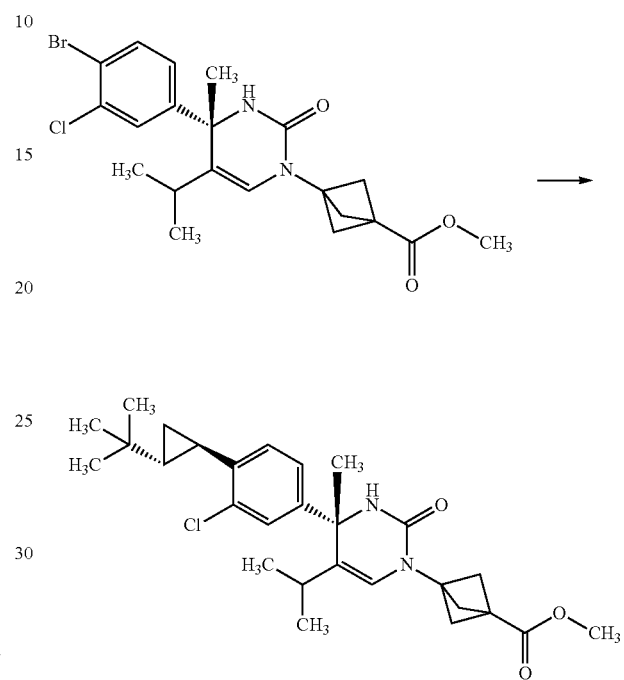

3-[(S)-4-(4-Bromo-3-chloro-phenyl)-5-isopropyl-4-methyl-2-oxo-3,4-dihydro-2H-pyrimidin-1-yl]-bicyclo[1.1.1]pentane-1-carboxylic acid methyl ester (5.23 g), potassium trans-2-tert-butyl-cyclopropyl-trifluoroborate (2.79 g), [1,1'-bis(di-tert-butyl-phosphino)ferrocene]palladium (II) dichloride (0.729 g), cesium carbonate (10.9 g), toluene (112 mL), and water (11.2 mL) were mixed under argon, and the mixture was stirred at 100° C. for 2 hours. To the reaction solution was added water (50 mL) at room temperature, and the layers were separated. The resulting aqueous layer was extracted with ethyl acetate (twice). Combined organic layers were washed with water (50 mL, twice) and brine, and then dried over magnesium sulfate. Then, thereto was added activated carbon, and the mixture was stirred at room temperature for 1 hour. Magnesium sulfate and activated carbon were removed through a filter, and then the filtrate was concentrated under reduced pressure. The resulting residue was purified by silica gel column chromatography (ethyl acetate:n-hexane=1:9→1:1). The resulting residue was mixed with methanol, and thereto was added activated carbon at room temperature. The activated carbon was removed through a filter, and then the filtrate was concentrated under reduced pressure. The resulting residue was purified by silica gel column chromatography (ethyl acetate:n-hexane=1:4→1:1) to give a diastereomer mixture of the title compound (3.70 g). Purification with a chiral preparative column gave the title compound (0.344 g).

Purification conditions for the preparative column are shown as follows.

Preparative apparatus: Recycling Preparative Liquid Chromatograph LC-92XX NEXT SERIES, Japan Analytical Industry Co., Ltd.
Column: Daicel CHIRALPAK IA 2.0 cmφ×25 cmL
130 Mobile phase: n-hexane:2-propanol=93:7
Flow rate: 10.0 mL/min
Detection: UV (220 nm)

Measurement with a chiral column showed 8.3 minutes of the retention time for the resulting title compound (7.6 minutes of the retention time for diastereomers of the title compound) with >99% de purity. Analytical conditions for the chiral column are shown as follows.
Measuring apparatus: HPLC system, Shimadzu Corporation,
High-Performance Liquid Chromatograph Prominence
Column: Daicel CHIRALPAK IA-3 0.46 cmφ×15 cmL
Column temperature: 40° C.
Mobile phase: n-hexane:2-propanol=93:7
Flow rate: 1.0 mL/min
Detection: UV (220 nm)

$^1$H-NMR (400 MHz, CDCl$_3$) 0.71 (d, J=7.09 Hz, 3H), 0.77-0.83 (m, 1H), 0.90-0.95 (m, 2H), 0.94 (s, 9H), 1.04 (d, J=7.09 Hz, 3H), 1.68 (s, 3H), 1.85-1.92 (m, 1H), 2.07-2.12 (m, 1H), 2.48 (s, 6H), 3.71 (s, 3H), 4.56 (s, 1H), 5.83 (s, 1H), 6.86 (d, J=8.31 Hz, 1H), 7.22 (dd, J=8.31, 1.96 Hz, 1H), 7.37 (d, J=1.96 Hz, 1H)

Step 8

3-{(S)-4-[4-((1R,2R)-2-tert-Butyl-cyclopropyl)-3-chloro-phenyl]-5-isopropyl-4-methyl-2-oxo-3,4-dihydro-2H-pyrimidin-1-yl}bicyclo[1.1.1]pentane-1-carboxylic acid

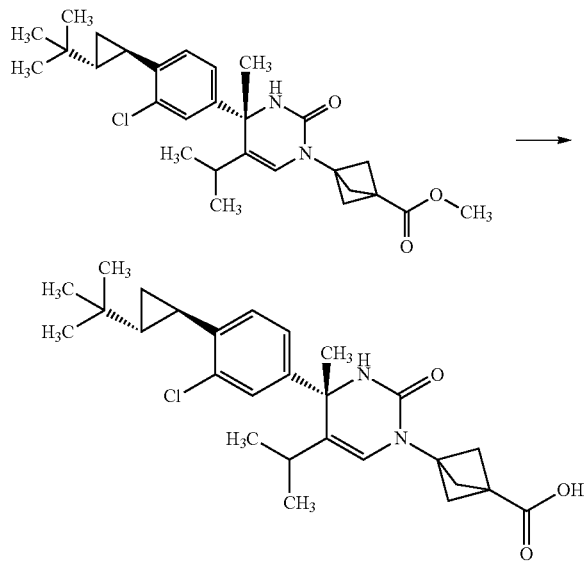

3-((S)-4-[4-(2-tert-Butyl-cyclopropyl)-3-chloro-phenyl]-5-isopropyl-4-methyl-2-oxo-3,4-dihydro-2H-pyrimidin-1-yl)bicyclo[1.1.1]pentane-1-carboxylic acid methyl ester (49.1 g), tetrahydrofuran (246 mL), and methanol (246 mL) were mixed under nitrogen, and thereto was added 2N aqueous sodium hydroxide solution (101 mL) at room temperature. The reaction solution was stirred at room temperature for 24 hours 30 minutes. The reaction solution was concentrated under reduced pressure, and to the residue were added water (400 mL) and 1N hydrochloric acid (250 mL). Then, thereto was added ethyl acetate (900 mL), and the layers were separated. The resulting aqueous layer was extracted with ethyl acetate (100 mL×2), and the organic layer was washed with water (250 mL) and brine, and then dried over sodium sulfate. Sodium sulfate was removed through a filter, and then the filtrate was concentrated under reduced pressure.

The resulting residue and acetonitrile (1000 mL) were mixed, and the mixture was stirred under warming at 85'C for 1 hour 15 minutes. Then, the mixture was stirred at room temperature for 13 hours 15 minutes, and then the resulting solid was filtered to give a crystal of the title compound (Crystalline Form A; 44.7 g).

A crystal of the title compound (29.7 mg) obtained in a similar manner, ethyl acetate (297 μL), and methanol (891 μL) were mixed. Solids were completely dissolved, and then solvents were concentrated under reduced pressure with a rotary evaporator, affording another crystal of the title compound (Crystalline Form B).

The above two crystals (10.0 mg each) obtained in a similar manner and isobutyl acetate (80 μL) were mixed, and the resulting slurry was stirred at room temperature for one week, and then the resulting solid was filtered to give another crystal of the title compound (Crystalline Form C), which was used for a seed crystal in the following procedures.

A crude crystal (2.00 g) obtained in a similar reaction to the above and isobutyl acetate (10 mL) were mixed and stirred at 90° C. After the crude crystal was completely dissolved, the seed crystal was added to the mixture at 47° C. of the internal temperature, and the mixture was stirred for 1 hour. At around 45° C. of the internal temperature, n-heptane (30 mL) was added to the reaction solution, and the mixture was stirred for 2 hours. The mixture was stirred at room temperature for 24 hours. The precipitated solid was filtered to give the title compound (Crystalline Form C; 1.7 g).

$^1$H-NMR (400 MHz, DMSO-D$_6$) 0.71 (d, J=6.94 Hz, 3H), 0.86-0.94 (m, 3H), 0.90 (s, 9H), 1.04 (d, J=6.94 Hz, 3H), 1.60 (s, 3H), 1.93-2.04 (m, 2H), 2.29 (s, 6H), 5.97 (s, 1H), 6.99 (d, J=7.86 Hz, 1H), 7.06 (s, 1H), 7.21 (dd, J=7.86, 1.85 Hz, 1H), 7.32 (d, J=1.85 Hz, 1H), 12.44 (s, 1H)

Absolute configurations of the asymmetric carbons of the title compound were determined by single-crystal X-ray structural analysis.

Synthesis of Intermediate 1

Potassium trans-2-tert-butyl-cyclopropyl-trifluoroborate

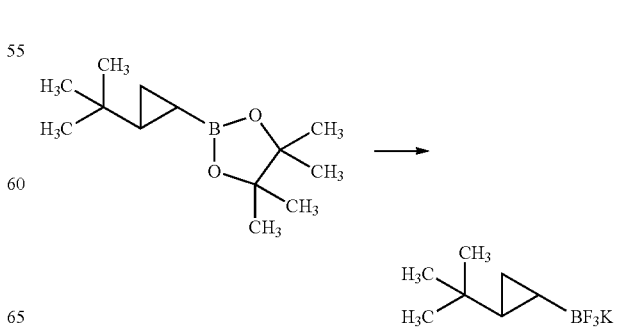

2-(trans-2-tert-Butyl-cyclopropyl)-4,4,5,5-tetramethyl-[1,3,2]dioxaborolane (8.03 g), methanol (200 mL), and water (40 mL) were mixed under nitrogen, and thereto was added potassium hydrogen fluoride (14 g) at room temperature. The reaction solution was stirred at 100° C. for 7 hours. Then, the solution was let stand at room temperature overnight, and then concentrated under reduced pressure. The resulting residue was azeotroped with toluene. The resulting residue and acetonitrile (120 mL) were mixed and stirred at 60° C. for 2 hours. The resulting solid was removed through a filter, and then the filtrate was concentrated under reduced pressure. The resulting residue and diethyl ether (80 mL) were mixed and stirred at room temperature. The precipitated solid was filtered to give the title compound (2.86 g).

$^1$H-NMR (400 MHz, DMSO-D$_6$) −0.94-−0.87 (m, 1H), −0.26-−0.23 (m, 2H), 0.25-0.30 (m, 1H), 0.73 (s, 9H)

Example 1A

Alternative synthesis of 3-{(S)-4-[4-((1R,2R)-2-tert-butyl-cyclopropyl)-3-chloro-phenyl]-5-isopropyl-4-methyl-2-oxo-3,4-dihydro-2H-pyrimidin-1-yl}bicyclo[1.1]pentane-1-carboxylic acid Step 1

(4S,5S)-2-((E)-3,3-Dimethyl-1-butenyl)-[1,3,2]dioxaborolane-4,5-dicarboxylic acid bis-dimethylamide

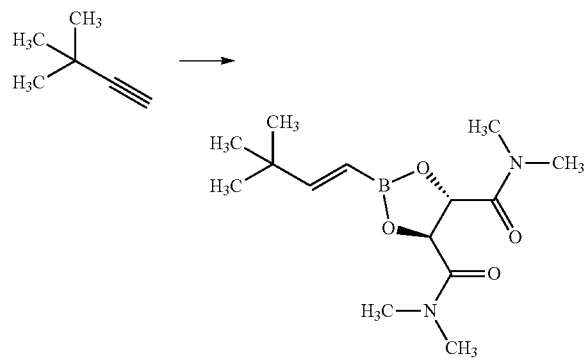

2M Dibromoborane-dimethyl sulfide complex/toluene solution (1250 mL) was mixed in toluene (1169 mL). To the reaction solution was added dropwise 3,3-dimethyl-1-butyne (338 mL) under water cooling for 45 minutes. The reaction solution was stirred under water cooling for 2.5 hours. The reaction solution was cooled by addition of ice into a water bath against delayed exotherm. The reaction solution was added dropwise to a mixed solution of 8N aqueous solution of potassium hydroxide (969 mL) and water (2922 mL) under ice cooling for 30 minutes. Toluene (1461 mL) and tetrahydrofuran (292 mL) were added to the aqueous layer, and thereto was added dropwise 6N hydrochloric acid (417 mL) under ice cooling for 20 minutes. Thereto was added sodium chloride (584 g), and the organic layer was separated.

The organic layer was mixed with toluene (1581 mL), and thereto was added L-tartaric acid-N,N,N',N'-tetramethylamide (562 g). The reaction solution was stirred for 2 hours under heating at 130° C. The organic layer was separated and concentrated under reduced pressure. Solids precipitated during the concentration were removed with a filter, and the filtrate was concentrated under reduced pressure to give a crude product of the title compound (599 g).

$^1$H NMR (400 MHz, DMSO-D$_6$) 1.00 (s, 9H), 2.87 (s, 6H), 3.06 (s, 6H), 5.30 (d, J=18.24 Hz, 1H), 5.44 (s, 2H), 6.64 (d, J=18.24 Hz, 1H)

Step 2

(1R,2R)-2-tert-Butylcyclopropylboronic acid

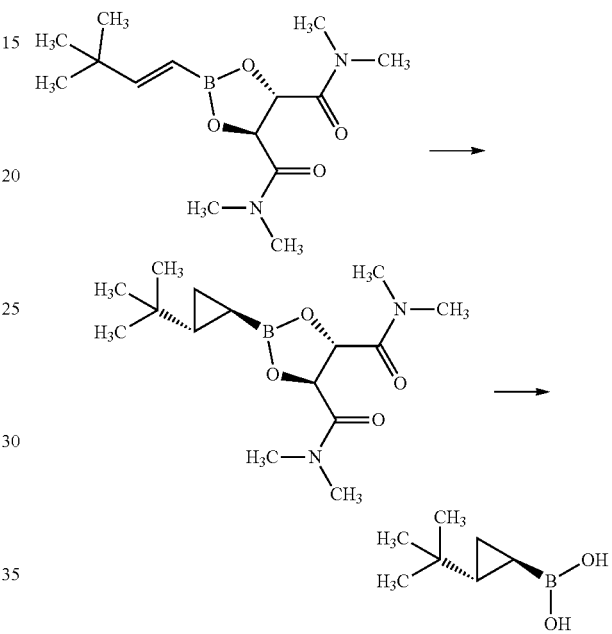

1.1M Diethylzinc/n-hexane solution (1892 mL) was mixed in methyl tert-butyl ether (838 mL) under argon. To the reaction solution was added dropwise chloroiodomethane (301 mL) under being cooled with dry ice-acetone for 35 minutes. The reaction solution was stirred under being cooled with dry ice-acetone for 30 minutes. Then, thereto was added L-tartaric acid-N,N,N',N'-tetramethylamide (70.8 g) under being cooled with dry ice-acetone, and the mixture was stirred for 20 minutes. To the reaction solution was added dropwise a mixed solution of (4S,5S)-2-((E)-3,3-dimethyl-1-butenyl)-[1,3,2]dioxaborolane-4,5-dicarboxylic acid bis-dimethylamide (222 g) in methyl tert-butyl ether (838 mL) under being cooled with dry ice-acetone for 30 minutes. The reaction solution was stirred under being cooled with dry ice-acetonitrile for 4.5 hours. Then, thereto was added a 30 w/v % aqueous solution of citric acid (1438 mL) under being cooled with dry ice-acetonitrile over 10 minutes. To the reaction solution were added ethyl acetate (1047 mL) and sodium chloride (335 g), and the organic layer was washed with water (1047 mL) and a 25 w/v % aqueous solution of sodium chloride (1047 mL) and then dried over magnesium sulfate. Magnesium sulfate was removed with a filter, and then the filtrate was concentrated under reduced pressure to give a crude product (82.6 g).

The resulting crude product (82.6 g) was mixed with an 8N aqueous solution of potassium hydroxide (87 mL) and water (150 mL). The reaction solution was added dropwise to 6N hydrochloric acid (117 mL) under ice cooling for 1 hour. The reaction solution was stirred under ice cooling for 1 hour. The precipitated solid was filtered to give the title compound (68.8 q).

$^1$H NMR (400 MHz, DMSO-D$_6$) –0.46 (td, J=5.98, 9.27 Hz, 1H), 0.30-0.37 (m, 2H), 0.70-0.82 (m, 1H), 0.79 (s, 9H), 12.94 (br s, 2H)

Step 3

Methyl 4-((1R,2R)-2-tert-butylcyclopropyl)-3-chlorobenzoate

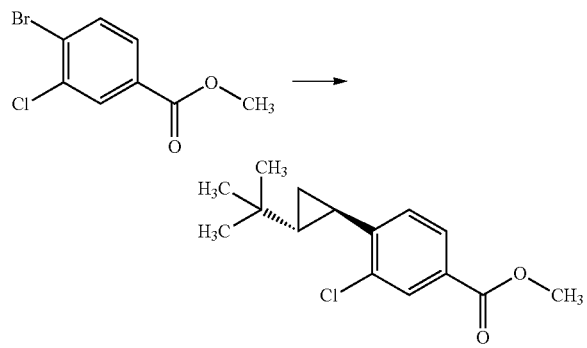

Potassium carbonate (1329 g) was mixed in water (1600 mL) under argon. To the reaction were added toluene (4800 mL), methyl 4-bromo-3-chlorobenzoate (800 g), (1R,2R)-2-tert-butylcyclopropylboronic acid (1454 g), and bis(triphenylphosphine)palladium (II) dichloride (112 g), and the reaction solution was stirred for 4.5 hours under heating at 80° C. The reaction solution was cooled to room temperature. To the reaction solution was added 0.5N aqueous solution of potassium hydroxide (3200 mL) under heating at 60° C., and the mixture was stirred for 2 hours. The organic layer was separated, and then the aqueous layer was extracted with toluene (1200 mL). Combined organic layers were washed with water (3200 mL), and then thereto was added Celite (800 g). The mixture was stirred at room temperature for 1 hour. Celite was removed with a filter, and then the filtrate was concentrated under reduced pressure. To the resulting residue was added isopropanol (2000 mL), and the mixture was concentrated under reduced pressure to give a crude product of the title compound (1061 g).

$^1$H NMR (400 MHz, DMSO-D$_6$) 0.91 (s, 9H), 1.02-1.07 (m, 3H), 2.13 (td, J=8.07, 5.68 Hz, 1H), 3.84 (s, 3H), 7.15 (d, J=8.37 Hz, 1H), 7.79 (dd, J=8.37, 1.79 Hz, 1H), 7.89 (d, J=1.79 Hz, 1H)

Step 4

4-((1R,2R)-2-tert-Butylcyclopropyl)-3-chlorobenzoic acid

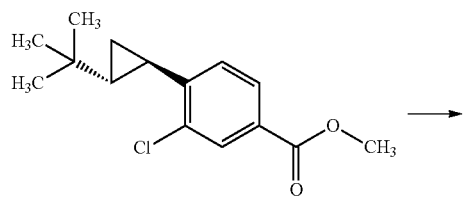

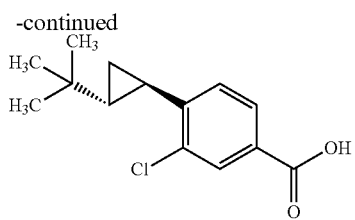

Methyl 4-((1R,2R)-2-tert-butylcyclopropyl)-3-chlorobenzoate (1061 g) was mixed in isopropanol (4600 mL). To the reaction solution was added 2N aqueous solution of sodium hydroxide (4000 mL), and the reaction solution was stirred at room temperature overnight. To the reaction solution was added activated carbon (160 g), and the mixture was stirred for 30 minutes. After filtration with Celite, 2N hydrochloric acid (4100 mL) was added to the filtrate under ice cooling. The filtrate was extracted with ethyl acetate (4800 mL). The aqueous layer was extracted with ethyl acetate (1200 mL), and combined organic layers were washed with saturated aqueous solution of sodium chloride (1600 mL) and then dried over magnesium sulfate. Magnesium sulfate was removed with a filter, and then the filtrate was concentrated under reduced pressure. To the resulting residue was added acetonitrile (1600 mL), and the mixture was concentrated under reduced pressure to give a crude product of the title compound (920 g).

$^1$H NMR (400 MHz, DMSO-D$_6$) 0.92 (s, 9H), 1.00-1.06 (m, 3H), 2.10-2.15 (m, 1H), 7.12 (d, J=7.77 Hz, 1H), 7.77 (d, J=7.77 Hz, 1H), 7.87 (s, 1H), 13.11 (br s, 1H)

Step 5

4-((1R,2R)-2-tert-Butylcyclopropyl)-3-chlorobenzoic acid

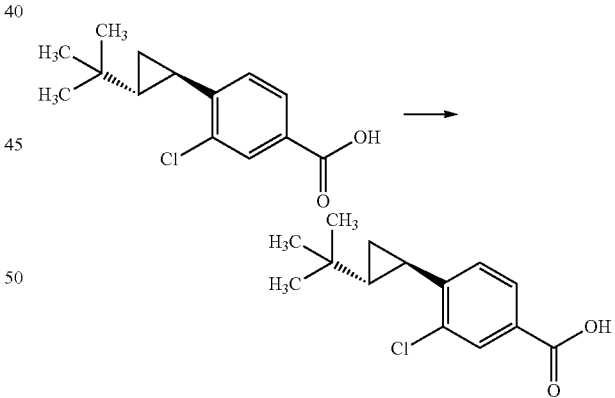

4-((1R,2R)-2-tert-Butylcyclopropyl)-3-chlorobenzoic acid (920 g) was mixed in acetonitrile (7200 mL) and water (4000 mL). The reaction solution was stirred under heating at an internal temperature of 67° C., and 4-((1R,2R)-2-tert-butylcyclopropyl)-3-chlorobenzoic acid was confirmed to be completely dissolved. Then, water (3700 mL) was added to the reaction solution, and thereto was added a seed crystal. The mixture was stirred for 6 hours under heating at 60° C. and then stirred overnight with being cooled slowly to room temperature. The precipitated solid was filtered to give the title compound (518 g). In this step, the seed crystal was used to obtain the crystal efficiently, but the crystal can be obtained without the seed crystal in similar procedures to this step.

$^1$H NMR (400 MHz, DMSO-D$_6$) 0.92 (s, 9H), 1.00-1.06 (m, 3H), 2.10-2.15 (m, 1H), 7.12 (d, J=7.77 Hz, 1H), 7.77 (d, J=7.77 Hz, 1H), 7.87 (s, 1H), 13.11 (br s, 1H)

Step 6

4-((1R,2R)-2-tert-Butylcyclopropyl)-3-chlorobenzoic acid (S)-phenethylamine salt

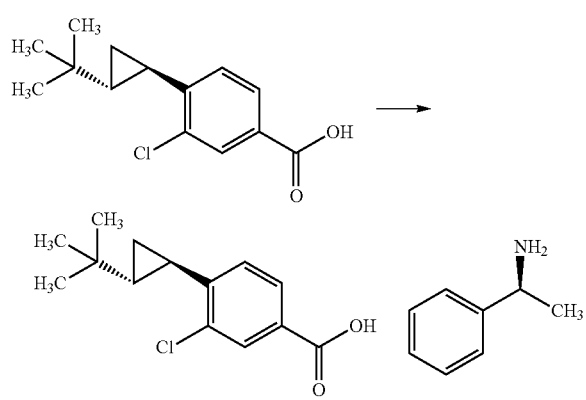

4-((1R,2R)-2-tert-Butylcyclopropyl)-3-chlorobenzoic acid (790 g) was mixed in isopropyl acetate (7900 mL). To the mixture was added dropwise (S)-(−)-phenethylamine (417 g) under heating at an internal temperature of 87° C. for 10 minutes. Then, a seed crystal was added thereto. The mixture was stirred for 2 hours under heating at 83° C. and then stirred overnight with being cooled slowly to room temperature. The precipitated solid was filtered to give the title compound (1087 g). In this step, the seed crystal was used to obtain the crystal efficiently, but the crystal can be obtained without the seed crystal in similar procedures to this step.

$^1$H NMR (400 MHz, DMSO-D$_6$) 0.91 (s, 9H), 0.94-1.00 (m, 3H), 1.41 (d, J=6.58 Hz, 3H), 2.05-2.09 (m, 1H), 4.25 (q, J=6.58 Hz, 1H), 6.98 (d, J=8.07 Hz, 1H), 7.27-7.30 (m, 1H), 7.35-7.38 (m, 2H), 7.45-7.47 (m, 2H), 7.70 (d, J=8.07 Hz, 1H), 7.81 (s, 1H)

Step 7

4-((1R,2R)-2-tert-Butylcyclopropyl)-3-chlorobenzoic acid (S)-phenethylamine salt

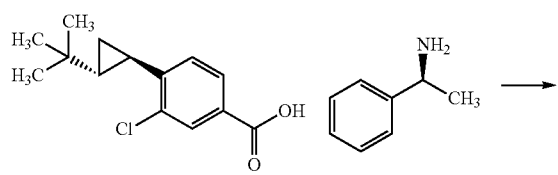

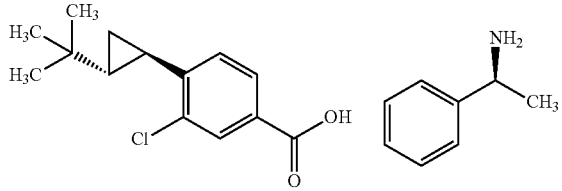

4-((1R,2R)-2-tert-Butylcyclopropyl)-3-chlorobenzoic acid (S)-phenethylamine salt (1087 g) was mixed in isopropyl acetate (7600 mL). To the reaction solution was added (S)-(−)-phenethylamine (35.2 g). The mixture was stirred for 2 hours under heating at 83° C. and then stirred overnight with being cooled slowly to room temperature. The precipitated solid was filtered to give the title compound (1044 g).

$^1$H NMR (400 MHz, DMSO-D$_6$) 0.91 (s, 9H), 0.94-1.00 (m, 31), 1.41 (d, J=6.58 Hz, 3H), 2.05-2.09 (m, 1H), 4.25 (q, J=6.58 Hz, 1H), 6.98 (d, J=8.07 Hz, 1H), 7.27-7.30 (m, 1H), 7.35-7.38 (m, 2H), 7.45-7.47 (m, 2H), 7.70 (d, J=8.07 Hz, 1H), 7.81 (s, 1H)

Step 8

4-((1R,2R)-2-tert-Butylcyclopropyl)-3-chlorobenzoic acid

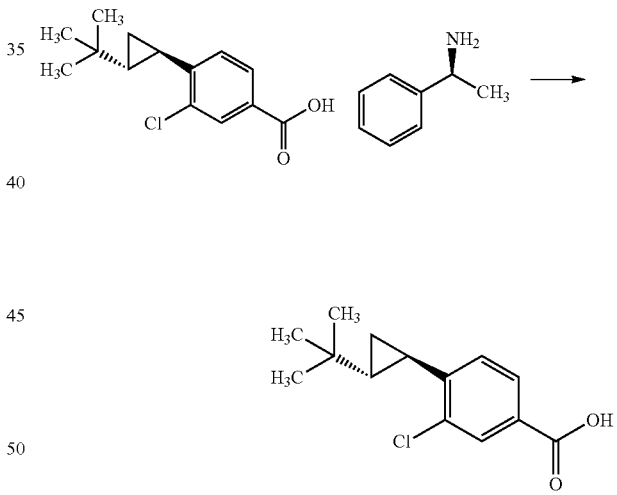

4-((1R,2R)-2-tert-Butylcyclopropyl)-3-chlorobenzoic acid (S)-phenethylamine salt (1044 g) was mixed in acetonitrile (5200 mL) and water (3800 mL). Thereto was added 2N hydrochloric acid (1470 mL), and the mixture was stirred for 2 hours under heating at 80° C. and then stirred overnight with being cooled slowly to room temperature. Then, thereto was added dropwise water (4200 mL) for 1 hour, and then the mixture was stirred at room temperature for 2 hours. The precipitated solid was filtered to give the title compound (697 g).

$^1$H NMR (400 MHz, DMSO-D$_6$) 0.92 (s, 9H), 1.00-1.06 (m, 3H), 2.10-2.15 (m, 1H), 7.12 (d, J=7.77 Hz, 1H), 7.77 (d, J=7.77 Hz, 1H), 7.87 (s, 1H), 13.11 (br s, 1H)

Step 8

4-((1R,2R)-2-tert-Butylcyclopropyl)-3-chloro-N-methoxy-N-methylbenzamide

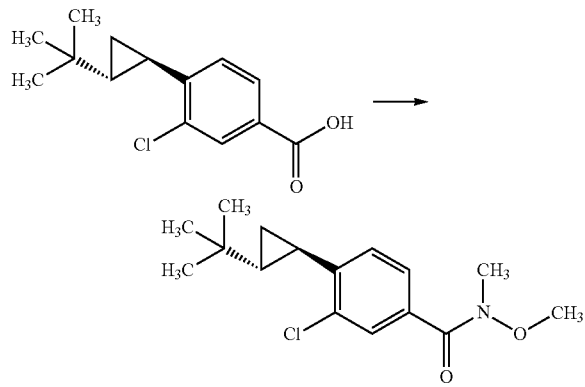

4-((1R,2R)-2-tert-Butylcyclopropyl)-3-chlorobenzoic acid (1000 g) was mixed in N-methylpyrrolidone (5000 mL). To the reaction solution were added N,O-dimethylhydroxylamine hydrochloride (540 g), 1-hydroxybenzotriazole monohydrate (60.6 g), and sodium hydrogen carbonate (465 g). To the mixture was added N-(3-dimethylaminopropyl)-N'-ethylcarbodiimide hydrochloride (1099 g) under ice cooling, and the mixture was stirred for 1 hour. The mixture was stirred at room temperature for 1 hour, and then thereto were added cyclopentyl methyl ether (5000 mL) and water (2500 mL). The aqueous layer was extracted with cyclopentyl methyl ether (400 mL), and combined organic layers were washed with water (2500 mL) and 20 w/v % aqueous solution of sodium chloride (2500 mL) and then dried over sodium sulfate. Sodium sulfate was removed with a filter, and then concentrated under reduced pressure. To the resulting residue was added cyclopentyl methyl ether (3000 mL), and the mixture was concentrated under reduced pressure to give a crude product of the title compound (1356 g).

$^1$H NMR (400 MHz, DMSO-D$_6$) 0.92 (s, 9H), 0.95-1.04 (m, 3H), 2.07-2.12 (m, 1H), 3.25 (s, 3H), 3.55 (s, 3H), 7.08 (d, J=7.77 Hz, 1H), 7.48 (d, J=7.77 Hz, 1H), 7.61 (s, 1H)

Step 8

1-[4-((1R,2R)-2-tert-Butylcyclopropyl)-3-chloro-phenyl]ethanone

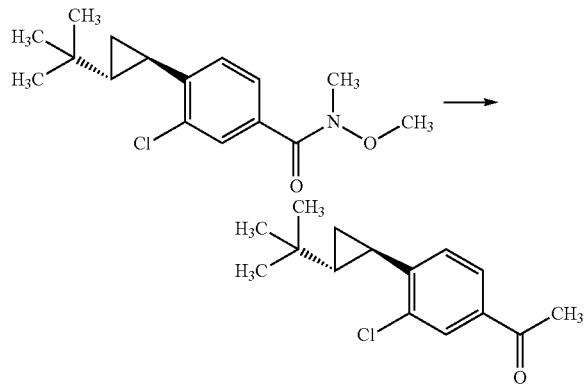

4-((1R,2R)-2-tert-Butylcyclopropyl)-3-chloro-N-methoxy-N-methylbenzamide (1356 g) was mixed in tetrahydrofuran (5900 mL). To the reaction solution was added dropwise 3M methylmagnesium chloride/tetrahydrofuran solution (1700 mL) under ice cooling for 2 hours, and then the mixture was stirred for 1 hour. To the reaction solution was added isopropanol (117 mL), and then thereto was added dropwise 2N hydrochloric acid (5900 mL). Toluene (6000 mL) was added thereto, and the organic layer was washed with 20 w/v % aqueous solution of sodium chloride (6000 mL) and water (3600 mL). Then, the solution was dried over sodium sulfate. Sodium sulfate was removed with a filter, and then concentrated under reduced pressure. To the resulting residue was added cyclopentyl methyl ether (3500 mL), and the mixture was concentrated under reduced pressure to give a crude product of the title compound (1193 g).

$^1$H NMR (400 MHz, DMSO-D$_6$) 0.92 (s, 9H), 1.02-1.07 (m, 3H), 2.11-2.16 (m, 1H), 2.55 (s, 3H), 7.14 (d, J=8.07 Hz, 1H), 7.79 (d, J=8.07 Hz, 1H), 7.92 (s, 1H)

Step 11

(S)-2-Methyl-propane-2-sulfinic acid {1-[4-((1R,2R)-2-tert-butylcyclopropyl)-3-chloro-phenyl]eth-(E)-yliden}amide

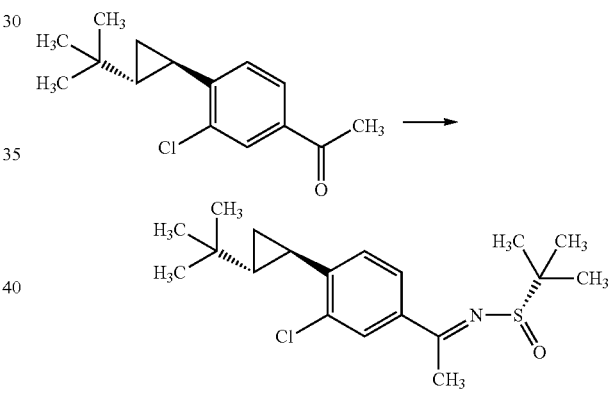

1-[4-((1R,2R)-2-tert-Butylcyclopropyl)-3-chloro-phenyl]ethanone (207 g) and (S)-(−)-2-methyl-propane-2-sulfinic acid amide (116 g) were mixed in cyclopentyl methyl ether (1000 mL). To the reaction solution was added tetraethyl orthotitanate (335 mL), and the reaction solution was stirred for 3 hours under heating at 110° C. To the reaction solution was added methanol (1000 mL) under water cooling, and the mixture was stirred for 10 minutes. Thereto was added dropwise a mixed aqueous solution of 28 w/w % aqueous solution of ammonia (100 mL), L-lactic acid (178 mL), and water (1000 mL) at an internal temperature of 30° C. or below for 15 minutes. The mixture was stirred at room temperature for 4 hours, and then let stand overnight. To the aqueous layer was added cyclopentyl methyl ether (1000 mL), and combined organic layers were washed with 25 w/v % aqueous solution of sodium chloride (1000 mL) and then dried over sodium sulfate. Sodium sulfate was removed with a filter, and then the filtrate was concentrated under reduced pressure. To the residue was added n-hexane (400 mL), and the mixture was concentrated under reduced pressure. To the residue was added n-hexane (400 mL) additionally, and then the mixture was concentrated under reduced pressure. Then, thereto was added dimethyl sulfoxide (500 mL), and the mixture was concentrated under reduced pressure. To the residue was added dimethyl sulfoxide (500 mL), and to the mixture was added dropwise water (50 mL) at room temperature. The mixture was stirred at room temperature for 30 minutes, and then thereto was added dropwise water (150 mL). The mixture was stirred at room temperature for 12 hours, and then the precipitated solid was filtered to give the title compound (261 g).

$^1$H NMR (400 MHz, DMSO-D$_6$) 0.91 (s, 9H), 1.01-1.05 (m, 3H), 1.21 (s, 9H), 2.12 (td, J=7.63, 5.78 Hz, 1H), 2.69 (s, 3H), 7.11 (d, J=8.55 Hz, 1H), 7.75 (dd, J=8.55, 1.62 Hz, 1H), 7.87 (d, J=1.62 Hz, 1H)

Step 12

Methyl (R)-3-[4-((1R,2R)-2-tert-Butylcyclopropyl)-3-chloro-phenyl]-2-isopropyl-3-((S)-2-methyl-propane-2-sulfinylamino)butanoate

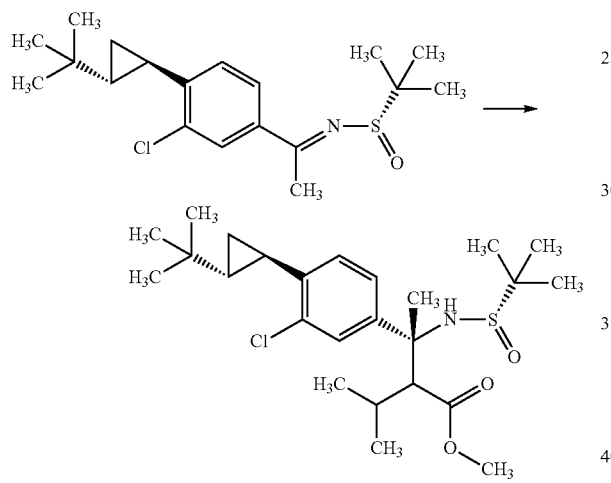

2M Lithium diisopropylamide/tetrahydrofuran/n-heptane/ethylbenzene solution (740 mL) was mixed in tetrahydrofuran (786 mL) under nitrogen flow. To the reaction solution was added dropwise a mixed solution of methyl 3-methyl-butanoate (224 mL) in tetrahydrofuran (524 mL) under cooling at −78° C. for 45 minutes, and the reaction solution was stirred under cooling at −78° C. for 2 hours 30 minutes. To the reaction solution was added dropwise a mixed solution of (S)-2-methyl-propane-2-sulfinic acid {1-[4-((1R,2R)-2-tert-butylcyclopropyl)-3-chloro-phenyl]eth-(E)-yliden}amide (261 g) in tetrahydrofuran (393 mL) for 40 minutes, and the reaction solution was stirred for 4 hours. To the reaction solution were added dropwise sequentially methanol (131 mL) and water (131 mL) within 5 minutes, and the mixture was stirred at room temperature for 14 hours. To the reaction solution was added water (786 ml) under water cooling, and the mixture was separated. The aqueous layer was extracted with toluene (1048 mL). Combined organic layers were washed sequentially with 1N sulfuric acid (1309 mL), water (786 mL), 5 w/v % aqueous solution of sodium hydrogen carbonate (786 mL), and 25 w/v % aqueous solution of sodium chloride (786 mL) and then dried over sodium sulfate. Sodium sulfate was removed with a filter, and then concentrated under reduced pressure. To the resulting residue was added toluene (262 mL), and the mixture was concentrated under reduced pressure to give a crude product of the title compound (348 g).

$^1$H NMR (400 MHz, DMSO-D$_6$) 0.76-0.92 (m, 18H), 1.15 (s, 6.3H), 1.20 (s, 2.7H), 1.75 (s, 0.9H), 1.76 (s, 2.1H), 1.93-2.04 (m, 2H), 2.68 (d, J=3.59 Hz, 0.3H), 2.93 (d, J=3.89 Hz, 0.7H), 3.52 (s, 2.1H), 3.58 (s, 0.9H), 5.15 (s, 0.7H), 5.44 (s, 0.3H), 6.97 (d, J=8.37 Hz, 0.7H), 6.98 (d, J=8.37 Hz, 0.3H), 7.31 (d, J=8.37 Hz, 1H), 7.46 (s, 0.7H), 7.49 (s, 0.3H)

Step 13

(S)-2-Methyl-propane-2-sulfinic acid [(R)-1-[4-((1R,2R)-2-tert-butylcyclopropyl)-3-chloro-phenyl]-2-hydroxymethyl-1,3-dimethyl-butyl}amide

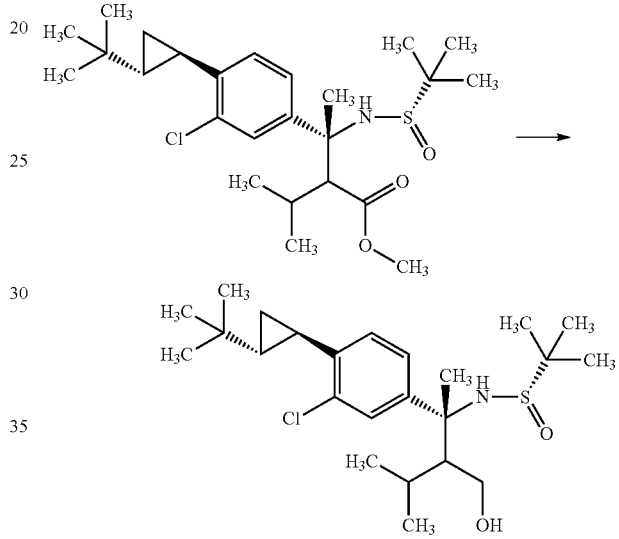

To 1M diisobutylaluminum hydride/toluene solution (2932 mL) was added dropwise a mixed solution of methyl (R)-3-[4-((1R,2R)-2-tert-butylcyclopropyl)-3-chloro-phenyl]-2-isopropyl-3-((S)-2-methyl-propane-2-sulfinylamino)butanoate (348 g) in toluene (1392 mL) under cooling at −78° C. for 1 hour under nitrogen flow. The reaction solution was stirred under cooling at −78° C. for 2 hours. The reaction solution was added to a mixed solution of citric acid monohydrate (622 g) in water (2088 mL) at an internal temperature of 20° C. or below under ice cooling. The mixture was stirred at room temperature for 15 hours, and then separated. The aqueous layer was extracted with toluene (1044 mL). Combined organic layers were washed sequentially with water (1740 mL) and 25 w/v % aqueous solution of sodium chloride (1740 mL), and then dried over sodium sulfate. Sodium sulfate was removed with a filter, and then the filtrate was concentrated under reduced pressure to give a crude product of the title compound (645 g).

$^1$H NMR (400 MHz, DMSO-D) 0.65 (d, J=7.09 Hz, 2.1H), 0.68-0.71 (m, 3H), 0.75 (d, J=7.09 Hz, 0.9H), 0.82-0.95 (m, 12H), 1.05 (s, 6.3H), 1.18 (s, 2.7H), 1.73 (s, 2.1H), 1.79 (s, 0.9H), 1.84-1.88 (m, 0.7H), 1.99-2.05 (m, 1.3H), 3.65-3.80 (m, 2H), 5.14 (t, J=3.55 Hz, 0.3H), 5.50 (t, J=3.91 Hz, 0.7H), 6.03 (s, 0.3H), 6.56 (s, 0.7H), 6.93-6.99 (m, 1H), 7.28-7.34 (m, 1H), 7.38 (d, J=1.96 Hz, 0.7H), 7.43 (d, J=1.71 Hz, 0.3H)

Step 14

(R)-3-Amino-3-[4-((1R,2R)-2-tert-butylcyclopropyl)-3-chloro-phenyl]-2-isopropyl-butan-1-ol hydrochloride

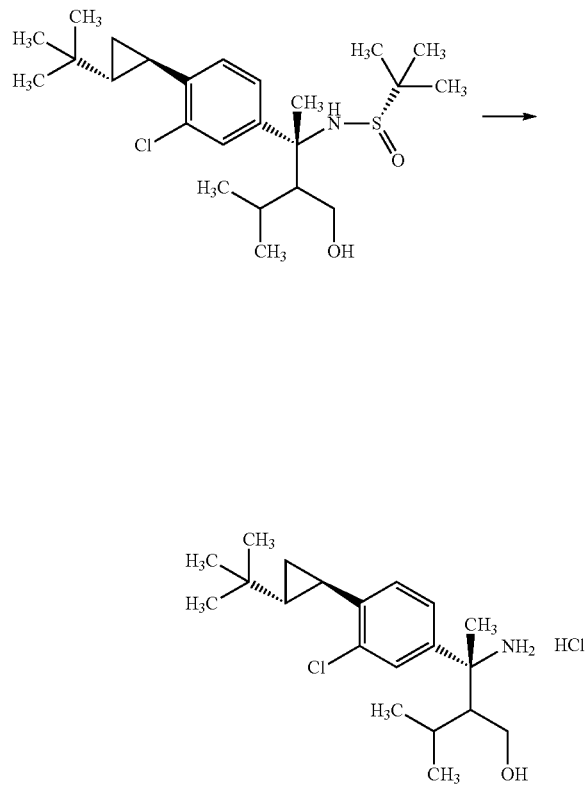

(S)-2-Methyl-propane-2-sulfinic acid [(R)-1-[4-((1R,2R)-2-tert-butylcyclopropyl)-3-chloro-phenyl]-2-hydroxymethyl-1,3-dimethyl-butyl}amide (327 g) was mixed in toluene (1309 mL). To the reaction solution was added dropwise 2M hydrogen chloride/methanol solution (740 mL) for 20 minutes under ice cooling, and the mixture was stirred for 2 hours under water cooling. The reaction solution was concentrated under reduced pressure, and to the residue was added diisopropyl ether (250 mL). The mixture was concentrated under reduced pressure, and then to the residue was added diisopropyl ether (4155 mL). The mixture was stirred for 6 hours under heating to 90° C. The reaction solution was stirred for 8 hours with being cooled slowly to room temperature, and then the precipitated solid was filtered to give the title compound (195 q).

¹H NMR (400 MHz, DMSO-D₅) 0.64 (d, J=6.88 Hz, 0.9H), 0.67 (d, J=6.88 Hz, 2.1H), 0.78 (d, J=6.68 Hz, 2.1H), 0.91 (s, 9H), 0.94-0.98 (m, 3H), 1.03 (d, J=6.88 Hz, 0.9H), 1.33-1.40 (m, 0.7H), 1.66 (s, 0.9H), 1.68 (s, 2.1H), 1.92-2.08 (m, 2.3H), 3.31-3.35 (m, 0.3H), 3.50-3.55 (m, 0.3H), 3.56-3.77 (m, 1.4H), 5.14 (br s, 0.3H), 5.29 (br s, 0.7H), 7.06 (d, J=8.37 Hz, 0.3H), 7.08 (d, J=8.37 Hz, 0.7H), 1.43 (d, J=8.37 Hz, 0.3H), 7.49 (d, J=8.37 Hz, 0.7H), 7.60 (s, 1H), 8.31 (br s, 2.1H), 8.49 (br s, 0.9H)

Step 15

Methyl 3-{3-[(R)-1-[4-((1R,2R)-2-tert-butylcyclopropyl)-3-chloro-phenyl]-2-hydroxymethyl-1,3-dimethyl-butyl]ureido}bicyclo[1.1.1]pentane-1-carboxylate

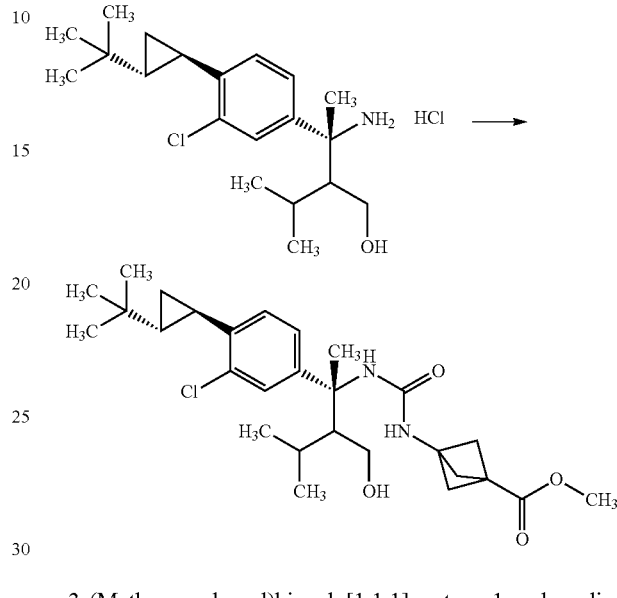

3-(Methoxycarbonyl)bicyclo[1.1.1]pentane-1-carboxylic acid (63.8 g) was mixed in toluene (761 mL) under argon flow, and thereto was added dropwise triethylamine (57.5 mL) over 5 minutes or above under water cooling. Thereto was added dropwise diphenylphosphoryl azide (89 mL) over 7 minutes or above under water cooling, and the mixture was stirred for 30 minutes. The mixture was stirred for 1 hour 30 minutes with heating to 100° C. The reaction solution was added dropwise for 37 minutes under ice cooling to a suspension which was prepared by mixing (R)-3-amino-3-[4-((1R,2R)-2-tert-butylcyclopropyl)-3-chloro-phenyl]-2-isopropyl-butan-1-ol hydrochloride (117 g) with tetrahydrofuran (819 mL) followed by dropwise addition of triethylamine (47.9 mL) to the mixture over 5 minutes or below under water cooling. The mixture was stirred for 30 minutes under ice cooling, and then stirred at room temperature for 1 hour 30 minutes. To the mixture was added dropwise 1N hydrochloric acid (1170 mL) over 15 minutes or above under ice cooling, and then the mixture was separated. The organic layer was washed sequentially with water (585 mL), 5 w/v % aqueous solution of sodium hydrogen carbonate (585 mL, twice), water (585 mL), and 25 w/v % aqueous solution of sodium chloride (585 mL), and then dried over sodium sulfate. Sodium sulfate was removed with a filter, and then the filtrate was concentrated under reduced pressure. To the resulting residue was added cyclopentyl methyl ether, and the mixture was concentrated under reduced pressure. This procedure was repeated twice to give a crude product of the title compound (192 g).

¹H NMR (400 MHz, CDCl₃) 0.27 (d, J=6.94 Hz, 0.9H), 0.73-0.79 (m, 1H), 0.82 (d, J=6.94 Hz, 2.1H), 0.86-0.99 (m, 2.9H), 0.89 (d, J=6.94 Hz, 2.1H), 0.93 (s, 2.7H), 0.94 (s, 6.3H), 1.49-1.55 (m, 1H), 1.84 (s, 2.1H), 1.89 (s, 0.9H), 2.07 (dt, J=8.79, 5.09 Hz, 1H), 2.27 (s, 4.2H), 2.28 (s, 1.8H), 2.36-2.29 (m, 1H), 3.66 (s, 2.1H), 3.69 (s, 0.9H), 3.73-3.82 (m, 1.3H), 3.91 (dd, J=10.98, 7.51 Hz, 0.7H), 4.52 (s, 0.7H), 4.59 (s, 0.3H), 6.71 (s, 0.3H), 6.82-6.85 (m, 1H), 6.92 (s, 0.7H), 7.14-7.18 (m, 1H), 7.30-7.31 (m, 1H)

Step 16

Methyl 3-{(S)-4-[4-((1R,2R)-2-tert-butyl-cyclopropyl)-3-chloro-phenyl]-5-isopropyl-4-methyl-2-oxo-3,4-dihydro-2H-pyrimidin-1-yl}bicyclo[1.1.1]pentane-1-carboxylate

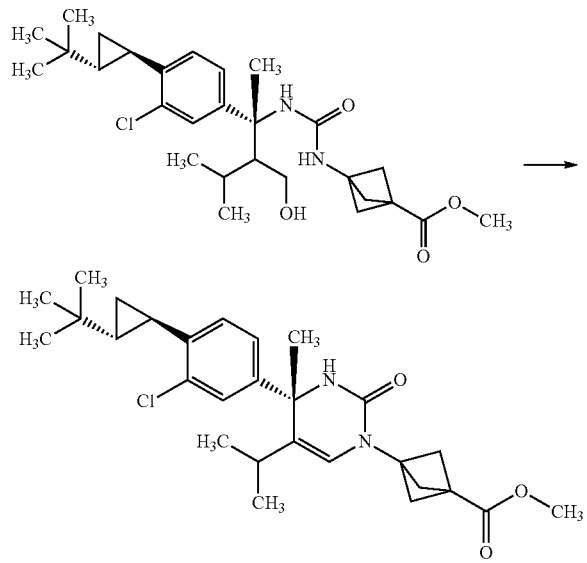

(Diacetoxyiodo)benzene (111 g) and 2,2,6,6-tetramethylpiperidine-1-oxyl radical (2.44 g) were mixed in acetic acid (632 mL) under nitrogen flow, and to the mixture was added dropwise a mixed solution of methyl 3-[3-[(R)-1-[4-((1R,2R)-2-tert-butylcyclopropyl)-3-chloro-phenyl]-2-hydroxymethyl-1,3-dimethyl-butyl]ureido)bicyclo[1.1.1]pentane-1-carboxylate (158 g) and 2,2,6,6-tetramethylpiperidine-1-oxyl radical (2.44 g) in cyclopentyl methyl ether (632 mL) at room temperature for 20 minutes. The reaction solution was stirred at room temperature for 17 hours, and then thereto was added dropwise trifluoroacetic acid (94 mL) for 9 minutes under water cooling. The reaction solution was stirred at room temperature for 3 hours 30 minutes, and then thereto was added 10 w/w % aqueous solution of sodium sulfite (474 mL) under water cooling. The mixture was stirred for 45 minutes. To the mixture was added n-heptane (790 mL), and the mixture was separated. The aqueous layer was extracted with n-heptane (474 mL). Combined organic layers were washed with water (790 mL, twice) and then dried over sodium sulfate. Sodium sulfate was removed with a filter, and then the filtrate was concentrated under reduced pressure. To the resulting residue was added toluene, and the mixture was concentrated under reduced pressure. This procedure was repeated twice. To the resulting residue was added isopropanol, and the mixture was concentrated under reduced pressure. This procedure was repeated three times to give a crude product of the title compound (197 g).

$^1$H-NMR (400 MHz, CDCl$_3$) 0.71 (d, J=7.09 Hz, 3H), 0.77-0.83 (m, 1H), 0.90-0.95 (m, 2H), 0.94 (s, 9H), 1.04 (d, J=7.09 Hz, 3H), 1.68 (s, 3H), 1.85-1.92 (m, 1H), 2.07-2.12 (m, 1H), 2.48 (s, 6H), 3.71 (s, 3H), 4.56 (s, 1H), 5.83 (s, 1H), 6.86 (d, J=8.31 Hz, 1H), 7.22 (dd, J=8.31, 1.96 Hz, 1H), 7.37 (d, J=1.96 Hz, 1H)

Step 8

3-{(S)-4-[4-((1R,2R)-2-tert-Butyl-cyclopropyl)-3-chloro-phenyl]-5-isopropyl-4-methyl-2-oxo-3,4-dihydro-2H-pyrimidin-1-yl}bicyclo[1.1.1]pentane-1-carboxylic acid Methyl 3-{(S)-4-[4-((1R,2R)-2-tert-butyl-cyclpropyl)-3-chloro-phenyl]-5-isopropyl-4-methyl-2-oxo-3,4-dihydro-2H-pyrimidin-1-yl}bicyclo[1.1.1]pentane-1-carboxylate (197 g) was mixed in isopropanol (437 mL) under nitrogen flow, and to the mixture was added dropwise 2N aqueous solution of sodium hydroxide (376 mL) for 12 minutes under water cooling. The reaction solution was stirred at room temperature for 3 hours, and then thereto was added n-heptane (730 mL). The mixture was separated. The aqueous layer was washed with n-heptane (730 mL). The aqueous layer was mixed in methyl tert-butyl ether (730 mL), and thereto was added dropwise 2N hydrochloric acid (584 mL) under ice cooling. Then, the mixture was separated. The organic layer was washed with water (438 mL, twice) and then dried over sodium sulfate. Sodium sulfate was removed with a filter, and then the filtrate was concentrated under reduced pressure. To the resulting residue was added acetonitrile, and the mixture was concentrated under reduced pressure to give a crude product of the title compound (152 g).

The resulting crude product was mixed in acetonitrile (2127 mL) under nitrogen flow, and the mixture was stirred for 6 hours under heating at 90° C. The reaction solution was stirred for 17 hours with being cooled slowly to room temperature, and then the precipitated solid was filtered to give Crystalline Form A (110 g) of the title compound.

The resulting crude crystal was mixed in isobutyl acetate (659 mL) and stirred under heating at 105° C. After the crude crystal was completely dissolved, hot filtration was performed. The filter was washed with isobutyl acetate (200 mL), and the filtrate was stirred under heating at 105° C. so that the precipitated solid was completely dissolved. The reaction solution was stirred for 3 hours with being cooled slowly under heating at 50° C., and then a seed crystal was added to the solution. The reaction solution was stirred for 1 hour 50 minutes with being cooled slowly under heating at 45° C. To the reaction solution was added dropwise n-heptane (2601 mL) for 56 minutes under heating at 55° C., and then the mixture was stirred for 2 hours. The reaction solution was stirred for 18 hours with being cooled slowly to room temperature, and then the precipitated solid was filtered to give Crystalline Form C (153 g) of the title compound.

$^1$H NMR (400 MHz, DMSO-D$_E$) 0.71 (d, J=6.94 Hz, 3H), 0.86-0.94 (m, 3H), 0.90 (s, 9H), 1.04 (d, J=6.94 Hz, 3H), 1.60 (s, 3H), 1.93-2.04 (m, 2H), 2.29 (s, 6H), 5.97 (s, 1H), 6.99 (d, J=7.86 Hz, 1H), 7.06 (s, 1H), 7.21 (dd, J=7.86, 1.85 Hz, 1H), 7.32 (d, J=1.85 Hz, 1H), 12.44 (s, 1H) 3-{(S)-4-[4-((1R,2R)-2-tert-Butyl-cyclopropyl)-3-chloro-phenyl]-5-isopropyl-4-methyl-2-oxo-3,4-dihydro-2H-pyrimidin-1-yl}bicyclo[1.1.1]pentane-1-carboxylic acid (50.0 mg) was mixed in toluene (0.1 mL) and n-heptane (0.1 mL), and the mixture was stirred under heating at 80° C. so that solids were completely dissolved. A seed crystal was added to the mixture, and the reaction solution was stirred for 6 hours with being cooled slowly to room temperature. Then, the precipitated solid was filtered to give Crystalline Form B (45.0 mg) of the title compound.

3-{(S)-4-[4-((1R,2R)-2-tert-Butyl-cyclopropyl)-3-chloro-phenyl]-5-isopropyl-4-methyl-2-oxo-3,4-dihydro-2H-pyrimidin-1-yl}bicyclo[1.1.1]pentane-1-carboxylic acid (9.71 g) was mixed in acetone (87.5 mL) and water (29 mL), and the mixture was stirred for 2 hours under heating at 70° C. so that solids were completely dissolved. The reaction solution was stirred for 2 hours under heating at 42.5° C. with being cooled slowly. The reaction solution was stirred for 15 hours with being cooled slowly to room temperature, and then the precipitated solid was filtered to give Crystalline Form D (7.52 g) of the title compound.

A crystal of the title compound (Crystalline Form D; 50.0 mg) was mixed in acetone (0.375 mL) and water (0.125 mL), and the mixture was stirred under heating at 58° C. until solids were completely dissolved. The reaction solution was stirred for 8 days with being cooled to room temperature, and then the resulting solid was filtered to give another crystal (Crystalline Form E; 18.6 mg) of the title compound, which was used for a seed crystal in the following procedure.

3-{(S)-4-[4-((1R,2R)-2-tert-Butyl-cyclopropyl)-3-chloro-phenyl]-5-isopropyl-4-methyl-2-oxo-3,4-dihydro-2H-pyrimidin-1-yl}bicyclo[1.1.1]pentane-1-carboxylic acid (500 mg) was mixed in acetone (3.6 mL) and water (0.9 mL), and the mixture was stirred under heating at 70° C. so that solids were completely dissolved. The seed crystal was added to the reaction solution with heating at 50° C., and the reaction solution was stirred for 1 hour. Thereto was added water (3 mL) with heating at 50° C., and the mixture was stirred for 2 hours. The reaction solution was stirred for 3 hours with being cooled slowly to room temperature, and then the precipitated solid was filtered to give Crystalline Form E (483 mg) of the title compound.

Example 2

Synthesis of 3-{(S)-5-((S)-sec-butyl)-4-[4-(2-tert-butyl-cyclopropyl)-3-chloro-phenyl]-4-methyl-2-oxo-3,4-dihydro-2H-pyrimidin-1-yl}bicyclo[1.1.1]pentane-1-carboxylic acid Step 1

(S)-2-[(R)-1-(4-Bromo-3-chloro-phenyl)-1-((S)-2-methyl-propane-2-sulfinylamino)-ethyl]-3-methyl-pentanoic acid ethyl ester

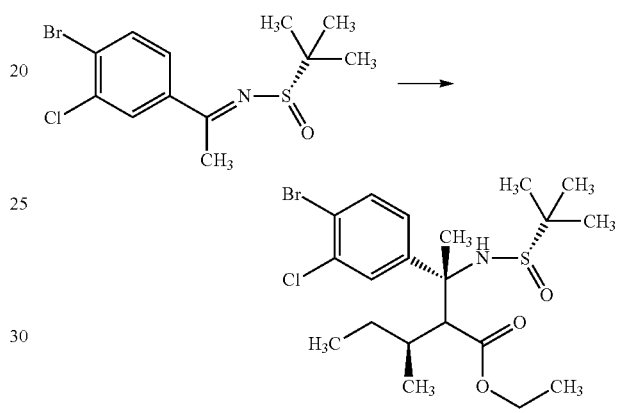

2M Lithium diisopropylamide/tetrahydrofuran/n-heptane/ethylbenzene solution (45 mL) was mixed in tetrahydrofuran (45 mL) under argon. To the reaction solution was added dropwise a mixed solution of (S)-3-methyl-pentanoic acid ethyl ester (12.9 g) in tetrahydrofuran (30 mL) under cooling at −78° C., and the reaction solution was stirred at −78° C. for 2 hours. To the reaction solution was added dropwise a mixed solution of (S)-2-methyl-propane-2-sulfinic acid [1-(4-bromo-3-chloro-phenyl)-eth-(E)-yliden]-amide (15.0 g) in tetrahydrofuran (40 mL), and the reaction solution was stirred under cooling at −78° C. for 2 hours. To the reaction solution was added saturated aqueous ammonium chloride solution, and the mixture was stirred at room temperature. The layers of the reaction solution were separated, and the aqueous layer was extracted with ethyl acetate (twice). Combined organic layers were washed with brine, and then dried over sodium sulfate. Sodium sulfate was removed through a filter, and then the filtrate was concentrated under reduced pressure. The resulting residue was purified by silica gel column chromatography (toluene:ethyl acetate=4:1) to give a mixture of diastereomers of the title compound (8.9 g).

$^1$H-NMR (400 MHz, CDCl$_3$) 0.66 (t, J=7.17 Hz, 2.4H), 0.87 (t, J=7.17 Hz, 0.6H), 0.92 (d, J=6.94 Hz, 0.6H), 1.00 (d, J=6.94 Hz, 2.4H), 1.05-1.13 (m, 1.6H), 1.19 (t, J=7.17 Hz, 0.6H), 1.24 (s, 1.8H), 1.27 (t, J=7.17 Hz, 2.4H), 1.32-1.35 (m, 7.6H), 1.42-1.52 (m, 0.8H), 1.67-1.73 (m, 0.2H), 1.88 (s, 0.6H), 1.90 (s, 2.4H), 2.52 (d, J=3.01 Hz, 0.8H), 2.82 (d, J=3.70 Hz, 0.2H), 4.07 (q, J=7.17 Hz, 0.4H), 4.18 (q, J=7.17 Hz, 1.6H), 5.04 (s, 0.2H), 5.49 (s, 0.8H), 7.18-7.21 (m, 1H), 7.55-7.59 (m, 2H)

Step 2

(S)-2-Methyl-propane-2-sulfinic acid [(1R,3S)-1-(4-bromo-3-chloro-phenyl)-2-hydroxymethyl-1,3-dimethyl-pentyl}amide

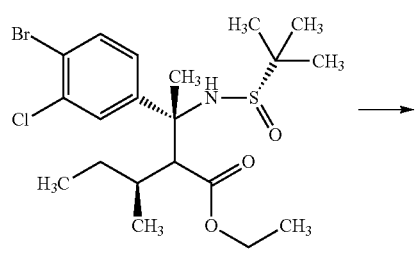

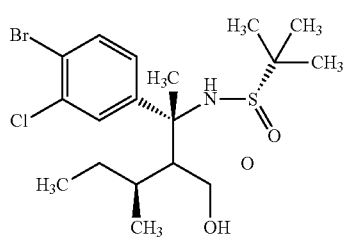

To an 1M diisobutylaluminum hydride/toluene solution (202 mL) was added dropwise a mixed solution of (S)-2-[(R)-1-(4-bromo-3-chloro-phenyl)-1-((S)-2-methyl-propane-2-sulfinylamino)-ethyl]-3-methylpentanoic acid ethyl ester (24.3 g) in toluene (100 mL) under argon under cooling at −78° C. The reaction solution was stirred under cooling at −78° C. for 2 hour 25 minutes. Methanol (24.5 mL) was added to the reaction solution under cooling at −78° C. To the reaction solution was added saturated aqueous (+)-potassium sodium tartrate solution (250 mL) under cooling at −78° C., and the mixture was stirred at room temperature for 2 hours. The layers of the reaction solution were separated, and the aqueous layer was extracted with toluene (300 mL). Combined organic layers were washed with saturated aqueous (+)-potassium sodium tartrate solution (200 mL), water (200 mL), and brine (200 mL), and then dried over sodium sulfate. Sodium sulfate was removed through a filter, and then the filtrate was concentrated under reduced pressure. The resulting residue was azeotroped with toluene to give a crude mixture of diastereomers of the title compound (24.7 g).

$^1$H-NMR (400 MHz, CDCl$_3$) 0.67-0.95 (m, 6H), 1.14 (s, 3.6H), 1.20-1.27 (m, 2H), 1.29 (s, 5.4H), 1.35-1.50 (m, 1H), 1.80-1.82 (m, 0.6H), 1.92 (s, 1.2H), 1.94 (s, 1.8H), 2.02-2.05 (m, 0.4H), 2.73-2.80 (m, 0.6H), 3.18-3.26 (m, 0.4H), 3.78-4.08 (m, 2H), 5.35 (s, 0.6H), 6.23 (s, 0.4H), 7.16-7.20 (m, 1H), 7.52-7.62 (m, 2H)

Step 3

(S)-2-[(R)-1-Amino-1-(4-bromo-3-chloro-phenyl)-ethyl]-3-methyl-pentan-1-ol

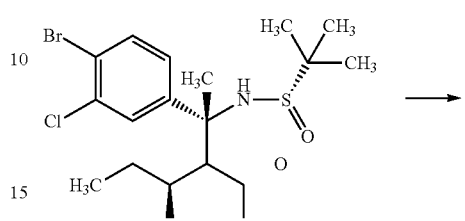

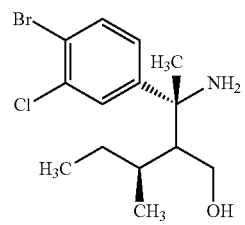

2-Methyl-propane-2-sulfinic acid [(1R,3S)-1-(4-bromo-3-chloro-phenyl)-2-hydroxymethyl-1,3-dimethyl-pentyl}amide (24.7 g) was mixed in toluene (124 mL). To the reaction solution was added dropwise 2M hydrogen chloride/methanol solution (50.4 mL) under ice cooling, and the reaction solution was stirred for 3 hours under cooling with a water bath. To the reaction solution was added 4N aqueous sodium hydroxide solution (25 mL) under ice cooling. The pH value of the reaction solution was adjusted to 12 by addition of 2N aqueous sodium hydroxide solution under ice cooling. The layers of the reaction solution were separated, and the aqueous layer was extracted with toluene (200 mL). Combined organic layers were washed with brine, and then dried over sodium sulfate. Sodium sulfate was removed through a filter, and then the filtrate was concentrated under reduced pressure. The resulting residue was azeotroped with toluene to give a crude mixture of diastereomers of the title compound (19.5 g).

$^1$H-NMR (400 MHz, CDCl$_3$) 0.55 (d, J=6.94 Hz, 1.8H), 0.75 (t, J=7.28 Hz, 1.2H), 0.79 (t, J=7.17 Hz, 1.8H), 0.84 (d, J=7.51 Hz, 1.2H), 0.86-1.07 (m, 1H), 1.20-1.29 (m, 1H), 1.35-1.45 (m, 1H), 1.59 (s, 1.2H), 1.62 (s, 1.8H), 1.72-1.74 (m, 0.6H), 1.87-1.90 (m, 0.4H), 3.69 (dd, J=12.02, 3.47 Hz, 0.4H), 3.75 (dd, J=11.56, 6.24 Hz, 0.6H), 3.85 (dd, J=12.02, 3.47 Hz, 0.6H), 3.92 (dd, J=11.56, 8.90 Hz, 0.4H), 7.18 (dd, J=8.55, 2.31 Hz, 0.4H), 7.22 (dd, J=8.55, 2.31 Hz, 0.6H), 7.50 (d, J=2.31 Hz, 0.4H), 7.56 (d, J=2.31 Hz, 0.6H), 7.59 (d, J=8.55 Hz, 0.6H), 7.60 (d, J=8.55 Hz, 0.4H)

Step 8

3-{3-[(1R,3S)-1-(4-Bromo-3-chloro-phenyl)-2-hydroxymethyl-1,3-dimethyl-pentyl]ureido}bicyclo[1.1.1]pentane-1-carboxylic acid methyl ester

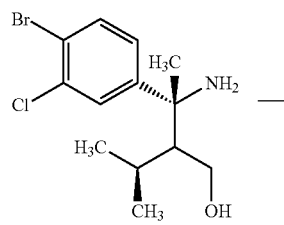

3-(Methoxycarbonyl)bicyclo[1.1.1]pentane-1-carboxylic acid (5.2 g) and toluene (50 mL) were mixed under argon, and thereto were added diphenylphosphoryl azide (7.2 mL) and triethylamine (4.6 mL) at room temperature. The reaction solution was stirred under heating at 110° C. for 1 hour. The reaction solution was added dropwise to a solution of (S)-2-[(R)-1-amino-1-(4-bromo-3-chloro-phenyl)-ethyl]-3-methyl-pentan-1-ol (9.8 g) in tetrahydrofuran (50 mL) over 10 minutes under ice cooling. The reaction solution was stirred at room temperature for 4 hours. To the reaction solution was added N,N,N'-trimethylethylenediamine (1.0 mL), and the solution was concentrated under reduced pressure. To the resulting residue was added 10% aqueous citric acid solution, and the mixture was extracted with ethyl acetate (twice). Combined organic layers were washed with brine, and then dried over sodium sulfate. Sodium sulfate was removed through a filter, and then the filtrate was concentrated under reduced pressure. The resulting residue was purified by silica gel column chromatography (ethyl acetate:n-hexane=1:1) to give the title compound (10.4 g).

$^1$H-NMR (400 MHz, CDCl$_3$) 0.18 (d, J=6.94 Hz, 1.8H), 0.76 (d, J=6.94 Hz, 1.2H), 0.80 (t, J=7.17 Hz, 1.2H), 0.87 (t, J=7.17 Hz, 1.8H), 1.23-1.28 (m, 1H), 1.48-1.77 (m, 3H), 1.84 (s, 1.2H), 1.91 (s, 1.8H), 2.29 (s, 2.4H), 2.29 (s, 3.6H), 3.67 (s, 3H), 3.67-3.70 (m, 0.6H), 3.77-3.85 (m, 1H), 3.97 (dd, J=11.33, 8.32 Hz, 0.4H), 4.60 (brs, 1H), 7.09-7.16 (m, 1H), 7.40-7.46 (m, 1H), 7.53 (d, J=8.32 Hz, 1H)

Step 8

3-[(S)-4-(4-Bromo-3-chloro-phenyl)-5-((S)-sec-butyl)-4-methyl-2-oxo-3,4-dihydro-2H-pyrimidin-1-yl]-bicyclo[1.1.1]pentane-1-carboxylic acid methyl ester

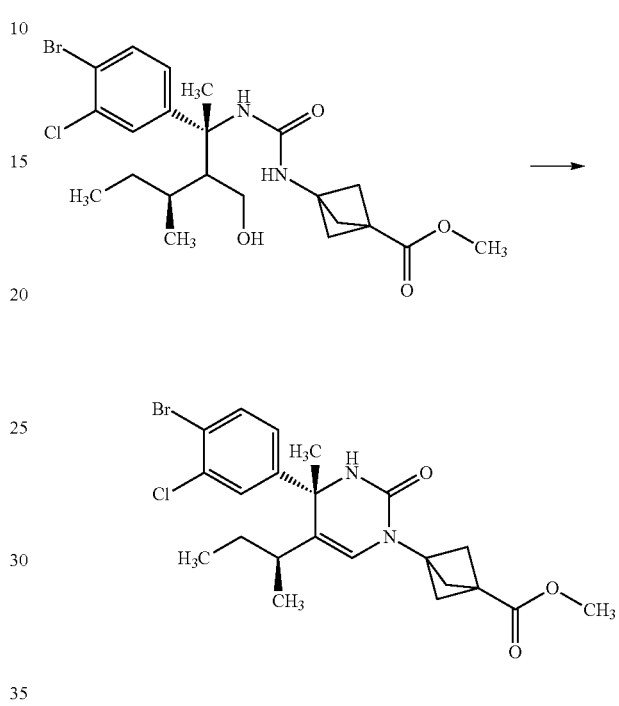

3-{3-[(1R,3S)-1-(4-Bromo-3-chloro-phenyl)-2-hydroxymethyl-1,3-dimethyl-pentyl]ureido}bicyclo[1.1.1]pentane-1-carboxylic acid methyl ester (10.4 g) and dichloromethane (100 mL) were mixed under argon, and thereto were added (diacetoxyiodo)benzene (7.3 g) and 2,2,6,6-tetramethylpiperidin-1-oxyl radical (0.323 g) at room temperature. The reaction solution was stirred at room temperature for 16.5 hours. Then, thereto were added a mixed solution of sodium thiosulfate (0.954 g) and water (40 mL) and saturated aqueous sodium hydrogen carbonate solution under ice cooling. The layers of the reaction solution were separated, and the aqueous layer was extracted with chloroform (twice). Combined organic layers were washed with saturated aqueous sodium hydrogen carbonate solution and brine, and then dried over sodium sulfate. Sodium sulfate was removed through a filter, and then the filtrate was concentrated under reduced pressure. The resulting residue was azeotroped with toluene. The resulting residue was mixed in toluene (100 mL), and thereto was added pentafluoroaniline trifluoromethanesulfonate (0.345 g) at room temperature. The reaction solution was stirred under warming at 110° C. for 3 hours. The reaction solution was concentrated under reduced pressure. The resulting residue was purified by silica gel column chromatography (ethyl acetate:n-hexane=1:2) to give the title compound (4.6 g).

$^1$H-NMR (400 MHz, CDCl$_3$) 0.64 (d, J=6.70 Hz, 3H), 0.86 (t, J=7.28 Hz, 3H), 1.25-1.36 (m, 1H), 1.40-1.51 (m, 1H), 1.53-1.63 (m, 1H), 1.67 (s, 3H), 2.47 (s, 6H), 3.71 (s, 3H), 4.61 (s, 1H), 5.77 (s, 1H), 7.21 (dd, J=8.44, 2.31 Hz, 1H), 7.52 (d, J=2.31 Hz, 1H), 7.58 (d, J=8.44 Hz, 1H)

Step 8

3-{(S)-5-((S)-sec-Butyl)-4-[4-(2-tert-butyl-cyclopropyl)-3-chloro-phenyl]-4-methyl-2-oxo-3,4-dihydro-2H-pyrimidin-1-yl}bicyclo[1.1.1]pentane-1-carboxylic acid methyl ester

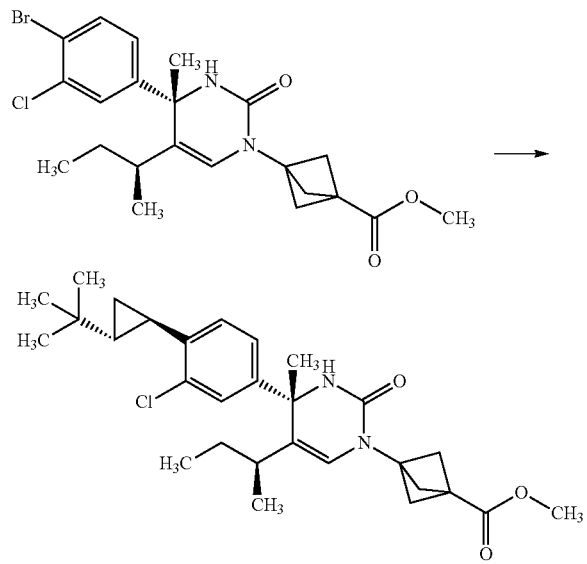

3-[(S)-4-(4-Bromo-3-chloro-phenyl)-5-((S)-sec-butyl)-4-methyl-2-oxo-3,4-dihydro-2H-pyrimidin-1-yl]-bicyclo[1.1.1]pentane-1-carboxylic acid methyl ester (4.6 g), potassium trans-2-tert-butyl-cyclopropyl-trifluoroborate (2.4 g), [1,1'-bis(di-tert-butyl-phosphino)ferrocene]palladium (II) dichloride (0.62 g), cesium carbonate (9.4 g), toluene (50 mL), and water (5 mL) were mixed under argon. The reaction solution was stirred under heating at 100° C. for 3.5 hours. To the reaction solution was added ammonium 1-pyrrolidinecarbodithioate (0.69 g) under cooling with a water bath, and the mixture was stirred for 50 minutes. To the reaction solution was added additional ammonium 1-pyrrolidinecarbodithioate (0.69 g) at room temperature, and the mixture was stirred for 20 minutes. Insoluble substances were filtered through Celite. The filtrate was separated, and the resulting aqueous layer was extracted with ethyl acetate (twice). Combined organic layers were washed with brine, and then dried over sodium sulfate. Sodium sulfate was removed through a filter, and then the filtrate was concentrated under reduced pressure. The resulting residue was purified by silica gel column chromatography (ethyl acetate:n-hexane=1:2) to give a diastereomer mixture (3.5 g). The resulting diastereomer mixture (0.84 g) was purified with a chiral preparative column to give the title compound (0.29 g).

Purification conditions for the preparative column are shown as follows.
Preparative apparatus: Recycling Preparative Liquid Chromatograph LC-9225 NEXT SERIES, Japan Analytical Industry Co., Ltd.
Column: Daicel CHIRALPAK IA 2.0 cmφ×25 cm
Mobile phase: hexane:2-propanol=93:7
Flow rate: 10.0 mL/min
Detection: UV (220 nm)

Measurement with a chiral column showed 10.0 minutes of the retention time for the resulting title compound (9.4 minutes of the retention time for diastereomers of the title compound) with 99% de purity. Analytical conditions for the chiral column are shown as follows.
Measuring apparatus: HPLC system, Shimadzu Corporation, High-Performance Liquid Chromatograph Prominence
Column: Daicel CHIRALPAK IA-3 0.46 cmφ×15 cm Column temperature: 40° C.
Mobile phase: hexane:2-propanol=95:5
Flow rate: 1.0 mL/min
Detection: UV (220 nm)
$^1$H-NMR (400 MHz, CDCl$_3$) 0.63 (d, J=6.70 Hz, 3H), 0.83-0.77 (m, 1H), 0.85 (t, J=7.28 Hz, 3H), 0.88-0.94 (m, 11H), 1.25-1.34 (m, 1H), 1.41-1.50 (m, 1H), 1.58-1.63 (m, 1H), 1.66 (s, 3H), 2.08-2.12 (m, 1H), 2.47 (s, 6H), 3.71 (s, 3H), 4.55 (s, 1H), 5.75 (s, 1H), 6.86 (d, J=8.09 Hz, 1H), 7.24 (dd, J=8.09, 2.08 Hz, 1H), 7.37 (d, J=2.08 Hz, 1H)

Step 8

3-{(S)-5-((S)-sec-Butyl)-4-[4-((R,2R)-2-tert-butyl-cyclopropyl]-3-chloro-phenyl]-4-methyl-2-oxo-3,4-dihydro-2H-pyrimidin-1-yl}bicyclo[1.1.1]pentane-1-carboxylic acid

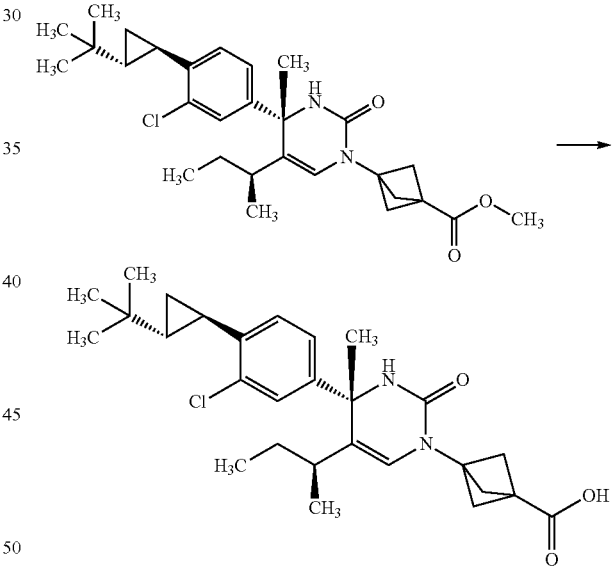

3-{(S)-5-((S)-sec-Butyl)-4-[4-(2-tert-butyl-cyclopropyl)-3-chloro-phenyl]-4-methyl-2-oxo-3,4-dihydro-2H-pyrimidin-1-yl}bicyclo[1.1.1]pentane-1-carboxylic acid methyl ester (0.287 g), tetrahydrofuran (2 mL), and methanol (2 mL) were mixed, and thereto was added 2N aqueous sodium hydroxide solution (0.58 mL) at room temperature. The reaction solution was stirred at room temperature for 18 hours. The reaction solution was concentrated, and to the resulting residue were added 1N hydrochloric acid and water. The mixture was extracted with ethyl acetate (twice). Combined organic layers were washed with brine, and then dried over sodium sulfate. Sodium sulfate was removed through a filter, and then the filtrate was concentrated under reduced pressure. To the resulting residue were added acetonitrile (1.5 mL) and water (10 mL), and the mixture was stirred at room temperature. The precipitated solid was filtered to give the title compound (0.268 g).

$^1$H-NMR (400 MHz, DMSO-D$_6$) 0.61 (d, J=6.70 Hz, 3H), 0.81 (t, J=7.40 Hz, 3H), 0.86-0.91 (m, 12H), 1.22-1.32 (m, 1H), 1.39-1.49 (m, 1H), 1.56 (s, 3H), 1.63-1.71 (m, 1H), 1.98-2.04 (m, 1H), 2.27 (s, 6H), 5.87 (s, 1H), 6.98 (d, J=8.20 Hz, 1H), 7.04 (s, 1H), 7.20 (dd, J=8.21, 2.20 Hz, 1H), 7.30 (d, J=2.20 Hz, 1H), 12.42 (brs, 1H) Absolute configurations of the asymmetric carbons of the title compound were determined by single-crystal X-ray structural analysis.

Example 3

Crystalline Polymorphs of 3-{(S)-4-[4-((1R,2R)-2-tert-butyl-cyclopropyl)-3-chloro-phenyl]-5-isopropyl-4-methyl-2-oxo-3,4-dihydro-2H-pyrimidin-1-yl}bicyclo[1.1.1]pentane-1-carboxylic acid X-ray powder diffraction (XRD), simultaneous measurement of thermogravimetric analysis and differential thermal analysis (TG-DTA), and differential scanning calorimetry (DSC) were performed for Crystalline Forms A to E of the title compound. Measuring apparatus and conditions for each measurement are shown as follows.

Powder X-Ray Diffractometry:

Measuring apparatus: X'pert-PRO-MPD (Spectris Co., Ltd.)

Measuring conditions: X ray, Cu/45 kV/40 mA, Analyzed by transmission method

Simultaneous Measurement of Thermogravimetry Analysis and Differential Thermal Analysis:

Measuring apparatus: TGA/SDTA851®/SF (Mettler Toledo International Inc.)

Measuring conditions: Heating rate 5° C./min.

Differential Scanning Calorimetry:

Measuring apparatus: DSC Q2000 (TA Instruments Japan Inc.) Measuring conditions: Heating rate 10° C./min.

Each measurement result for each crystalline form is shown as below.

A. Crystalline Form A

XRD data is shown in FIG. 1. Diffraction angle 2θ and diffraction intensity of each peak are shown as follows.

| Pos. [°2Th.] | Relative intensity [%] | NET intensity [cts] |
| --- | --- | --- |
| 4.4150 | 88.60 | 696.00 |
| 4.7253 | 92.34 | 725.34 |
| 9.3448 | 51.69 | 406.05 |
| 12.6233 | 89.18 | 700.54 |
| 15.5239 | 54.31 | 426.65 |
| 15.9538 | 100.00 | 785.54 |
| 18.9756 | 93.38 | 733.57 |
| 19.3806 | 61.14 | 480.24 |
| 23.4055 | 52.66 | 413.64 |

DSC data is shown in FIG. 2. Enthalpy of endothermic peaks on the DSC curve was 68.5 J/g, the endothermic temperature was 195° C., and the extrapolated onset temperature was 193° C.

B. Crystalline Form B

XRD data is shown in FIG. 3. Diffraction angle 2θ and diffraction intensity of each peak are shown as follows.

| Pos. [°2Th.] | Relative intensity [%] | NET intensity [cts] |
| --- | --- | --- |
| 7.3234 | 41.66 | 1172.05 |
| 8.6616 | 59.85 | 1683.77 |
| 10.3766 | 54.65 | 1537.60 |
| 11.3651 | 74.04 | 2083.03 |
| 15.7159 | 100.00 | 12813.48 |
| 16.4562 | 33.94 | 954.94 |
| 17.0881 | 38.09 | 1071.78 |
| 17.3618 | 97.60 | 2746.08 |
| 18.8969 | 91.19 | 2565.57 |
| 20.2651 | 27.35 | 769.36 |
| 21.2939 | 11.22 | 315.81 |
| 23.7512 | 11.98 | 336.95 |

DSC data is shown in FIG. 4. Enthalpy of endothermic peaks on the DSC curve was 76.0 J/g, the endothermic temperature was 230.2° C., and the extrapolated onset temperature was 229.6° C.

C. Crystalline Form C

XRD data is shown in FIG. 5. Diffraction angle 2θ and diffraction intensity of each peak are shown as follows.

| Pos. [°2Th.] | Relative intensity [%] | NET intensity [cts] |
| --- | --- | --- |
| 7.4077 | 100.00 | 18820.91 |
| 9.9304 | 14.05 | 2644.11 |
| 10.4586 | 9.36 | 1760.82 |
| 11.3577 | 6.59 | 1240.81 |
| 11.5929 | 20.31 | 3821.92 |
| 13.3543 | 32.22 | 6063.80 |
| 14.1920 | 6.30 | 1186.13 |
| 17.4101 | 41.14 | 7743.09 |
| 18.2839 | 20.79 | 3912.93 |
| 18.6516 | 54.77 | 10307.31 |
| 19.3578 | 33.49 | 6302.58 |

DSC data is shown in FIG. 6.

D. Crystalline Form D

XRD data is shown in FIG. 7. Diffraction angle 2θ and diffraction intensity of each peak are shown as follows.

| Pos. [°2Th.] | Relative intensity [%] | NET intensity [cts] |
| --- | --- | --- |
| 4.2615 | 100.00 | 1492.44 |
| 9.4092 | 32.36 | 482.89 |
| 14.1307 | 71.27 | 1063.67 |
| 14.9941 | 54.60 | 814.89 |
| 16.0213 | 26.03 | 388.41 |
| 17.9068 | 24.55 | 366.47 |
| 18.6997 | 76.03 | 1134.65 |
| 20.2231 | 17.90 | 267.20 |
| 23.1278 | 16.36 | 244.14 |

TG-DTA data is shown in FIG. 8. The rate of weight decrease was 3.6% by dehydration. This value corresponded to the theoretical water content of a monohydrate of the title compound, and Crystalline Form D was deemed to be a monohydrate of the title compound.

DSC data is shown in FIG. 9. Enthalpy of endothermic peaks on the DSC curve was 118.4 J/g, the endothermic temperature was 128.0° C., and the extrapolated onset temperature was 118.9° C.

E. Crystalline Form E

XRD data is shown in FIG. 10. Diffraction angle 2θ and diffraction intensity of each peak are shown as follows.

| Pos. [°2Th.] | Relative intensity [%] | NET intensity [cts] |
|---|---|---|
| 4.2178 | 100.00 | 1955.54 |
| 9.6770 | 17.62 | 344.56 |
| 13.7062 | 39.21 | 766.72 |
| 13.9822 | 39.97 | 781.71 |
| 15.1994 | 21.16 | 413.75 |
| 15.4232 | 21.09 | 412.41 |
| 16.9120 | 24.01 | 469.52 |
| 18.8094 | 23.63 | 462.14 |
| 20.4669 | 15.16 | 296.44 |
| 21.9321 | 15.19 | 296.96 |
| 22.3640 | 9.64 | 188.43 |

TG-DTA data is shown in FIG. 11. The rate of weight decrease was 3.9% by melting. This value corresponded to the theoretical water content of a monohydrate of the title compound, and Crystalline Form E was deemed to be a monohydrate of the title compound.

DSC data is shown in FIG. 12. Enthalpy of endothermic peaks on the DSC curve was 138.1 J/g, the endothermic temperature was 125.9° C., and the extrapolated onset temperature was 115.0° C.

Test Example 1

In-Vitro Assay for Inhibitory Effect Against RORγ Transcriptional Activity

Inhibitory effect against RORγ transcriptional activity was assessed by reporter gene assay for test compounds.

cDNAs encoding human and mouse RORγ ligand binding domains (LBD) were obtained based on the sequences of human RORγ (Genbank registered number NM_005060.3) and mouse RORγ (Genbank registered number NM_011281.2) (LBD sequences: from Ser253 to Lys518 for human RORγ; from Ile251 to Lys516 for mouse RORγ).

LBD cDNAs of human and mouse RORγ were inserted into pFA-CMV vector (Agilent Technologies, Inc.), which expresses GAL4-DNA binding domain fusion protein. The resulting plasmids are hereinafter referred to as pFA/hRORγ plasmid and pFA/mRORγ plasmid, respectively.

pFA/hRORγ plasmid or pFA/mRORγ plasmid was transiently co-transfected into Chinese hamster ovary cells (CHO cells) with pG5-Luc (Promega), reporter plasmid expressing firefly luciferase in a GAL4-dependent manner.

TransIT (Registered trademark) CHO Transfection Kit (Mirus) was used to co-transfect CHO cells with the plasmids. One day prior to the assay, CHO cells were suspended in HAM F-12 Nutrient medium containing 10% (v/v) fetal bovine serum and seeded at $5.5 \times 10^6$ cells per 225 cm² cell culture flask each. 72 μL of TransIT (Registered trademark) CHO Reagent was added into a 2 mL tube containing 1.55 mL of Opti-MEM, and then mixed and incubated at room temperature for 10 min. 50.4 μL of a plasmid solution containing 300 ng of pFA/hRORγ plasmid, 12000 ng of pG5-Luc plasmid, and 1170 ng of pcDNA3.1 plasmid were added into the tube and mixed gently. In the case of mouse assay, a plasmid solution containing 300 ng of pFA/mRORγ plasmid, 12000 ng of pG5-Luc plasmid, and 11700 ng of pcDNA3.1 plasmid was added, instead. The mixture was incubated at room temperature for 10 min. 12 μL of CHO Mojo Reagent was then added into each tube and mixed gently. The mixture was incubated at room temperature for 10 min. The resulting transfection reagent was applied to the cell culture. After incubation at 37° C., 5% $CO_2$ for 4 hours, the plasmid-transfected CHO cells were harvested by trypsin treatment. The collected cells were resuspended in culture medium and plated into a 384-well-white plate at 8,000 cells/35 μL/well. The plate was let stand at room temperature for 1 hour and then incubated at 37° C., 5% $CO_2$ for 3 hours. Test compounds were dissolved in dimethyl sulfoxide (DMSO) to obtain a concentration of 10 mM. Each solution was serially diluted with DMSO and further diluted with culture medium just before use. The test compound solutions were added to the cells in the plate at 6 different concentrations. The final concentration of DMSO was 0.2% (v/v). After the addition of test compound, the cells were incubated at 37° C., 5% $CO_2$ for 2 days.

Cell viability was tested by luminescence method with CellTiter-Glo (Promega). Two days after the addition of test compound, 40 μL each of CellTiter-Glo was added into the 384-well-plate. Ten minutes after the addition, luminescence was measured for each well with a microplate reader. The luminescence count in the cells treated with 0.2% DMSO alone was defined as 100%, and the cell viability after treatment with the test compound was calculated as a percentage (%-of-control) based on the value of 0.2% DMSO alone. When the cell viability was 70% or less, a test compound was assessed to have cytotoxicity.

RORγ transcriptional activity was detected as the intracellular luciferase activity using SteadyLite HTS Reporter Gene Assay System (Perkin Elmer). StedyLite Reagent was diluted 2.5-fold with Extension buffer (10 mM Tricine, 0.2% (w/v) bovine serum albumin, 0.02% (v/v) Tween-20) to obtain a luciferase substrate solution. Two days after the addition of test compound, 40 μL each of the luciferase substrate solution was added into the 384-well-plate. After the incubation at room temperature for 10 minutes, luminescence of each well was measured with a microplate reader. The luciferase activity derived from the luminescence count in a vehicle-control well treated with 0.2% DMSO alone was defined as 100%, and the luciferase activity after treatment with the test compound was calculated as a percentage (%-of-control) based on the value of the vehicle-control. An $EC_{50}$ value of the test compound was calculated by curve fitting. The luminescence counts at the concentration of test compound where cytotoxicity was observed were excluded from data analysis.

The results are shown in the table below.

| Compound | LUC $EC_{50}$ (μM) | |
|---|---|---|
| | hRORγ | mRORγ |
| (1) | 0.023 | 0.023 |
| (2) | 0.014 | 0.029 |

Test Example 2

Assessment for In-Vitro Metabolic Stability
A. Metabolic Stability in Liver Microsomes
(1) Preparation of a Test Solution
A test solution was prepared by diluting 10 mM DMSO solution of a test substance with acetonitrile by 100 times.
(2) Metabolic Stability Study with Liver Microsomes
Human and animal liver microsomes (SEKISUI XENOTECH; Human (H2610), Rat (R1000), Mouse (M1000), Monkey (P2000), Dog (D1000)) were adjusted with potassium phosphate buffer (pH 7.4) to 0.2 mg/mL in the reaction system. Then, 1% of the solution of a test substance prepared was added to the reaction system. Thereto was added an NADPH generating system (prepared according to the method of Non Patent Literature 28), and the metabolic reaction was initiated. At a designated time, 0.1% formic acid-acetonitrile/water (3:1) was added thereto, and the reaction was terminated.

(3) Analysis by LC/MS

The sample after termination of the reaction was separated by centrifugation (1400 g, 20 min.), and then the supernatant was measured by LC/MS (UPLC-SQD (waters)) to calculate a residual ratio of unreacted substances.

B. Metabolic Stability in Hepatocytes (1) Preparation of a Test Solution

A test solution was prepared by diluting 10 mM DMSO solution of a test substance with acetonitrile by 20 times.

(2) Metabolic Stability Study with Hepatocytes

Human and animal cryopreserved hepatocyte (BIOIVT; Human (IVT-X008000), Rat (IVT-M00005), Monkey (IVT-M00305), Dog (IVT-M00205)) were adjusted with William's Medium E (SIGMA; W1878) to $1\times10^6$ cells/mL of a cell suspension, which was then added to a 96-well plate. Then, 1% of the solution of a test substance prepared was added to the reaction system, and the metabolic reaction was initiated. At a designated time, 0.1% formic acid-acetonitrile was added thereto, and the reaction was terminated.

(3) Analysis by LC/MS

The sample after termination of the reaction was separated by centrifugation (1400 g, 20 min.), and then the supernatant was measured by LC/MS (UPLC-SQD (waters)) to calculate a residual ratio of unreacted substances.

Results are shown in the following table.

| Compound | Metabolic stability in liver microsomes at 60 min. (%) | | | | |
|---|---|---|---|---|---|
| | Human | Rat | Mouse | Monkey | Dog |
| (1) | 99 | 103 | 95 | 93 | 98 |
| (2) | 96 | 95 | 98 | 96 | 95 |

| Compound | Metabolic stability in hepatocytes at 240 min. (%) | | | |
|---|---|---|---|---|
| | Human | Rat | Monkey | Dog |
| (1) | 94 | 90 | 83 | 88 |
| (2) | 94 | 94 | 85 | 78 |

Test Example 3

Measurement of Potential for Induction of CYP3A4

Potential for induction of CYP3A4 was evaluated with Nuclear Receptor Activation Kits (PURACYP; DPX2-96-002) according to protocols attached.

The following experiment was performed with substances accompanying Nuclear Receptor Activation Kits (PURACYP; DPX2-96-002).

A measurement method is specifically shown as follows. DPX2 cells were seeded on a 96-well plate and incubated with a $CO_2$ incubator for 24 hours. A compound-supplemented medium was prepared by adding 0.1% of a DMSC solution of test compound (1, 3, 10 mM) or rifampicin (10 mM) as a positive control to a medium. The media on 96-well plate were removed with an aspirator 24 hours after seeding, and thereto was added the compound-supplemented medium which was prepared. CellTiter-Fluor was added to the medium 48 hours after the addition of compound, and the mixture was incubated with a $CO_2$ incubator for 1 hour. Then, a cell viability was measured by the fluorometric method. ONE-Glo was added to the mixture, and the mixture was incubated with a $CO_2$ incubator for 5 minutes. Then, the reporter activity was measured by luminescent determination. The induction ratio was calculated by comparing the resulting reporter activity with a DMSO control sample. % of positive control was calculated from the following equation.

$$\% \text{ positive control} = \frac{\left(\begin{array}{c}\text{activity of test drug treated cells} - \\ \text{activity of negative control}\end{array}\right) \times 100}{(\text{activity of positive control} - \text{activity of negative control})}$$

Results are shown in the following table.

| Compound | Potential for induction of CYP3A4 (%) | | |
|---|---|---|---|
| | 3 µM | 10 µM | 30 µm |
| (1) | <10 | <10 | <10 |
| (2) | <10 | <10 | ND |

ND: Not determined.

Test Example 4

Measurement of Solubility

A 10 mM DMSO solution (10 µL) of test substance was added to a 96-well plate, and the mixture was concentrated and dried with a centrifugal evaporator (Genevac HT-4X). 200 µL of each solvent (JP1, JP2, FaSSIF, FeSSIF) (see Non Patent Literatures 29 and 30) was added to the well after evaporation. The mixture was shaken at room temperature at 2500 rpm for 4 hours. Then, the mixture was filtered in two parts with MultiScreen PCF filter (MERCK Millipore; MSSLBPC) to give samples (50 and 100 µL). 40 UL was collected from the sample obtained in the second filtration, and thereto was added acetonitrile (300 µL). After centrifugation (4000 g, 5 min.) of the mixture, a part of the supernatant was measured by LC-UV/MS (UPLC-Premier (waters)).

Results are shown in the following table.

| Compound | Solubility (µM) | | | |
|---|---|---|---|---|
| | JP1 | JP2 | FaSSIF | FeSSIF |
| (1) | <0.8 | 451 | 470 | ≥475 |
| (2) | <0.7 | 447 | 445 | 463 |

Test Example 5

Rat Pharmacokinetic (PK) Assay and Measurement of Plasma Concentrations (1) Rat PK Study A DMSO solution (0.1 mL/kg) of test substance (0.3 mg/kg) was administered to a male rat (7-week old), and blood was collected at designated times (5, 10, 15, 30 min., 1, 2, 4, 8, 25 hr). Samples after the blood collection were separated by centrifugation (11000 g, 5 min.) to obtain plasmas.

(2) Measurement of Plasma Concentrations

A double volume of a mixed solution of acetonitrile/water (9:1) was added to a plasma sample obtained in (1) in order that proteins were extracted from the mixture. The sample after extraction was separated by centrifugation (11000 g, 5 min.), and the supernatant was measured by LC/MSMS (Nexera (Shimadzu)-QTrap5500 (AB SCIEX)). A calibration curve was measured simultaneously, and plasma concentrations were calculated.

The elimination rate constant (Kel) was calculated from two points of the elimination phase in the plasma concentration profile, and the half-life (T½) was calculated from the elimination rate constant.

$$Kel=-(\ln Conc1-\ln Conc2)/(t1-t2)$$

$$T\frac{1}{2}=0.693/Kel$$

Results are shown in the following table.

| Compound | Plasma half-life (h) |
|---|---|
| (1) | 10.5 |
| (2) | 13.2 |

Test Example 6

Effects of Test Substances on TL-17 Production in Plasmas of Antigen-Sensitized Mice Effects of test substances on IL-17 production in plasmas were assessed in antigen-sensitized mice. Antigen sensitization was performed according to Non Patent Literature 31. Nine-week old female C57BL/6J mice (Japan Charles River K.K.) were used as a test animal.

An emulsion prepared by mixing 3 mg/mL of myelin oligodendrocyte glycoprotein (MOG; ANASPEC) and 4 mg/mL of complete Freund's adjuvant (CFA; Chondrex) in an equal ratio was administered subcutaneously to a mouse at the bilateral abdomens at a volume of 50 µL/site (day 1). 1 µg/mL of pertussis toxin (PTX; List Biological Laboratories) was administered intraperitoneally at a volume of 200 µL/head (day 1 and 3). Blood was collected at day 8.

Administration was performed once daily for 7 days after the administration of emulsion (day 1 to 7). 0.5% (w/v) methyl cellulose (MC) was administered orally at a volume of 10 mL/kg to Normal group (normal mice) and Vehicle group (antigen-sensitized mice), and 0.03 mg/mL or 0.1 mg/mL of a test substance suspended in 0.5% (w/v) MC was administered orally at a volume of 10 mL/kg to a compound-administered group.

Blood was separated by centrifugation, and then the IL-17 concentration in plasma was measured with Quantikine (Registered trade mark) Mouse IL-17 ELISA Kit (R&D systems, Inc.).

The IL-17 concentration of Normal group was deemed to be 0% and that of Vehicle group was deemed to be 100%. The IL-17 concentration percentage (% of control) of the compound-administered group was calculated from the following equation.

$$\% \text{ of control}=(a-b)/(c-b)\times 100$$

a: IL-17 concentration of the compound-administered group
b: TL-17 concentration of the Normal group
c: IL-17 concentration of the Vehicle group Then, a dose of compound where the IL-17 concentration was decreased by 50% ($ED_{50}$) was calculated from the following equation.

$$ED_{50}=10^{\{log(A/B)\times(50-D)/(C-D)+log(B)\}};$$

provided that $ED_{50}$=B in the case D=50, and $ED_{50}$>B in the case D>50
A: dosed amount of the lower dose group (i.e. 0.3 mg/kg)
B: dosed amount of the higher dose group (i.e. 1 mg/kg)
C: % of control at the lower dose group
D: % of control at the higher dose group Results are shown in the following table.

| Compound | Dose (mg/kg) | % of control | $ED_{50}$ (mg/kg) |
|---|---|---|---|
| (1) | 0.3 (=A) | 66 (=C) | 0.5 |
|  | 1 (=B) | 24 (=D) |  |
| (2) | 0.3 (=A) | 85 (=C) | >1 |
|  | 1 (=B) | 54 (=D) |  |

Test Example 7

Effects of Test Substances on IL-17 Production in Plasmas of Cytokine-Stimulated Normal Mice Effects of Lest substances on IL-17 production in plasmas were assessed in normal mice. The assessment was performed according to Non Patent Literature 32. Nine-week old female C57BL/6J mice (Japan Charles River K.K.) were used as a test animal.

A mixed solution prepared by mixing Recombinant Mouse IL-1 beta/IL-1F2 Protein (R&D systems, INC.) and Recombinant Mouse IL-23 Protein (R&D systems, INC.) at a final concentration of 1.5 µg/mL was administered intravenously to all groups at the tail vein at a volume of 200 µL/head. Blood was collected 2 hours after the administration of cytokine solution.

Administration was performed 28 hours before the administration of cytokine solution. 0.5% (w/v) methyl cellulose (MC) and 0.1 mg/mL of a test substance suspended in 0.5% (w/v) MC were administered orally at a single volume of 0.2 mL/head to Vehicle group and a compound-administered group, respectively.

Blood was separated by centrifugation, and then the IL-17 concentration in plasma was measured with Quantikine (Registered trade mark) Mouse IL-17 ELISA Kit (R&D systems, Inc.).

The IL-17 concentration of Vehicle group was deemed to be 100%, and the IL-17 concentration percentage of the compound-administered group to the Vehicle group was calculated from the following equation. Results are shown in the following table.

$$\%=a/b\times 100$$

a: IL-17 concentration of the compound-administered group
b: IL-17 concentration of the Vehicle group

| Compound | IL-17 concentration (%) |
|---|---|
| (1) | 52 |
| (2) | 67 |

Formulation Examples

Formulation Examples in the present invention include, for example, the following formulations. The present invention, however, is not intended to be limited to these Formulation Examples.

Formulation Example 1 (Preparation of a Capsule)

| 1) | Example 1 Compound | 30 mg |
| --- | --- | --- |
| 2) | Microcrystalline cellulose | 10 mg |
| 3) | Lactose | 19 mg |
| 4) | Magnesium stearate | 1 mg |

Ingredients 1), 2), 3), and 4) are mixed to be filled in a gelatin capsule.

Formulation Example 2 (Preparation of a Tablet)

| 1) | Example 1 Compound | 10 g |
| --- | --- | --- |
| 2) | Lactose | 50 g |
| 3) | Cornstarch | 15 g |
| 4) | Carmellose calcium | 44 g |
| 5) | Magnesium stearate | 1 g |

The total amount of Ingredients 1), 2), and 3) and 30 g of Ingredient 4) are combined with water, dried in vacuo, and then granulated. The resulted granules are mixed with 14 g of Ingredient 4) and 1 g of Ingredient 5), and tableted with a tableting machine. In this manner, 1000 tablets comprising 10 mg of Example 1 Compound per each are obtained.

INDUSTRIAL APPLICABILITY

A compound of Formula (1) or (2) or a pharmaceutically acceptable salt thereof is expected to be useful for treating or preventing autoimmune diseases, allergic diseases, dry eye, fibrosis, cancers, metabolic disease, ischemia, cardiomyopathy, hypertension, and periodontal disease.

The invention claimed is:

1. A compound of Formula (1):

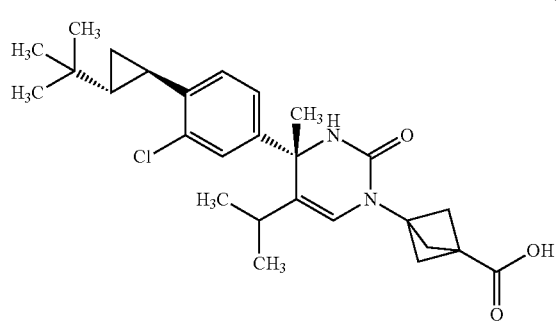

(1)

or a pharmaceutically acceptable salt thereof.

2. A compound of Formula (2):

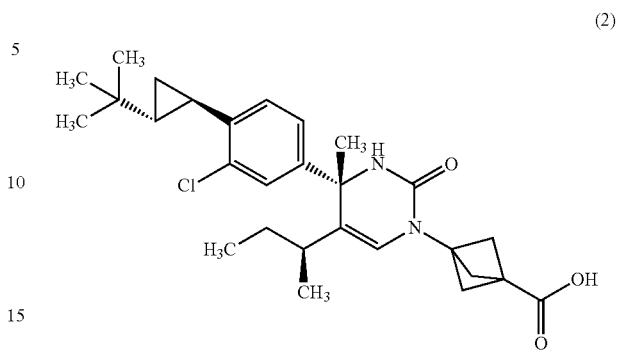

(2)

or a pharmaceutically acceptable salt thereof.

3. A pharmaceutical composition comprising a compound according to claim 1 or 2 or a pharmaceutically acceptable salt thereof and a pharmaceutically acceptable carrier.

4. A method of antagonizing RORγ, comprising administering a therapeutically effective amount of a compound according to claim 1 or 2 or a pharmaceutically acceptable salt thereof to a mammal.

5. A method of treating a disease selected from the group consisting of allergic diseases, dry eye, fibrosis, metabolic disease, ischemia, cardiomyopathy, hypertension, and periodontal disease, comprising administering a therapeutically effective amount of a compound according to claim 1 or 2 or a pharmaceutically acceptable salt thereof to a mammal.

6. A method of treating an autoimmune disease selected from the group consisting of rheumatoid arthritis, psoriasis, inflammatory bowel disease, multiple sclerosis, systemic lupus erythematosus, Behcet's disease, sarcoidosis, Harada disease, ankylosing spondylitis, uveitis, polymyalgia rheumatica, type I diabetes, graft-versus-host disease, alopecia areata, and vitiligo, comprising administering a therapeutically effective amount of a compound of claim 1 or 2, or a pharmaceutically acceptable salt thereof, to a mammal.

7. The method of claim 6, wherein the autoimmune disease is rheumatoid arthritis.

8. The method of claim 6, wherein the autoimmune disease is psoriasis.

9. The method of claim 6, wherein the autoimmune disease is inflammatory bowel disease wherein the inflammatory bowel disease is Crohn's disease.

10. The method of claim 6, wherein the autoimmune disease is inflammatory bowel disease wherein the inflammatory bowel disease is ulcerative colitis.

11. A compound of formula (1):

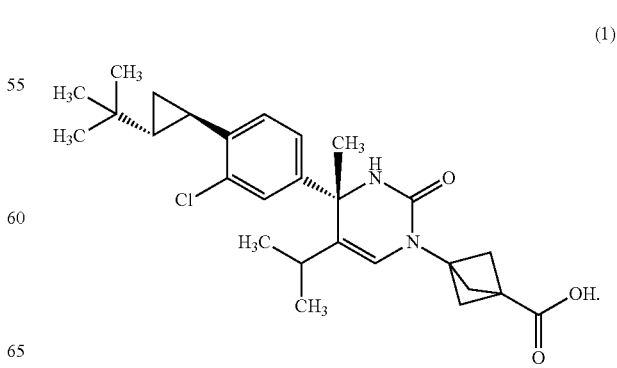

(1)

12. A compound of formula (2):

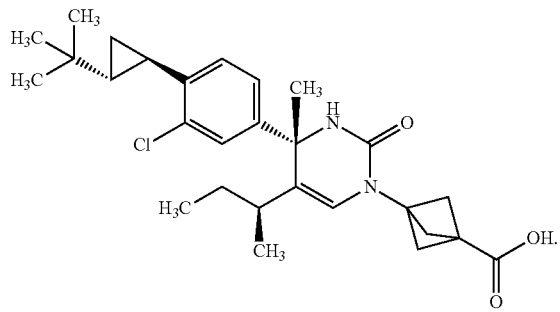

(2)

13. A pharmaceutical composition comprising the compound of claim 11 or 12 and a pharmaceutically acceptable carrier.

14. A method of antagonizing RORγ, comprising administering a therapeutically effective amount of the compound of claim 11 or 12 to a mammal.

15. A method of treating a disease selected from the group consisting of allergic diseases, dry eye, fibrosis, metabolic disease, ischemia, cardiomyopathy, hypertension, and periodontal disease, comprising administering a therapeutically effective amount of the compound of claim 11 or 12 to a mammal.

16. A method of treating an autoimmune disease selected from the group consisting of rheumatoid arthritis, psoriasis, inflammatory bowel disease, multiple sclerosis, systemic lupus erythematosus, Behcet's disease, sarcoidosis, Harada disease, ankylosing spondylitis, uveitis, polymyalgia rheumatica, type I diabetes, graft-versus-host disease, alopecia areata, and vitiligo, comprising administering a therapeutically effective amount of the compound of claim 11 or 12 to a mammal.

17. The method of claim 16, wherein the autoimmune disease is rheumatoid arthritis.

18. The method of claim 16, wherein the autoimmune disease is psoriasis.

19. The method of claim 16, wherein the autoimmune disease is inflammatory bowel disease wherein the inflammatory bowel disease is Crohn's disease.

20. The method of claim 16, wherein the autoimmune disease is inflammatory bowel disease wherein the inflammatory bowel disease is ulcerative colitis.

* * * * *

UNITED STATES PATENT AND TRADEMARK OFFICE
CERTIFICATE OF CORRECTION

PATENT NO. : 10,899,717 B2  
APPLICATION NO. : 16/287870  
DATED : January 26, 2021  
INVENTOR(S) : Takayuki Sakai et al.

Page 1 of 1

It is certified that error appears in the above-identified patent and that said Letters Patent is hereby corrected as shown below:

In the Claims

At Column 57, Claim number 14, Line number 21, please replace "RORy" with --RORγ--

Signed and Sealed this  
Eleventh Day of May, 2021

Drew Hirshfeld  
*Performing the Functions and Duties of the*  
*Under Secretary of Commerce for Intellectual Property and*  
*Director of the United States Patent and Trademark Office*